(12) United States Patent
Ranjan et al.

(10) Patent No.: US 11,136,591 B2
(45) Date of Patent: Oct. 5, 2021

(54) PLANT CELLS AND PLANTS MODIFIED TO INCREASE RESISTANCE TO NECROTROPHS OR DROUGHT AND METHODS OF SELECTING AND USING THE SAME

(71) Applicant: Wisconsin Alumni Research Foundation, Madison, WI (US)

(72) Inventors: Ashish Ranjan, Madison, WI (US); Mehdi Kabbage, Madison, WI (US); Damon Smith, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 145 days.

(21) Appl. No.: 16/050,864

(22) Filed: Jul. 31, 2018

(65) Prior Publication Data

US 2019/0085357 A1 Mar. 21, 2019

Related U.S. Application Data

(60) Provisional application No. 62/538,978, filed on Jul. 31, 2017.

(51) Int. Cl.
*C12N 15/82* (2006.01)
*C12N 9/02* (2006.01)

(52) U.S. Cl.
CPC ....... *C12N 15/8279* (2013.01); *C12N 9/0008* (2013.01); *C12N 9/0036* (2013.01); *C12N 15/8273* (2013.01); *C12Y 106/03001* (2013.01)

(58) Field of Classification Search
None
See application file for complete search history.

(56) References Cited

U.S. PATENT DOCUMENTS

2007/0124833 A1* 5/2007 Abad .................. C12N 15/8273
800/278
2008/0047033 A1* 2/2008 Kogel ................ C12N 15/8282
800/279

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
McConnell et al. (Nature, 411:709-713, 2001).*
Hanzawa et al. (PNAS, 102:7748-7753, 2005).*
Wishart et al. (JBC, 270:26782-26785, 1995).*
Nishimura et al. (Plant Cell Physiol., 41 (5):583-590, 2000.*
Yang et al. (PNAS, 98:11438-11443, 2001; abstract; pp. 11442-11443).*
Orman-Ligeza et al. (Development, 143:3328-3339, Published 2016).*
Kaur et al. (Amino acids, 50:79-94, 2018).*
Doerks et al., (TIG, 14:248-250, 1998).*
Smith et al. (Nature Biotechnology, 15:1222-1223, 1997).*
Bork et al. (TIG, 12:425-427, 1996).*
Ranjan et al. (APS.CPS Joint meeting , Aug. 9-13, Minneapolis, Minnesota, vol. 104 (supplement 3), No. 11, 2014, pp. S.31-S.138; Published 2014).*
Ji et al. (J Plant Biotechnol., 38:22-29, 2011; English translation provided).*
Alexieva, V., et al. (2001). "The effect of drought and ultraviolet radiation on growth and stress markers in pea and wheat." Plant, Cell & Environment 24(12): 1337-1344.
Alscher, R. G., et al. (1997). "Reactive oxygen species and antioxidants: Relationships in green cells." Physiologia Plantarum 100(2): 224-233.
Amselem, J., et al. (2011). "Genomic Analysis of the Necrotrophic Fungal Pathogens *Sclerotinia sclerotiorum* and *Botrytis cinerea*." PLoS Genet 7(8): e1002230.
Apel, K., et al. (2004). "Reactive Oxygen Species: Metabolism, Oxidative Stress, and Signal Transduction." Annual Review of Plant Biology 55(1): 373-399.
Arthikala, M.-K., et al. (2014). "RbohB, a Phaseolus vulgaris NADPH oxidase gene, enhances symbiosome number, bacteroid size, and nitrogen fixation in nodules and impairs mycorrhizal colonization." New Phytologist 202(3): 886-900.
Baxter, A., et al. (2013). "ROS as key players in plant stress signalling." Journal of Experimental Botany.
Bhattacharjee, S. (2005). "Reactive oxygen species and oxidative burst: Roles in stress, senescence and signal transduction in plants." Current Science 89(7): 1113-1121.
Chaouch, S., et al. (2012). "AtRbohF is a crucial modulator of defence-associated metabolism and a key actor in the interplay between intracellular oxidative stress and pathogenesis responses in *Arabidopsis*." The Plant Journal 69(4): 613-627.
Cheng, C., et al. (2013). "Genome-Wide Analysis of Respiratory Burst Oxidase Homologs in Grape (*Vitis vinifera* L.)." International Journal of Molecular Sciences 14(12): 24169-24186.
Dubiella, U., et al. (2013). "Calcium-dependent protein kinase/NADPH oxidase activation circuit is required for rapid defense signal propagation." Proceedings of the National Academy of Sciences 110(21): 8744-8749.

(Continued)

Primary Examiner — Vinod Kumar
(74) *Attorney, Agent, or Firm* — Quarles & Brady LLP

(57) ABSTRACT

The invention generally relates to plant cells and plants modified to increase resistance to necrotrophs or drought and methods of selecting and using the same. More specifically, the invention relates in part to plant cells and/or plants modified to eliminate or reduce as compared to control plants cell the NADPH oxidase activity or expression of certain respiratory burst oxidase homolog (RBOH) proteins and methods of selecting for and using the same.

17 Claims, 20 Drawing Sheets

Specification includes a Sequence Listing.

(56) References Cited

OTHER PUBLICATIONS

Foreman, J., et al. (2003). "Reactive oxygen species produced by NADPH oxidase regulate plant cell growth." Nature 422(6930): 442-446.

Glyan'Ko, A. K., et al. (2010). "Structural and functional characteristics of plant NADPH oxidase: A review." Applied Biochemistry and Microbiology 46(5): 463-471.

Govrin, E. M. et al. (2000). "The hypersensitive response facilitates plant infection by the necrotrophic pathogen Botrytis cinerea." Current Biology 10(13): 751-757.

Kabbage, M., et al. (2013). "Cell Death Control: The Interplay of Apoptosis and Autophagy in the Pathogenicity of Sclerotinia sclerotiorum." PLoS Pathog 9(4): e1003287.

Kabbage, M., et al. (2015). "Pathogenic attributes of Sclerotinia sclerotiorum: Switching from a biotrophic to necrotrophic lifestyle." Plant Science 233: 53-60.

Kadota, Y., et al. (2014). "Direct Regulation of the NADPH Oxidase RBOHD by the PRR Associated Kinase BIK1 during Plant Immunity." Molecular Cell 54(1): 43-55.

Kadota, Y., et al. (2015). "Regulation of the NADPH Oxidase RBOHD During Plant Immunity." Plant and Cell Physiology 56(8): 1472-1480.

Kandoth, P. K., et al. (2013). "A virus-induced gene silencing method to study soybean cyst nematode parasitism in Glycine max." BMC Research Notes 6(1): 255.

Kaya, H., et al. (2014). "$Ca^{2+}$-Activated Reactive Oxygen Species Production by Arabidopsis RbohH and RbohJ Is Essential for Proper Pollen Tube Tip Growth." The Plant Cell 26(3): 1069-1080.

Kim KS, et al. (2008) Oxalic acid is an elicitor of plant programmed cell death during Sclerotinia sclerotiorum disease development. Mol Plant Microbe Interact 21: 605-612.

Kimura, S., et al. (2012). "Protein phosphorylation is a prerequisite for the $Ca^{2+}$-dependent activation of Arabidopsis NADPH oxidases and may function as a trigger for the positive feedback regulation of $Ca^{2+}$ and reactive oxygen species." Biochimica et Biophysica Acta (BBA)—Molecular Cell Research 1823(2): 398-405.

Kobayashi, M., et al. (2007). "Calcium-Dependent Protein Kinases Regulate the Production of Reactive Oxygen Species by Potato NADPH Oxidase." The Plant Cell 19(3): 1065-1080.

Kwak, J. M., et al. (2003). "NADPH oxidase AtrbohD and AtrbohF genes function in ROS dependent ABA signaling in Arabidopsis." The EMBO Journal 22(11): 2623-2631.

Lambeth, J. D. (2004). "NOX enzymes and the biology of reactive oxygen." Nat Rev Immunol 4(3): 181-189.

Lassig, R., et al. (2014). "Pollen tube NAD(P)H oxidases act as a speed control to dampen growth rate oscillations during polarized cell growth." The Plant Journal 78(1): 94-106.

Letunic, I., et al. (2015). "SMART: recent updates, new developments and status in 2015." Nucleic Acids Research 43(D1): D257-D260.

Li, X., et al. (2015). "Tomato SlRbohB, a member of the NADPH oxidase family, is required for disease resistance against Botrytis cinerea and tolerance to drought stress." Frontiers in Plant Science 6.

Liang, X., et al. (2015). "Oxaloacetate acetylhydrolase gene mutants of Sclerotinia sclerotiorumdo not accumulate oxalic acid, but do produce limited lesions on host plants." Molecular Plant Pathology 16(6):559-571.

Lin, F., et al. (2009). "Alternative Splicing and Differential Expression of Two Transcripts of Nicotine Adenine Dinucleotide Phosphate Oxidase B Gene from Zea mays." Journal of Integrative Plant Biology 51(3): 287-298.

Marino, D., et al. (2011). "A Medicago truncatula NADPH oxidase is involved in symbiotic nodulefunctioning." The New Phytologist 189(2): 580-592.

Marino, D., et al. (2012). "A burst of plant NADPH oxidases." Trends in Plant Science 17(1): 9-15.

Miller, G., et al. (2009). "The Plant NADPH Oxidase RBOHD Mediates Rapid Systemic Signaling in Response to Diverse Stimuli." Science Signaling 2(84): ra45-ra45.

Mittler, R., et al. (2011). "ROS signaling: the new wave?" Trends in Plant Science 16(6): 300-309.

Müller, K., et al. (2009). "The NADPH-oxidase AtrbohB plays a role in Arabidopsis seed after ripening." New Phytologist 184(4): 885-897.

Nozaki, M., et al. (2013). "AtRbohF Contributes to Non-Host Resistance to Magnaporthe oryzae in Arabidopsis." Bioscience, Biotechnology, and Biochemistry 77(6): 1323-1325.

Oda, T., et al. (2010). "Structure of the N-terminal Regulatory Domain of a Plant NADPH Oxidase and Its Functional Implications." The Journal of Biological Chemistry 285(2): 1435-1445.

Peltier, A. J., et al. (2009). "Soybean Stem Lignin Concentration Relates to Resistance to Sclerotinia sclerotiorum." Plant Disease 93(2): 149-154.

Peltier, A. J., et al. (2012). "Biology, Yield loss and Control of Sclerotinia Stem Rot of Soybean." Journal of Integrated Pest Management 3(2): B1.

Sagi, M., et al. (2001). "Superoxide production by plant homologues of the gp91(phox) NADPH oxidase. Modulation of activity by calcium and by tobacco mosaic virus infection." Plant Physiol126(3):1281-1290.

Sagi, M., et al. (2006). "Production of Reactive Oxygen Species by Plant NADPH Oxidases." Plant Physiology 141(2): 336-340.

Sharma, P., et al. (2012). "Reactive Oxygen Species, Oxidative Damage, and Antioxidative Defense Mechanism in Plants under Stressful Conditions." Journal of Botany 2012: 26.

Simon-Plas, F., et al. (2002). "The plasma membrane oxidase NtrbohD is responsible for AOS production in elicited tobacco cells." The Plant Journal 31(2): 137-147.

Torres, M. A. et al. (2005). "Functions of the respiratory burst oxidase in biotic interactions, abiotic stress and development." Current Opinion in Plant Biology 8(4): 397-403.

Torres, M. A., et al. (2002). "Arabidopsis gp91phox homologues AtrbohD and AtrbohF are required for accumulation of reactive oxygen intermediates in the plant defense response." Proceedings of the National Academy of Sciences 99 (1): 517-522.

Tripathy, B. C. et al. (2012). "Reactive oxygen species generation and signaling in plants." Plant Signaling & Behavior 7(12): 1621-1633.

Wang, G.-F., et al. (2013). "Characterization of Rice NADPH Oxidase Genes and Their Expression under Various Environmental Conditions." International Journal of Molecular Sciences 14(5): 9440-9458.

Wang, X., et al. (2016). "The plasma membrane NADPH oxidase OsRbohA plays a crucial role in developmental regulation and drought-stress response in rice." Physiologia Plantarum 156(4): 421-443.

Williams, B., et al. (2011). "Tipping the Balance: Sclerotinia sclerotiorum Secreted Oxalic Acid Suppresses Host Defenses by Manipulating the Host Redox Environment." PLoS Pathog 7(6): e1002107.

Wong, H. L., et al. (2007). "Regulation of Rice NADPH Oxidase by Binding of Rac GTPase to Its N-Terminal Extension." The Plant Cell 19(12): 4022-4034.

Xu, L., et al., (2015). "pH dependency of sclerotial development and pathogenicity revealed by using genetically defined oxalate-minus mutants of Sclerotinia sclerotiorum." Environmental Microbiology 17: 2896-2909.

Zhang, C., et al. (2010). "The Development of an Efficient Multipurpose Bean Pod Mottle Virus Viral Vector Set for Foreign Gene Expression and RNA Silencing." Plant Physiology 153(1): 52-65.

Zhang, C., et al. (2013). Virus-Induced Gene Silencing in Soybean and Common Bean. Virus-Induced Gene Silencing: Methods and Protocols. A. Becker. Totowa, NJ, Humana Press: 149-156.

\* cited by examiner

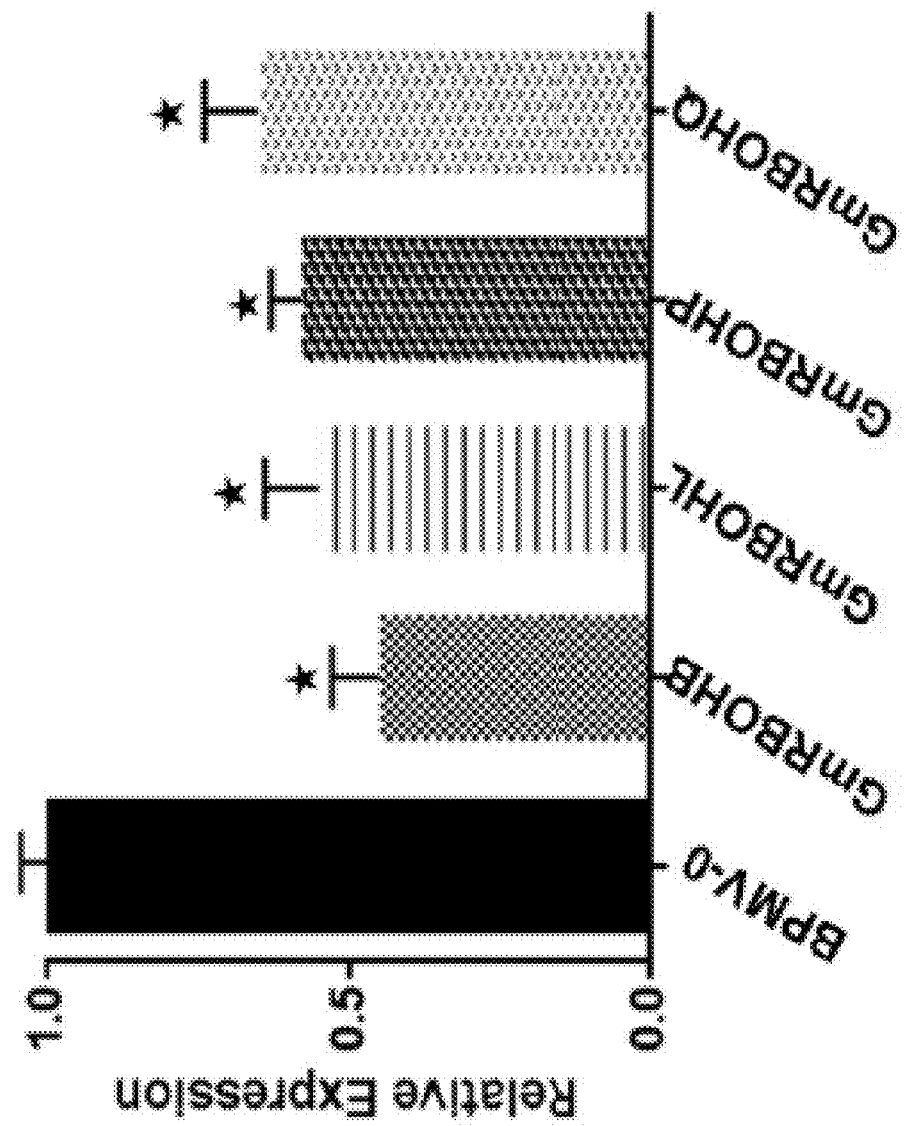

FIG. 8A

BPMV-GmRBOHVI

BPMV-0

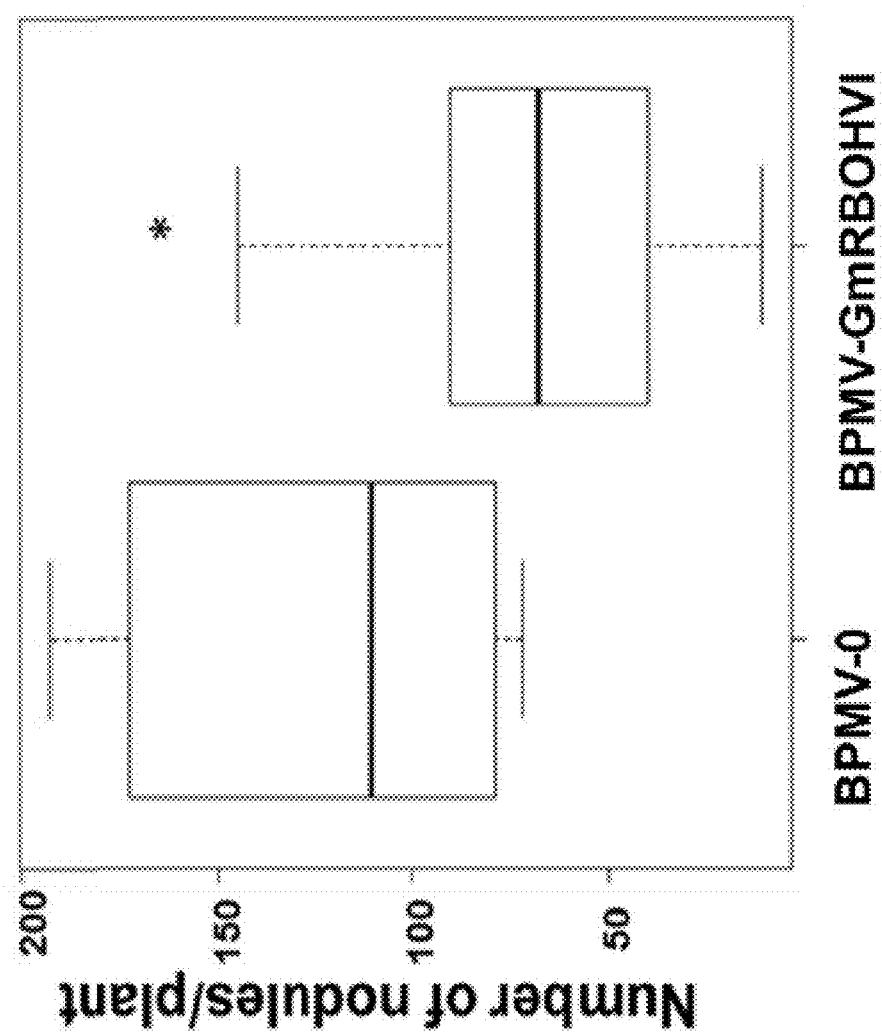

US 11,136,591 B2

PLANT CELLS AND PLANTS MODIFIED TO INCREASE RESISTANCE TO NECROTROPHS OR DROUGHT AND METHODS OF SELECTING AND USING THE SAME

CROSS-REFERENCE TO RELATED PATENT APPLICATIONS

The present application claims the benefit of priority to U.S. Provisional Patent Application No. 62/538,978, filed on Jul. 31, 2017, the content of which is incorporated herein by reference in its entirety.

SEQUENCE LISTING

This application is being filed electronically via EFS-Web and includes an electronically submitted Sequence Listing in .txt format. The .txt file contains a sequence listing entitled "2018-12-03_5671-00083_ST25.txt" created on Dec. 3, 2018, and is 47,058 bytes in size. The Sequence Listing contained in this .txt file is part of the specification and is hereby incorporated by reference herein in its entirety.

INTRODUCTION

Necrotrophs are organisms that kill the living cells of their hosts and then feed on the resulting dead matter. A prototypical necrotroph is *Sclerotinia sclerotiorum*. *Sclerotinia sclerotiorum* is a cosmopolitan fungal pathogen that infects virtually all dicotyledonous plants. *S. sclerotiorum* is a prolific producer of cell wall degrading enzymes (e.g. pectinases, cellulases, hemicellulases), which facilitate plant cell wall degradation and host colonization (Amselem, Cuomo et al. 2011). In addition to its lytic repertoire, an important factor governing the pathogenic success of *S. sclerotiorum* is the secretion of the key virulence factor oxalic acid (OA). Mutants defective in OA production are poorly pathogenic and are unable to overcome host defenses (Williams, Kabbage et al. 2011, Kabbage, Williams et al. 2013, Liang, Liberti et al. 2015). OA was shown to contribute to pathogenesis in some ways that facilitate the colonization of the host plant, including the inhibition of host defenses (Williams, Kabbage et al. 2011), pH-mediated activation of CWDEs and the inhibition of autophagy (Kabbage, Williams et al. 2013). Importantly, OA induces apoptotic-like PCD, a process that is largely reliant on reactive oxygen species (ROS) (Kim et al., 2008). Thus, the regulation of ROS plays a critical role in the pathogenic success of *S. sclerotiorum*, particularly at the later stages of the infection process where ROS generation and tissue cell death culminates in the establishment of disease (Williams, Kabbage et al. 2011).

*S. sclerotiorum* can cause considerable damage to crop plants and has proven difficult to control, with host resistance being inadequate. In soybean, for example, this fungus causes *Sclerotinia* Stem Rot (SSR), also known as white mold disease. SSR can be a significant yield limiting disease, and yield losses greater than 10 million bushels (270 million kg) per year are common (Peltier, Bradley et al. 2012). There thus remains a need in the art for plants having increased resistance to necrotrophs such as *S. sclerotiorum*.

SUMMARY

In one aspect of the present invention, plant cells are provided. The plant cells may be modified to eliminate or reduce as compared to a control plant cell the NADPH oxidase activity or expression of at least one, two, three, four, or more respiratory burst oxidase homolog (RBOH) protein(s) selected from the group consisting of SEQ ID NO: 1 (GmRBOHB), a variant or homolog of SEQ ID NO: 1 having at least 60%, 70%, 80%, 85%, 90%, 95%, or 99% sequence identity to SEQ ID NO: 1, SEQ ID NO: 2 (GmRBOHL), a variant or homolog of SEQ ID NO: 2 having at least 60%, 70%, 80%, 85%, 90%, 95%, or 99% sequence identity to SEQ ID NO: 2, SEQ ID NO: 3 (GmRBOHP), a variant or homolog of SEQ ID NO: 3 having at least 60%, 70%, 80%, 85%, 90%, 95%, or 99% sequence identity to SEQ ID NO: 3, SEQ ID NO: 4(GmRBOHQ), and a variant or homolog of SEQ ID NO: 4 having at least 60%, 70%, 80%, 85%, 90%, 95%, or 99% sequence identity to SEQ ID NO: 4.

In another aspect, plants are provided. The plants may include any one of the plant cells described herein. The plants may include plants in which every cell of the plant is a plant cell modified as described herein. Alternatively, the plants may include plants in which only certain tissues within the plant include the plant cells described herein.

In a further aspect, methods of generating a plant having increased resistance to a necrotroph and/or drought as compared to a control plant are provided. The methods may include modifying at least one cell in the plant to eliminate or reduce as compared to a control plant cell the NADPH oxidase activity or expression of at least one, two, three, four, or more respiratory burst oxidase homolog (RBOH) protein(s) selected from the group consisting of SEQ ID NO: 1 (GmRBOHB), a variant or homolog of SEQ ID NO: 1 having at least 60%, 70%, 80%, 85%, 90%, 95%, or 99% sequence identity to SEQ ID NO: 1, SEQ ID NO: 2 (GmRBOHL), a variant or homolog of SEQ ID NO: 2 having at least 60%, 70%, 80%, 85%, 90%, 95%, or 99% sequence identity to SEQ ID NO: 2, SEQ ID NO: 3 (GmRBOHP), a variant or homolog of SEQ ID NO: 3 having at least 60%, 70%, 80%, 85%, 90%, 95%, or 99% sequence identity to SEQ ID NO: 3, SEQ ID NO: 4(GmRBOHQ), and a variant or homolog of SEQ ID NO: 4 having at least 60%, 70%, 80%, 85%, 90%, 95%, or 99% sequence identity to SEQ ID NO: 4.

In a still further aspect, the present invention relates to methods of screening for a plant having increased resistance to a necrotroph and/or drought resistance as compared to a control plant. The methods may include a) generating a plurality of plant variants, and b) measuring in at least one cell of the plurality of plant variants the NADPH oxidase activity or expression of at least one, two, three, four, or more respiratory burst oxidase homolog (RBOH) protein(s) selected from the group consisting of SEQ ID NO: 1 (GmRBOHB), a variant or homolog of SEQ ID NO: 1 comprising at least 60%, 70%, 80%, 85%, 90%, 95%, or 99% sequence identity to SEQ ID NO: 1, SEQ ID NO: 2 (GmRBOHL), a variant or homolog of SEQ ID NO: 2 comprising at least 60%, 70%, 80%, 85%, 90%, 95%, or 99% sequence identity to SEQ ID NO: 2, SEQ ID NO: 3 (GmRBOHP), a variant or homolog of SEQ ID NO: 3 comprising at least 60%, 70%, 80%, 85%, 90%, 95%, or 99% sequence identity to SEQ ID NO: 3, SEQ ID NO: 4(GmRBOHQ), and a variant or homolog of SEQ ID NO: 4 comprising at least 60%, 70%, 80%, 85%, 90%, 95%, or 99% sequence identity to SEQ ID NO: 4. Optionally, the methods may further include c) selecting the plant variants wherein the NADPH oxidase activity or expression of the at least one RBOH protein is reduced or eliminated as compared to the NADPH oxidase activity or expression of the at least one RBOH protein in the control plant.

In another aspect, the present invention relates to methods of using the plants described herein. The methods may include planting any one of the plants described herein in an area. The area may be at risk of drought and having below average precipitation or may include a necrotroph capable of infecting the plant.

BRIEF DESCRIPTION OF DRAWINGS

FIG. 1A. Domain organization of 17 putative soybean respiratory burst oxidase homologs (GmRBOHs). The domain organization is based on SMART alignment tool (smart.embl-heidelberg.de/smart/set_mode.cgi?GENOMIC=1). FIG. 1B. Phylogenetic relation analysis of 17 soybean respiratory burst oxidase homologs (GmRBOHs) and 10 *Arabidopsis* respiratory burst oxidase homologs (AtRBOHs). Phylogenetic tree was constructed using PhyML 3.0 based on the maximum likelihood method. A total of six groups of GmRBOHs were identified. Branch lengths are proportional to the number of substitutions per site (see scale bars). Only bootstrap values >50% were used to resolve branching.

FIG. 3A. Disease symptoms observed following petiole inoculation with an agar plug containing actively growing mycelia of *S. sclerotiorum* at 6, 12, 24, 48, 72, and 96 hours post inoculation (hpi). FIG. 3B. RNAs isolated from non-infected and infected soybean stems were used to analyze expression of GmRBOH-VI using qRT-PCR. The relative expression values were calculated by comparing the expression value of genes to non-inoculated soybean stem tissues using the 2+ΔΔCt method. GmCons15 was used as an endogenous control. Data presented as means±SE from three independent experiments.

FIG. 4A. Disease symptoms observed at 6, 12, 24, 48, 72, and 96 hours post inoculation (hpi) following A2 inoculation. FIG. 4B. RNAs isolated from non-infected and infected soybean stems were used to analyze expression of GmRBOH-VI using qRT-PCR. The relative expression values were calculated by comparing the expression value of genes to non-inoculated soybean stem tissues using the 2-DDCt method. GmCons15 was used as endogenous control. Data presented as means±SE from three independent experiments.

FIGS. 5A-5C shows the silencing of GmRBOH-VI leads to enhanced resistance to *S. sclereotiorum*. FIG. 5A. Silencing efficiency of GmRBOH-VI. The first true leaves of 10-day-old soybean plants were used for biolistic delivery of BPMV constructs, BPMV-0 (empty vector control) and BPMVGmRBOH-VI. The silencing efficiency was calculated by comparing transcript levels of each GmRBOH-VI genes in BPMV-GmRBOH-VI VIGS plants with its corresponding sequence in BPMV-0-infected plants. FIG. 5B. Lesion length and FIG. 5C disease symptom following petiole inoculation with *S. sclerotiorum*. Lesion lengths were measured from 72 to 120 hpi as shown in FIG. 5B. At 120 hpi the control plants were completely wilted in contrast to BPMV-GmRBOH-VI inoculated plants as shown in FIG. 5C. Eight plants were used for each of the three biological repeats. Data presented (FIGS. 5A and 5B) as mean±SD from three independent experiments and * above the columns indicate significant differences at the p<0.05 level. Yellow arrow shows a red discoloration at the edge of the lesion.

FIG. 7D shows the recovery of plants after watering was resumed. In each panel, the BPMV-0 empty vector plants (left), and the GmRBOH-VI-silenced plants (right) are shown in each panel. Eight plants were used for each of the three biological repeats.

FIGS. 8A-8B show silencing of GmRBOH-VI reduces nodulation. FIG. 8A. Nodule formation in empty vector control (BPMV-0) and GmRBOH-VI-silenced plants (BPMV-GmRBOH-VI). FIG. 8B. Number of nodules per plant. Plants were inoculated with 3 ml of *Bradyrhizobium diazoefficiens* USDA 110 at an optical density of 0.15. 18 days after *B. diazoefficiens* inoculation, the number of nodules on each plant was counted manually. A total of 19 plants for each treatment were used for the nodulation study, * above indicate significant differences at p<0.05.

FIG. 9A. Detection of GmRBOHB-HA, GmRBOHL-HA, GmRBOHP-HA and GmRBOHQ-HA from infiltrated *N. benthamiana* leaves. The pGWB414-GmRBOHB-HA, pGWB414-GmRBOHL-HA, pGWB414-GmRBOHP-HA, pGWB414-GmRBOHQ-HA and pGWB414-eHA (empty vector) constructs were expressed in leaves by *Agrobacterium* infiltration, and samples were collected at 48 hours post infiltration. Total soluble protein extracts were prepared and separated using SDS-PAGE and tagged GmRBOH proteins were detected using an HA-specific antibody. Equal loading of protein samples was confirmed by Ponceau staining. FIG. 9B. Lesion area. pGWB414-GmRBOHB-HA, pGWB414-GmRBOHL-HA, pGWB414-GmRBOHP-HA, pGWB414-GmRBOHQ-HA and pGWB414-eHA were expressed in *N. benthamiana* leaves using *Agrobacterium*. At 24 hours post infiltration, leaves were detached and challenged with *S. sclerotiorum*. Lesion diameter was measured 24 hpi. FIG. 9C. Lesion development in representative leaves. Mean lesion area±SD from three independent experiments were measured, each experiment contained 5 leaves. * above the columns indicate significant difference at p<0.05.

DETAILED DESCRIPTION

Figure 1A:
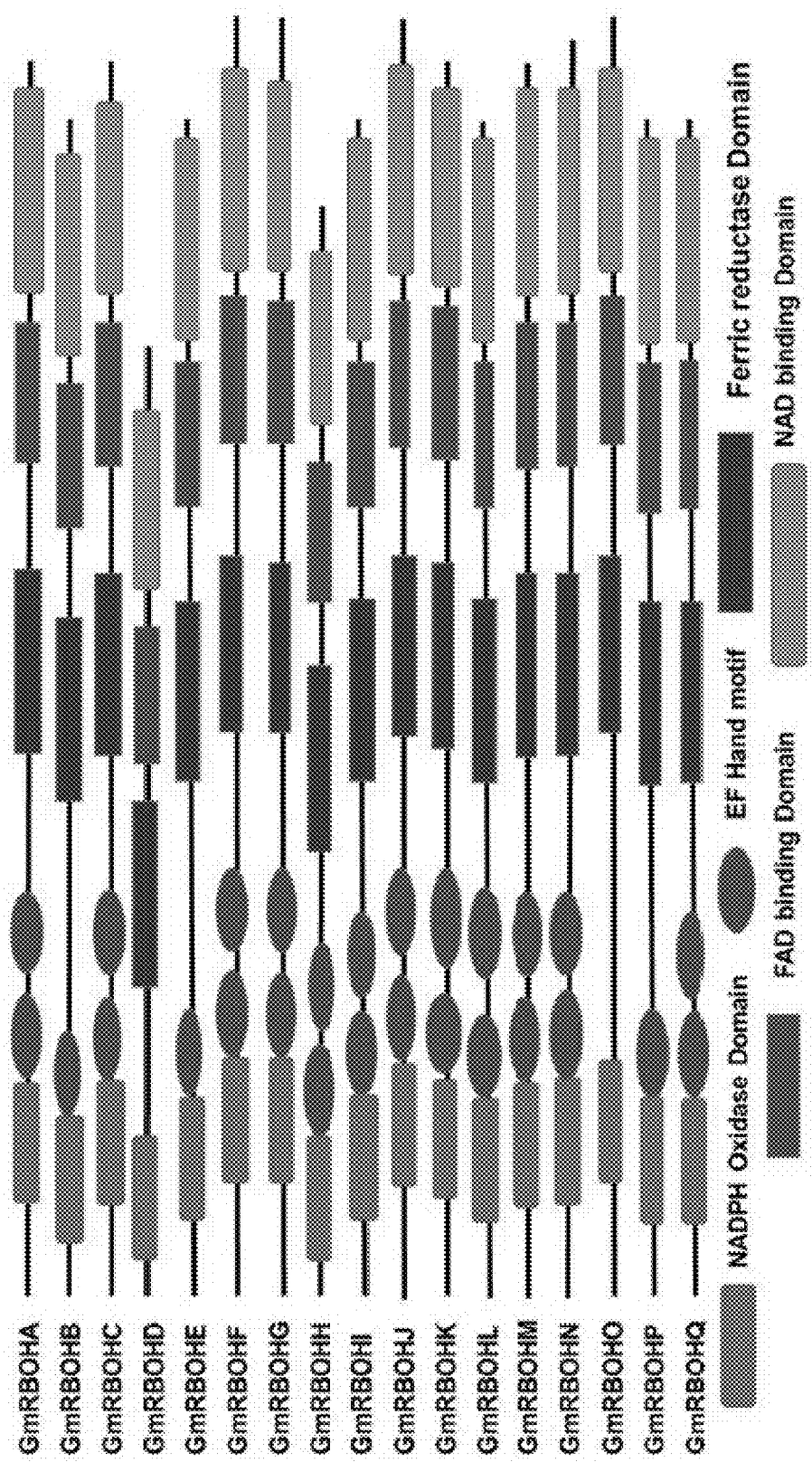
FIGS. 1A-1B show the domain organization and phylogenetic tree of soybean respiratory burst oxidase homologs (GmRBOHs).

Here, in the non-limiting Examples, the present inventors, using protein sequence similarity searches, have identified seventeen soybean RBOHs (GmRBOHs) and studied their contribution to *Sclerotinia* Stem Rot (SSR) disease development, drought tolerance and nodulation. The inventors clustered the soybean RBOH genes into six groups of orthologs based on phylogenetic analysis with their *Arabidopsis* counterparts. Transcript analysis of all seventeen GmRBOHs revealed that out of the six identified groups, group VI (GmRBOH-VI) (SEQ ID NOS: 1-4) was specifically and drastically induced following *S. sclerotiorum* challenge. Virus-induced gene silencing (VIGS) of GmRBOH-VI using Bean pod mottle virus (BPMV) resulted in enhanced resistance to *S. sclerotiorum* and markedly reduced ROS levels during disease development. Coincidently, GmRBOH-VI-silenced plants were also found to be drought tolerant and had a reduce capacity to form nodules. Without being limited by theory, the results suggest that the pathogenic development of a necrotroph such as *S. sclerotiorum* requires the active participation of specific host RBOHs, to induce ROS and cell death, thus leading to the establishment of disease. Based at least in part on these discoveries, the inventors disclose herein plant cells and plants modified to increase resistance to necrotrophs and methods of generating and using such plant cells and plants.

Plant Cells

In one aspect of the present invention, plant cells are provided. The plant cells may be modified to eliminate or reduce as compared to a control plant cell the NADPH oxidase activity or expression of one or more of the Group VI RBOHs in the plant cell, including but not limited to a RBOHB protein, a RBOHL protein, a RBOHP protein, a RBOHQ protein, or any combination thereof (collectively, as used herein, the "RBOH proteins"). Although the present inventors in the non-limiting Examples disclose silencing the expression of all four of these proteins in a plant or plant cell, they also show that overexpression of each of these proteins individually led to enhanced susceptibility to *S. sclerotiorum*. See, e.g., FIGS. 9A-9C. Based on this data, the present inventors conjecture that these proteins have at least partially redundant functions with respect to *S. sclerotiorum* susceptibility and thus eliminating or reducing the NADPH oxidase activity or expression of 1, 2, 3, or all 4 of these proteins may be sufficient to induce the necrotroph resistance and/or drought phenotypes disclosed herein. Notably, in the Examples, the expression of the four proteins was not eliminated, but instead the expression of each was reduced. The inventors believe that elimination of expression for example via genetic manipulation of only a single of the Group VI RBOH genes or a group of two, three or four will be sufficient to increase resistance to nematodes and increased tolerance of drought.

In some embodiments, the plant cells may be modified to eliminate or reduce as compared to a control plant cell the NADPH oxidase activity or expression of at least one, two, three, four, or more respiratory burst oxidase homolog (RBOH) protein(s) selected from the group consisting of SEQ ID NO: 1 (GmRBOHB), a variant or homolog of SEQ ID NO: 1 having at least 60%, 70%, 80%, 85%, 90%, 95%, 97%, 98% or 99% sequence identity to SEQ ID NO: 1, SEQ ID NO: 2 (GmRBOHL), a variant or homolog of SEQ ID NO: 2 having at least 60%, 70%, 80%, 85%, 90%, 95%, 97%, 98% or 99% sequence identity to SEQ ID NO: 2, SEQ ID NO: 3 (GmRBOHP), a variant or homolog of SEQ ID NO: 3 having at least 60%, 70%, 80%, 85%, 90%, 95%, 97%, 98% or 99% sequence identity to SEQ ID NO: 3, SEQ ID NO: 4(GmRBOHQ), and a variant or homolog of SEQ ID NO: 4 having at least 60%, 70%, 80%, 85%, 90%, 95%, 97%, 98% or 99% sequence identity to SEQ ID NO: 4.

In some embodiments, the NADPH oxidase activity or expression of every RBOH protein in the plant cell having at least 60%, 70%, 80%, 85%, 90%, 95%, 97%, 98% or 99% sequence identity to SEQ ID NO: 1, SEQ ID NO: 2, SEQ ID NO: 3, or SEQ ID NO: 4 is reduced or eliminated.

As used herein, the terms "protein" or "polypeptide" or "peptide" may be used interchangeably to refer to a polymer of amino acids. A "protein" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

SEQ ID NOs: 1-4 are RBOH proteins identified in *Glycine max* (soybeans) that may be used as reference sequences. SEQ ID NO: 1 is the protein sequence of the GmRBOHB protein. SEQ ID NO: 2 is the protein sequence of the GmRBOHL protein. SEQ ID NO: 3 is the protein sequence of the GmRBOHP protein. SEQ ID NO: 4 is the protein sequence of the GmRBOHQ protein. These proteins are similar to *Arabidopsis thaliana* RBOHB. Other RBOH proteins from other plants having homology to the Group VI RBOH proteins are also included.

The RBOH proteins disclosed herein may include "variants" of SEQ ID NOS: 1-4 that are found in other varieties of soybeans or in other varieties of beans/legumes in general. As used herein, a "variant" refers to a protein having an amino acid sequence that differs from a RBOH reference protein of SEQ ID NOs: 1-4. A variant may have one or more insertions, deletions, or substitutions of an amino acid residue relative to a reference molecule. For example, a RBOH protein variant may have one or more insertion, deletion, or substitution of at least one amino acid residue relative to the reference RBOH proteins (SEQ ID NOs: 1-4) disclosed herein. The RBOH proteins disclosed herein may include "homologs" of SEQ ID NOs: 1-4 that are found in other plant species besides soybean plants. A "homolog" may be a protein related to a second protein by descent from a common ancestral protein.

Regarding the RBOH proteins disclosed herein, the phrases "% sequence identity," "percent identity," or "% identity" refer to the percentage of residue matches between at least two amino acid sequences aligned using a standardized algorithm. Methods of amino acid sequence alignment are well-known in the art. A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that may be used to align a known amino acid sequence with other amino acids sequences from a variety of databases.

RBOH protein sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "deletion" in a RBOH protein refers to a change in the amino acid sequence resulting in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a RBOH protein refers to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant or homolog of a RBOH may have N-terminal insertions, C-terminal insertions, internal insertions, or any combination of N-terminal insertions, C-terminal insertions, and internal insertions.

As used herein, a "plant cell" may include any type of plant cell from any plant species. Suitable plants cells may include dicotyledonous plant cells or cells from broad leaf plants including, without limitation, a soybean plant cell, a common bean plant cell, or a leguminous plant cell. In some embodiments, the plant cell comprises a stem, root, or leaf cell. Plant cells also include plant callus or other plant tissues composed of plant cells.

The eliminated or reduced NADPH oxidase activity or expression of the RBOH protein is relative to a control plant cell. A "control plant cell" is a plant cell that has not been modified as described herein. Exemplary control plant cells may include those from a soybean variety or from a natural plant species for plant cells that are not soybean plant cells.

As used herein, "NADPH oxidase activity" refers to the ability of a RBOH protein to catalyze the conversion of $O_2$ to $O_2-$ or other reactive oxygen species (ROS) such as hydroxyl radicals or hydrogen peroxide. In some embodiments, the NADPH oxidase activity of the at least one RBOH protein is reduced by at least 30%, 40%, 50%, 55%, 60%, 65%, 70%, 75%, 80%, 85%, 90%, 95%, 97%, 98% or 99% as compared to a control plant cell. In some embodiments, the total NADPH oxidase activity of the at least one RBOH protein is reduced by at least 30%, 40%, 50%, 55%, 60%, 65%, 70%, 75%, 80%, 85%, 90%, 95%, 97%, 98% or 99% as compared to a control plant cell. As used herein, the "total NADPH oxidase activity" refers to the summation of NADPH oxidase activity for the RBOHB protein, RBOHL protein, RBOHP protein, and RBOHQ protein (or variants or homologs thereof) in a plant.

As used herein, the term "expression" may refer either to the levels of an RNA encoding a protein in a cell or the levels of the protein in a cell. In some embodiments, the expression of the at least one RBOH protein is reduced by at least 30%, 40%, 50%, 55%, 60%, 65%, 70%, 75%, 80%, 85%, 90%, 95%, 97%, 98% or 99% as compared to a control plant cell.

In some embodiments, the total expression of the at least one RBOH protein is reduced by at least 30%, 40%, 50%, 55%, 60%, 65%, 70%, 75%, 80%, 85%, 90%, 95%, 97%, 98% or 99% as compared to a control plant cell. As used herein, the "total expression" refers to the summation of the expression levels for the RBOHB protein, RBOHL protein, RBOHP protein, and RBOHQ protein (or variants or homologs thereof) in a plant.

The plant cells may be modified to eliminate or reduce as compared to a control plant cell the NADPH oxidase activity or expression of at least one of the RBOH proteins described herein. As used herein, the terms "modified" or "modifying" refer to using any laboratory methods available to those of skill in the art including, without limitation, genetic engineering techniques (i.e. CRISPR/Cas techniques or gene silencing technologies), traditional breeding/selection techniques, or forward genetic techniques to affect the NADPH oxidase activity or expression of a RBOH protein(s). It will be readily apparent to one of ordinary skill in the art that there a multiple potential ways to eliminate or reduce the NADPH oxidase activity or expression of a RBOHB protein, a RBOHL protein, a RBOHP protein, a RBOHQ protein or any combination thereof by modifying the gene encoding any one of these proteins by, for example, introducing targeted mutations, by modifying a mRNA (or levels thereof) encoding any one of these proteins using, for example, gene silencing techniques, or by inhibiting the RBOHB RBOHL, RBOHP, and/or RBOHQ proteins at the protein level.

In some embodiments, the plant cell may include a nucleic acid agent capable of downregulating an RNA transcript encoding the RBOH protein. Suitable nucleic acid agents may include, without limitation, a microRNA, an siRNA, an antisense RNA, or a plant viral vector. Suitable plant viral vectors may include, without limitation, a Bean pod mottle virus vector (BPMV), an Apple latent spherical virus vector (ALSV), and Pea early browning virus vector (PEBV).

The plant may also be modified to introduce a hypomorphic mutation or a null mutation in a polynucleotide (i.e., gene) encoding the RBOH protein. A "null mutation" is an alteration in a gene that results in a gene that completely lacks its normal function. The complete lack of function may be the result of the complete absence of a gene product (i.e., protein or RNA) being produced in a cell or may result from the expression of a non-functional protein. Similarly, a "hypomorphic mutation" is an alteration in a gene that results in a gene that has reduced activity. The reduced activity may be from a reduced level of expression of gene products (i.e., protein or RNA) from the gene or may result from the expression of a gene product (i.e. protein or RNA) that has reduced activity.

It will be readily apparent to those of skill in the art that a variety of null or hypomorphic mutations may be introduced (using, for example, CRISPR/Cas or other genome engineering techniques) into a polynucleotide encoding any one of the RBOH proteins described herein to arrive at embodiments of the present invention. For example, early stop codons may be introduced into the open reading frame of the gene encoding the RBOH protein, which would result in the expression of a shorter protein sequence completely lacking or having reduced activity. Alternatively or additionally, a person of ordinary skill may introduce alterations (i.e., substitutions or deletions) into the promoter of a gene encoding a RBOH protein described herein that result in little or no expression of the RBOH protein.

Still further modifications contemplated herein include mutations that impact one or more of the domains of the RBOH protein. As appreciated in the art, RBOH proteins possess cytosolic FAD- and NADPH-binding domains at their C-terminal region, and six conserved transmembrane helices. The third and fifth helices support, via key histidine residues, two heme groups, that are required for electron transfer across the plasma membrane. The N-terminal region contains variable numbers of calcium-binding EF-hand motifs and phosphorylation target sites that are important for their activity. It will be understood by those of skill in the art that alterations (i.e., mutations and/or deletions) could be made in any one or more of these domains that would be expected to eliminate or reduce the NADPH oxidase activity of the RBOH protein.

Figure 12:
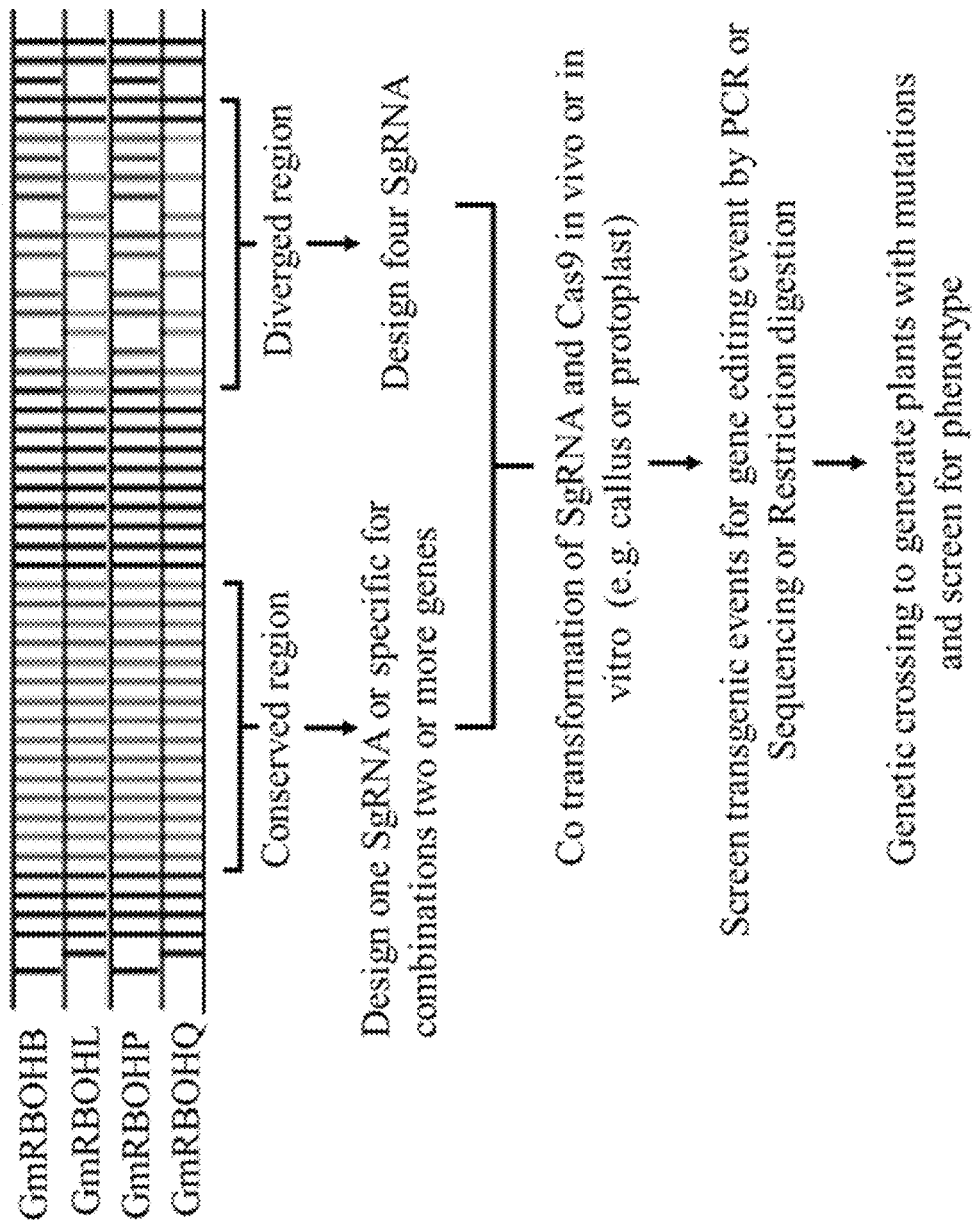
FIG. 12 shows the alignment of the four GMRBOH-VI genes and provides flow charts showing how the CRISPR-Cas system can be used to create constructs that can target all the four genes together, alone and in different combinations and permutations.

As exemplarily null or hypomorphic mutations that may be introduced into the genes encoding RBOH proteins described herein, in the Examples, the inventors contemplate that use CRISPR/Cas9 molecular tools where short homologous regions are sufficient for specific knock outs of the target genes See, e.g., T. B. Jacobs, P. R. LaFayette, R. J. Schmitz, W. A. Parrott, Targeted genome modifications in soybean with CRISPR/Cas9, *BMC Biotechnol.* 15 (2015) 16. As shown in FIG. 12, a skilled artisan will appreciate that constructs may be created that can target all the four genes together, alone and in different combinations and permutations.

Plants

In another aspect of the present invention, plants are provided. The plants may include any one of the plant cells described herein. The plants may include plants in which every cell of the plant is a plant cell modified as described herein. Alternatively, the plants may include plants in which only certain tissues within the plant include the plant cells described herein. For example, with respect to gene silencing techniques, it is contemplated that the plants may only have plant cells including a microRNA, an siRNA, an antisense RNA, or a plant viral vector in certain tissues of the plant using, for example, tissue-specific promoters.

As used herein, a "plant" includes any portion of the plant including, without limitation, a whole plant or a portion of a plant such as a part of a root, leaf, stem, seed, pod, flower, tissue plant germplasm, asexual propagate, or any progeny thereof. For example, a soybean plant refers to the whole soybean plant or portions thereof including, without limitation, the leaves, flowers, fruits, stems, roots, or otherwise. Suitable plants may include dicots or broad leaf plants including, without limitation, a soybean plant, a common bean plant, or a leguminous plant.

The plant may exhibit improved properties over a control plant. For example, the plant may have improved resistance to a necrotroph as compared to a control plant. Necrotroph resistance may be measured using assays known in the art. For example, in the non-limiting Examples, the inventors performed resistance assays to the necrotroph, *S. sclerotiorum*, in soybean plants. Soybean plants were infected with *S. sclerotiorum* using the cut petiole inoculation method (Hoffman, Diers et al. 2002).

As used herein, a "necrotroph" refers to an organism that kills the living cells of their hosts and then feeds on the resulting dead matter. Suitable necrotrophs may include, without limitation, *Sclerotinia sclerotiorum*.

The plant may have improved drought tolerance as compared to a control plant. Drought tolerance may be measured using methods known in art such as, for example, subjecting the plants to water-stress over a period of a certain number of days.

As used herein, a "control plant" is a plant that has not been modified as described herein. Exemplary control plant cells may include those from a soybean variety such as *Glycine max* or from a natural plant species for non-soybean plants.

Methods of Generation and Screening

In a further aspect of the present invention, methods of generating a plant having increased resistance to a necrotroph and/or drought as compared to a control plant are provided. The methods may include modifying at least one cell in the plant to eliminate or reduce as compared to a control plant cell the NADPH oxidase activity or expression of at least one, two, three, four, or more respiratory burst oxidase homolog (RBOH) protein(s) selected from the group consisting of SEQ ID NO: 1 (GmRBOHB), a variant or homolog of SEQ ID NO: 1 having at least 60%, 70%, 80%, 85%, 90%, 95%, 97%, 98% or 99% sequence identity to SEQ ID NO: 1, SEQ ID NO: 2 (GmRBOHL), a variant or homolog of SEQ ID NO: 2 having at least 60%, 70%, 80%, 85%, 90%, 95%, 97%, 98% or 99% sequence identity to SEQ ID NO: 2, SEQ ID NO: 3 (GmRBOHP), a variant or homolog of SEQ ID NO: 3 having at least 60%, 70%, 80%, 85%, 90%, 95%, 97%, 98% or 99% sequence identity to SEQ ID NO: 3, SEQ ID NO: 4(GmRBOHQ), and a variant or homolog of SEQ ID NO: 4 having at least 60%, 70%, 80%, 85%, 90%, 95%, 97%, 98% or 99% sequence identity to SEQ ID NO: 4. In some embodiments of the present methods, the NADPH oxidase activity or expression of every RBOH protein in the plant cell having at least 60%, 70%, 80%, 85%, 90%, 95%, 97%, 98% or 99% sequence identity to SEQ ID NO: 1, SEQ ID NO: 2, SEQ ID NO: 3, or SEQ ID NO: 4 is reduced or eliminated.

In some embodiments, the at least one cell in the plant is modified by introducing into the at least one cell a nucleic acid agent capable of downregulating an RNA transcript encoding the at least one RBOH protein. Suitable nucleic acid agents may include, without limitation, a microRNA, an siRNA, an antisense RNA, or a plant viral vector. Suitable plant viral vectors may include, without limitation, a Bean pod mottle virus vector (BPMV), an Apple latent spherical virus vector (ALSV), and Pea early browning virus vector (PEBV). In some embodiments, the at least one cell in the plant is modified by introducing into the at least one cell a hypomorphic or a null mutation in a polynucleotide encoding the at least one RBOH protein.

In a still further aspect, the present invention relates to methods of screening for a plant having increased resistance to a necrotroph and/or drought resistance as compared to a control plant. The methods may include a) generating a plurality of plant variants, and b) measuring in at least one cell of the plurality of plant variants the NADPH oxidase activity or expression of at least one, two, three, four, or more respiratory burst oxidase homolog (RBOH) protein(s) selected from the group consisting of SEQ ID NO: 1 (GmRBOHB), a variant or homolog of SEQ ID NO: 1 comprising at least 60%, 70%, 80%, 85%, 90%, 95%, 97%, 98% or 99% sequence identity to SEQ ID NO: 1, SEQ ID NO: 2 (GmRBOHL), a variant or homolog of SEQ ID NO: 2 comprising at least 60%, 70%, 80%, 85%, 90%, 95%, 97%, 98% or 99% sequence identity to SEQ ID NO: 2, SEQ ID NO: 3 (GmRBOHP), a variant or homolog of SEQ ID NO: 3 comprising at least 60%, 70%, 80%, 85%, 90%, 95%, 97%, 98% or 99% sequence identity to SEQ ID NO: 3, SEQ ID NO: 4(GmRBOHQ), and a variant or homolog of SEQ ID NO: 4 comprising at least 60%, 70%, 80%, 85%, 90%, 95%, 97%, 98% or 99% sequence identity to SEQ ID NO: 4. Optionally, the methods may further include c) selecting the plant variants wherein the NADPH oxidase activity or expression of the at least one RBOH protein is reduced or eliminated as compared to the NADPH oxidase activity or expression of the at least one RBOH protein in the control plant.

The plurality of plant variants may be generated using genetic methods known in the art including, without limitation, by crossing two plant lines or using mutagenesis with a mutagen. As used herein, a "mutagen" may refer to any radiation or substance that is capable of introducing mutations into a polynucleotide. Suitable mutagens may include, without limitation, chemical mutagens such as ethyl methanesulfonate (EMS) or N-nitro-N-methylurea (NMU) or radiation such as gamma-radiation or UV-radiation.

The NADPH oxidase activity of the RBOH protein may be measured using methods known in the art including, without limitation, enzyme assays measuring the conversion of $O_2$ to $O_2$— or other reactive oxygen species (ROS) such as hydroxyl radicals or hydrogen peroxide.

The expression of the RBOH protein may be measured using methods known in the art for measuring RNA levels or protein levels for a particular gene in the cell. Methods suitable for measuring the expression levels of a protein are known to those of skill in the art and include, without limitation, ELISA, immunofluorescence, FACS analysis, Western blot, magnetic immunoassays, and both antibody-based microarrays and non-antibody-based microarrays.

Methods suitable for measuring the expression levels of RNA are known to those of skill in the art and include, without limitation, northern blotting, in situ hybridization, RNAse protection assays, PCR-based methods, such as reverse transcription PCR(RT-PCR), including real time quantitative PCR and array-based methods. Representative methods for sequencing-based gene expression analysis include Serial Analysis of Gene Expression (SAGE) and gene expression analysis by massively parallel signature sequencing.

Methods of Using

In another aspect, the present invention relates to methods of using the plants described herein. The methods may include planting any one of the plants described herein in an area. The area may be at risk of drought and having below average precipitation or may include a necrotroph capable of infecting the plant.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—the Pathogenic Development of *Sclerotinia sclerotiorum* in Soybean Requires Specific Host NADPH Oxidases Introduction Plants continuously produce reactive oxygen species (ROS) as by-products of different metabolic pathways such as respiration and photosynthesis. In turn, these small molecules are constantly scavenged by the redox machinery of the cell. Therefore, a steady-state is maintained under normal physiological conditions (Alscher, Donahue et al. 1997, Apel and Hirt 2004, Tripathy and Oelmuller 2012). ROS can be toxic to various cell components, affecting proteins, lipids, and nucleic acids, when levels reach a certain threshold (Sharma, Jha et al. 2012). Thus, many studies have focused on the detrimental effect of ROS. However, increasing evidence suggests a more intricate role for these molecules that may function up or downstream of various signaling events (Baxter, Mittler et al. 2013). ROS can serve as secondary messengers as part of both inter and intracellular signaling, regulating key cellular processes (Mittler, Vanderauwera et al. 2011). In biotic stress responses, the regulation of the cellular redox state is now an important area of research, due to the strong correlation between ROS signaling and stress responses (Apel and Hirt 2004, Marino, Dunand et al. 2012). The hypersensitive response (HR), a form of programmed cell death (PCD), is perhaps one of the most studied forms of resistance responses mounted by plant tissues against invading pathogens. This response is accompanied by the release of superoxide anion (O2-) and hydrogen peroxide (H2O2) at the site of pathogen challenge, which is required for pathogen arrest and incompatibility. While the timing and magnitude may differ, ROS are also produced during compatible interactions contributing to successful infections by some pathogens (Williams, Kabbage et al, 2011, Gilbert and Wolpert 2013, Kabbage, Williams et al. 2013). Overall, it is clear that ROS play an important role in stress responses, and contribute to the outcome of many plant-microbe interactions.

One of the major sources of ROS in plants are plasma membrane-bound NADPH oxidases. They catalyze the conversion of O2 to O2-, which is further converted into other ROS, such as hydroxyl radicals and hydrogen peroxide (Sagi and Fluhr 2001). NADPH oxidases, also known as respiratory burst oxidase homologs (RBOHs), in plant and animal kingdoms possess cytosolic FAD- and NADPH-binding domains at their C-terminal region, and six conserved transmembrane helices. The third and fifth helices support, via key histidine residues, two heme groups, that are required for electron transfer across the plasma membrane (Lambeth 2004, Sagi and Fluhr 2006). The N-terminal region contains variable numbers of calcium-binding EF-hand motifs and phosphorylation target sites that are important for their activity (Kobayashi, Ohura et al. 2007, Glyan'ko and Ischenko 2010, Oda, Hashimoto et al. 2010, Kimura, Kaya et al. 2012).

RBOHs have been identified in various plant species including tomato, tobacco, *Arabidopsis, Medicago truncatula*, common bean, rice, and maize (Simon-Plas, Elmayan et al. 2002, Marino, Andrio et al. 2011, Wang, Li et al. 2013, Arthikala, Sanchez-Lopez et al. 2014, Li, Zhang et al. 2015). In *Arabidopsis*, they form a multigenic family comprised of 10 genes (AtRBOHA-J), and their activities have been implicated in various physiological events, including response to stress (Torres and Dangl 2005). AtRBOHD, the most highly expressed *Arabidopsis* RBOH, mediates many processes such as pathogen response, stomatal closure, systemic signaling in response to both abiotic and biotic stresses (Tones, Dangl et al. 2002, Kwak, Mori et al. 2003, Miller, Schlauch et al. 2009). AtRBOHD is also regulated by both Ca2+ dependent and independent pathways during immune responses (Dubiella, Seybold et al. 2013, Kadota, Sklenar et al. 2014, Kadota, Shirasu et al. 2015). AtRBOHF was shown to participate in ABA signal transduction and plays a key role in the interplay between intracellular oxidative stress and immune response to pathogens (Kwak, Mori et al. 2003, Chaouch, Queval et al. 2012, Marino, Dunand et al. 2012), and was implicated in non-host resistance to *Magnaporthe oryzae* in *Arabidopsis* (Nozaki, Kita et al. 2013). AtRBOHD and F are considered the main *Arabidopsis* isoforms associated with responses to pathogens. Other studies have noted the involvement of *Arabidopsis* RBOHs in developmental processes. AtRBOHC was shown to regulate root hair formation (Foreman, Demidchik et al. 2003), while AtRBOHB was essential for seed ripening and germination (Muller, Carstens et al. 2009). AtRBOHH and J modulate pollen tube growth and seed development (Kaya, Nakajima et al. 2014, Lassig, Gutermuth et al. 2014). Interestingly, a role for these proteins was also noted in connection with mutualistic interactions. In the model legume, *Medicago truncatula*, MtRBOHA, has been shown to be important for nodule functioning, silencing of MtRBOHA decreased nitrogen fixation activity in nodules and the modulation of genes encoding the microsymbiont nitrogenase (Marino, Andrio et al. 2011). In *Phaseolus vulgaris*, Arthikala et al. 2014, showed that the overexpression of PvRBOHB, a common bean NADPH oxidase gene, enhances symbiosome number, bacteroid size, and nitrogen fixation in nodules (Arthikala, Sanchez-Lopez et al. 2014). In toto, several functional studies have placed RBOHs at the center of ROS network regulation and associated biological processes in cells, thus demonstrating their importance to key metabolic functions in plants, including pathogen response.

*Sclerotinia sclerotiorum* is a cosmopolitan fungal pathogen that infects virtually all dicotyledonous plants (Bolton, Thomma et al. 2006, Kabbage, Yarden et al. 2015). It has been traditionally viewed as a prototypical necrotroph, but recent findings suggest that its pathogenic development may involve a brief biotrophic phase (Williams et al., 2011; Kabbage et al., 2013; Kabbage et al., 2015). *S. sclerotiorum* can cause considerable damage to crop plants and has proven difficult to control, with host resistance being inadequate. In soybean, this fungus causes *Sclerotinia* Stem Rot (SSR), also known as white mold disease. SSR can be a significant yield limiting disease, and yield losses greater than 10 million bushels (270 million kg) per year are common (Peltier, Bradley et al. 2012).

*S. sclerotiorum* is a prolific producer of cell wall degrading enzymes (e.g. pectinases, cellulases, hemicellulases), which facilitate plant cell wall degradation and host colonization (Amselem, Cuomo et al. 2011). In addition to its lytic repertoire, an important factor governing the pathogenic success of *S. sclerotiorum* is the secretion of the key virulence factor oxalic acid (OA). Mutants defective in OA production are poorly pathogenic and are unable to overcome host defenses (Williams, Kabbage et al. 2011, Kabbage, Williams et al. 2013, Liang, Liberti et al. 2015). OA was shown to contribute to pathogenesis in some ways that facilitate the colonization of the host plant, including the inhibition of host defenses (Williams, Kabbage et al. 2011), pH-mediated activation of CWDEs and the inhibition of autophagy (Kabbage, Williams et al. 2013). Importantly, OA induces apoptotic-like PCD, a process that is largely reliant on ROS (Kim et al., 2008). Thus, the regulation of ROS plays a critical role in the pathogenic success of *S. sclerotiorum*, particularly at the later stages of the infection process where ROS generation and tissue cell death culminates in the establishment of disease (Williams, Kabbage et al. 2011).

Due to the importance of RBOHs in ROS generation, we postulate that the upregulation of ROS and the ensuing cell death imposed by *S. sclerotiorum* requires host NADPH oxidases in soybean. Using a combination of bioinformatics tools, expression studies, and reverse genetic approaches, we show the key requirement of 4 soybean RBOHs (GmRBOHs), designated GmRBOH-VI, for SSR development. The silencing of this group resulted in decreased ROS levels, which coincided with enhanced resistance to *S. sclerotiorum*. Remarkably, these plants were also found to be drought tolerant, but the silencing of GmRBOH-VI affected root nodulation. Our results indicate that the pathogenic development of *S. sclerotiorum* in soybean requires the active participation of specific host RBOHs, to induce ROS and cell death, thus leading to the establishment of disease.

Results

Identification of the Soybean Respiratory Burst Oxidase Homolog Family

Figure 1B:
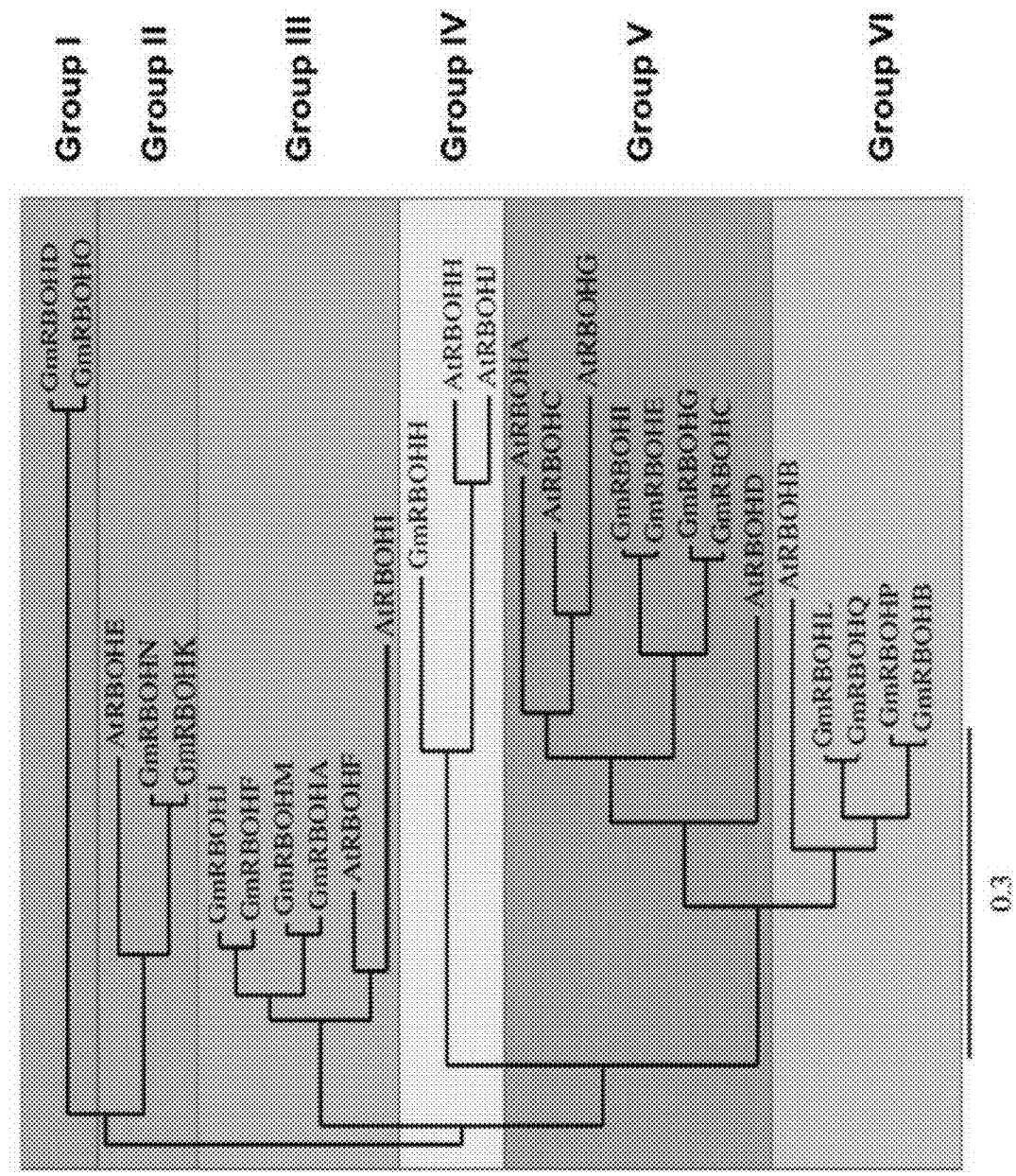

The *Arabidopsis* genome contains ten respiratory burst oxidase homologs (AtRBOHs) that have been widely studied and characterized (Marino, Dunand et al. 2012). We conducted Blastp searches against the soybean JGI Phytozome (Wm82.a2.v1) and NCBI databases using *Arabidopsis* protein sequences as reference queries and identified 17 soybean respiratory burst oxidase homologs (GmRBOHs). The identified GmRBOHs were named GmRBOHA-Q (Table 1), depending on the location in the soybean genome and the widely accepted nomenclature (Torres and Dangl 2005), and varied in size from 820 to 941 amino acids. Protein domain composition was analyzed using SMART alignment tool (smart.emblheidelberg.de/smart/set_mode.cgi?GENOMIC=1) and revealed that all the GmRBOHs have conserved NADPH oxidase, ferric reductase, FAD, and NAD binding domains (FIG. 1A). They also contain a variable number (0-2) of EF-hand motifs (FIG. 1A), which are known to play a key role in the calcium-dependent regulation of RBOHs (Wong, Pinontoan et al. 2007). We clustered the soybean RBOH genes into six groups of orthologs based on phylogenetic analysis with their *Arabidopsis* counterparts (FIG. 1B) AtRBOHs were distributed amongst all groups except group I (FIG. 1B). The soybean genes GmRBOHD and GmRBOHO belong to group I; GmRBOHN and GmRBOHG belong to group II; GmRBOHA, GmRBOHF, GmRBOH, and GmRBOHM belong to group III; GmRBOHH belongs to group IV; GmRBOHC, GmRBOHE, GmRBOHG and GmRBOHI belong to group V; and GmRBOHB, GmRBOHL, GmRBOHP, and GmRBOHQ belong to group VI. Our analysis predicts an expanded family of at least 17 genes in the soybean genome that encode RBOH proteins, none of which have been previously examined.

Spatial Expression Profile of Soybean RBOHs

Figure 2:
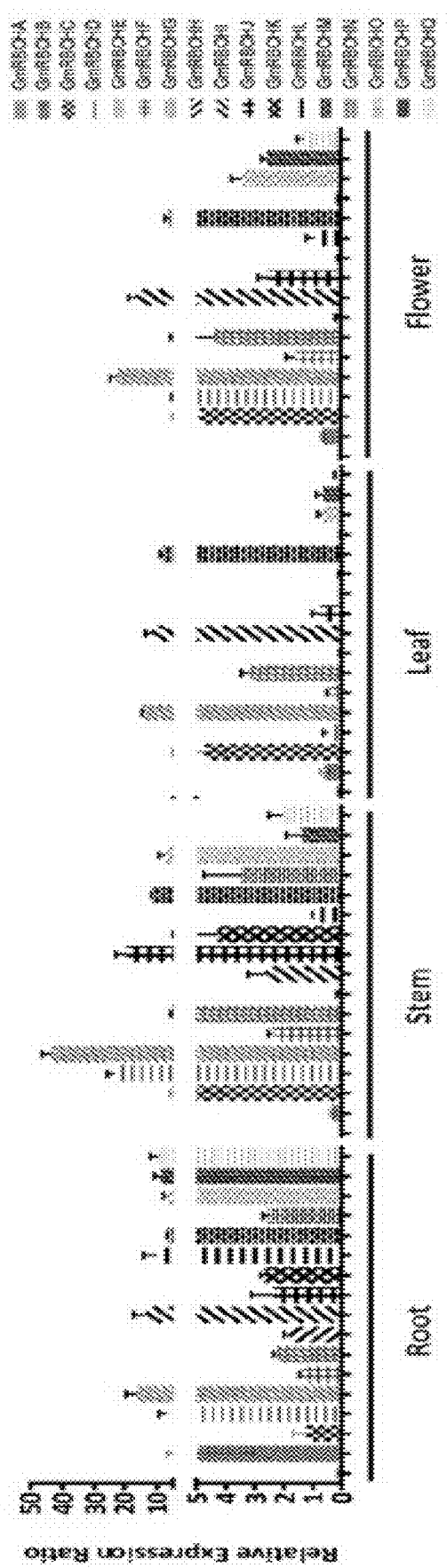
FIG. 2 shows the expression profile of GmRBOHs in different tissue. The mRNA transcript levels of all 17 GmRBOHs were determined by qRT_PCR in the root, stem, leaf and flower tissues. GmCons15 was used as internal control. All experiments were done with three independent biological repeats. Error bars represent the standard error (SE; n=3).

RBOH genes were reported to have tissue-specific expression patterns in plants, including *Arabidopsis*, tomato, and rice (Sagi and Fluhr 2006, Marino, Andrio et al. 2011, Wang, Li et al. 2013). For example, AtRBOHA-G and I are expressed in roots, AtRBOHH and J are pollen specific, while AtRBOHD and F are expressed throughout the plant (Sagi and Fluhr 2006). To determine tissue and organ-specific expression patterns of GmRBOHs, total RNA was extracted from roots, stems, flowers, and leaves of 4-week old soybean plants. RT-qPCR was performed using gene specific primers designed for each of the GmRBOHs (Table 2), and relative expression levels were calculated using Cons15, a CDPK-related protein kinase, as an internal control (Libault, Thibivilliers et al. 2008). Our analysis revealed that GmRBOHA is expressed at low levels in all tissues, while GmRBOHE and M are strongly and ubiquitously expressed throughout the plant (FIG. 2). GmRBOHB and GmRBOHL were specifically expressed in roots, while GmRBOHK and GmRBOHN appear to be mostly expressed in stems and roots. No flower or leaf-specific expression was detected, and the remainder of the GmRBOHs did not show any obvious organ-specific expression (FIG. 2). In accordance with what has been reported in other plant species, a variable expression pattern of GmRBOHs was detected depending on the tissue tested. The biological significance of such expression profiles needs further investigation.

TABLE 1

Soybean respiratory burst oxidase homologue (GmRboh) genes

| Name of gene | Locus ID In JGI Phytozyme (Wm82.a2.v1)[a] | NCBI Accession number[b] | Protein Size (Predicated, aa) | MW (KD) |
|---|---|---|---|---|
| GmRBOHA | Glyma.01G222700 | XP_003517484 | 927 | 105.94 |
| GmRBOHB | Glyma.03G236300 | XP_003521697 | 885 | 100.71 |
| GmRBOHC | Glyma.04G203200 | XP_003522455 | 928 | 104.86 |
| GmRBOHD | Glyma.05G021100 | XP_006579505 | 820 | 92.99 |
| GmRBOHE | Glyma.05G198700 | XP_014631288 | 898 | 100.98 |
| GmRBOHF | Glyma.05G212500 | XP_003525369 | 941 | 106.50 |
| GmRBOHG | Glyma.06G162300 | XP_003526909 | 941 | 105.56 |
| GmRBOHH | Glyma.07G130800 | XP_006583585 | 859 | 98.1 |
| GmRBOHI | Glyma.08G005900 | XP_003532261 | 888 | 100.49 |
| GmRBOHJ | Glyma.08G018900 | XP_003532995 | 941 | 106.70 |
| GmRBOHK | Glyma.09G073200 | XP_006587062 | 928 | 105.17 |
| GmRBOHL | Glyma.10G152200 | XP_003536070 | 825 | 93.72 |
| GmRBOHM | Glyma.11G020700 | XP_003538264 | 927 | 105.88 |
| GmRBOHN | Glyma.15G182000 | XP_014622948 | 935 | 105.90 |
| GmRBOHO | Glyma.17G078300 | XP_006600576 | 821 | 93.07 |
| GmRBOHP | Glyma.19G233900 | XP_003554649 | 887 | 101.12 |
| GmRBOHQ | Glyma.20G236200 | XP_003556516 | 889 | 101.23 |

[a] JGI Phytozyme (Wm82.a2.v1)
[b] NCBI Accession number

TABLE 2

List of primers used for Real Time PCR analysis and Overexpression construct

| Primers | Sequences (5'-3') |
|---|---|
| GmRBOHAF | CCTCCCTTAGCTGGGAAGAG (SEQ ID NO: 6) |
| GmRBOHAR | ATCCCGAGACCGACAAGTAGC (SEQ ID NO: 7) |
| GmRBOHBF | GGCCGTGCAATTGTTCATTC (SEQ ID NO: 8) |
| GmRBOHBR | TCCGACCATGTTTCCTGTTG (SEQ ID NO: 9) |
| GmRBOHCF | TACCTGCATCGCTCTCTCTT (SEQ ID NO: 10) |
| GmRBOHCR | CCTGAATTTCCCTCCTCCTA (SEQ ID NO: 11) |
| GmRBOHDF | CAGAAAGCCGGATACGAACA (SEQ ID NO: 12) |
| GmRBOHDR | TAAGAGTAGGGCTTCCACAG (SEQ ID NO: 13) |
| GmRBOHEF | GTGGACTCCTAAGAGCTGAATG (SEQ ID NO: 14) |
| GmRBOHER | TAGCAACACCACCTCATACTCC (SEQ ID NO: 15) |
| GmRBOHFF | TCTCAAGCGCACCGATTTCG (SEQ ID NO: 16) |
| GmRBOHFR | CTCAGCTCTCAACCTTCGTTTAC (SEQ ID NO: 17) |
| GmRBOHGF | ACCTGACAACGGCAAGAGT (SEQ ID NO: 18) |

TABLE 2-continued

List of primers used for
Real Time PCR analysis and
Overexpression construct

| Primers | Sequences (5'-3') |
|---|---|
| GmRBOHGR | CGTAAGGACCATCAATTAGAAC (SEQ ID NO: 19) |
| GmRBOHHF | ACCAAGGAATGGAACAAGAAGAC (SEQ ID NO: 20) |
| GmRBOHHR | CTCGGTGATCTTTACTCCTGAAA (SEQ ID NO: 21) |
| GmRBOHIF | AGTGGACTTCTAAGAGCTGAATG (SEQ ID NO: 22) |
| GmRBOHIR | CATACTCCCTGTAGTCTTGTGC (SEQ ID NO: 23) |
| GmRBOHJF | GCAGGAACAGGCTGAAGAATATG (SEQ ID NO: 24) |
| GmRBOHJR | GGCTGTAGTTAAGGTACGTGTCC (SEQ ID NO: 25) |
| GmRBOHKF | CACCAAGATTGCCGCTAAAC (SEQ ID NO: 26) |
| GmRBOHKR | CAGCTCCAGTGATAGCTTCT (SEQ ID NO: 27) |
| GmRBOHLF | GAAGGATCAGTTGCGTGAATTTTG (SEQ ID NO: 28) |
| GmRBOHLR | CTTCTTCATTAATTCGTCCATCGG (SEQ ID NO: 29) |
| GmRBOHMF | TACGTTGCACCTTTCGATGAT (SEQ ID NO: 30) |
| GmRBOHMR | CGCCATCCAAATACGTCTTAT (SEQ ID NO: 31) |
| GmRBOHNF | TCACCAAGATTGCCTCTAAACA (SEQ ID NO: 32) |
| GmRBOHNR | GTGGCTCAGCTCAAGTGATAG (SEQ ID NO: 33) |
| GmRBOHOF | AAAGCAGTCGGTTGTGGAGA (SEQ ID NO: 34) |
| GmRBOHOR | ATGTGTGTGTATTGGAGTCCTG (SEQ ID NO: 35) |
| GmRBOHPF | GGCATAACATCAGCTTCCATAAC (SEQ ID NO: 36) |
| GmRBOHPR | TTCTTCCGTCGGCATCTTTG (SEQ ID NO: 37) |
| GmRBOHQF | AGGATCAGCTGCGTGAATTTTG (SEQ ID NO: 38) |
| GmRBOHQR | TCGTCCATCAGCATCTTTGTC (SEQ ID NO: 39) |
| GmRBOHBattB1F | GGGGACAAGTTTGTACAAAAAAGCAGGCTTCAT GGAGATTCAATTGGAGCAG (SEQ ID NO: 40) |
| GmRBOHBattB2R | GGGGACCACTTTGTACAAGAAAGCTGGGTCAAA ATTCTCTTTATGAAAATCAAACTTG (SEQ ID NO: 41) |
| GmRBOHLattB1F | GGGGACAAGTTTGTACAAAAAAGCAGGCTTCAT GGTGGAGATCACGCTGGA (SEQ ID NO: 42) |
| GmRBOHLattB2R | GGGGACCACTTTGTACAAGAAAGCTGGGTCAAA ATTTTCTTTGTGAAAATCAAACTTGGTG (SEQ ID NO: 43) |
| GmRBOHPattB1F | GGGGACAAGTTTGTACAAAAAAGCAGGCTTCAT GGAGATTCAGTTAGAGC (SEQ ID NO: 44) |
| GmRBOHPattB2R | GGGGACCACTTTGTACAAGAAAGCTGGGTCAAA ATTCTCTTTATGAAAATCAAACTTGG (SEQ ID NO: 45) |
| GmRBOHQattB1F | GGGGACAAGTTTGTACAAAAAAGCAGGCTTCAT GGAGATTCACGAAAACCAAC (SEQ ID NO: 46) |
| GmRBOHQattB2R | GGGGACCACTTTGTACAAGAAAGCTGGGTCAAA ATTTTCTTTGTGAAAATCAAACTTG (SEQ ID NO: 47) |

Figure 3A:
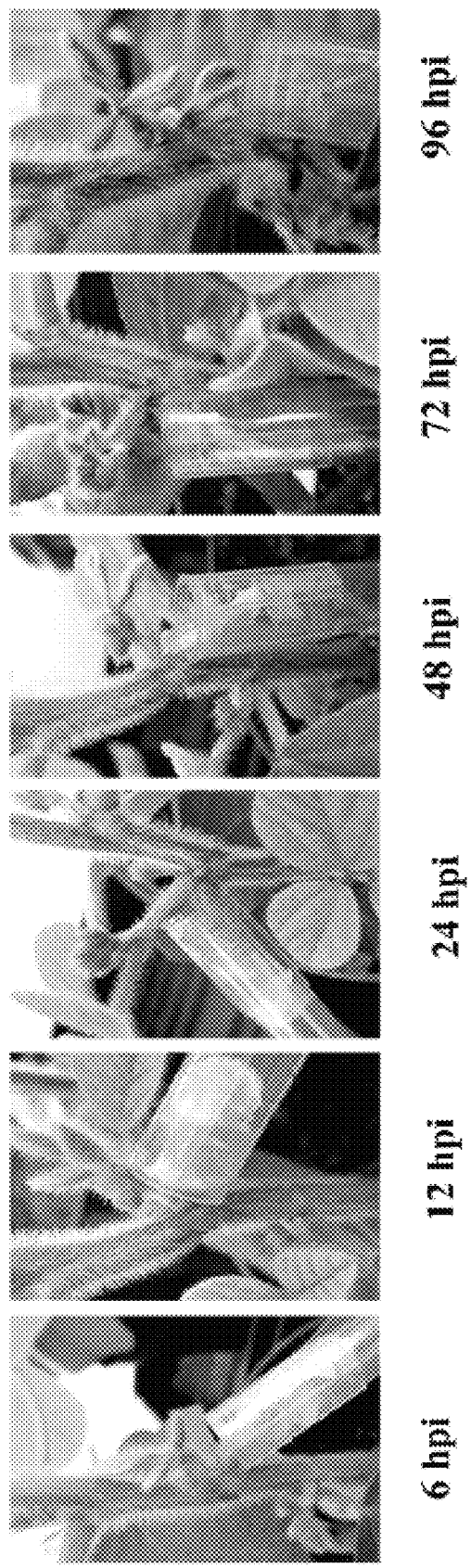
FIGS. 3A-3B show disease progression and expression profiles of GmRBOH-VI following infection with *S. sclerotiorum*.
Figure 3B:
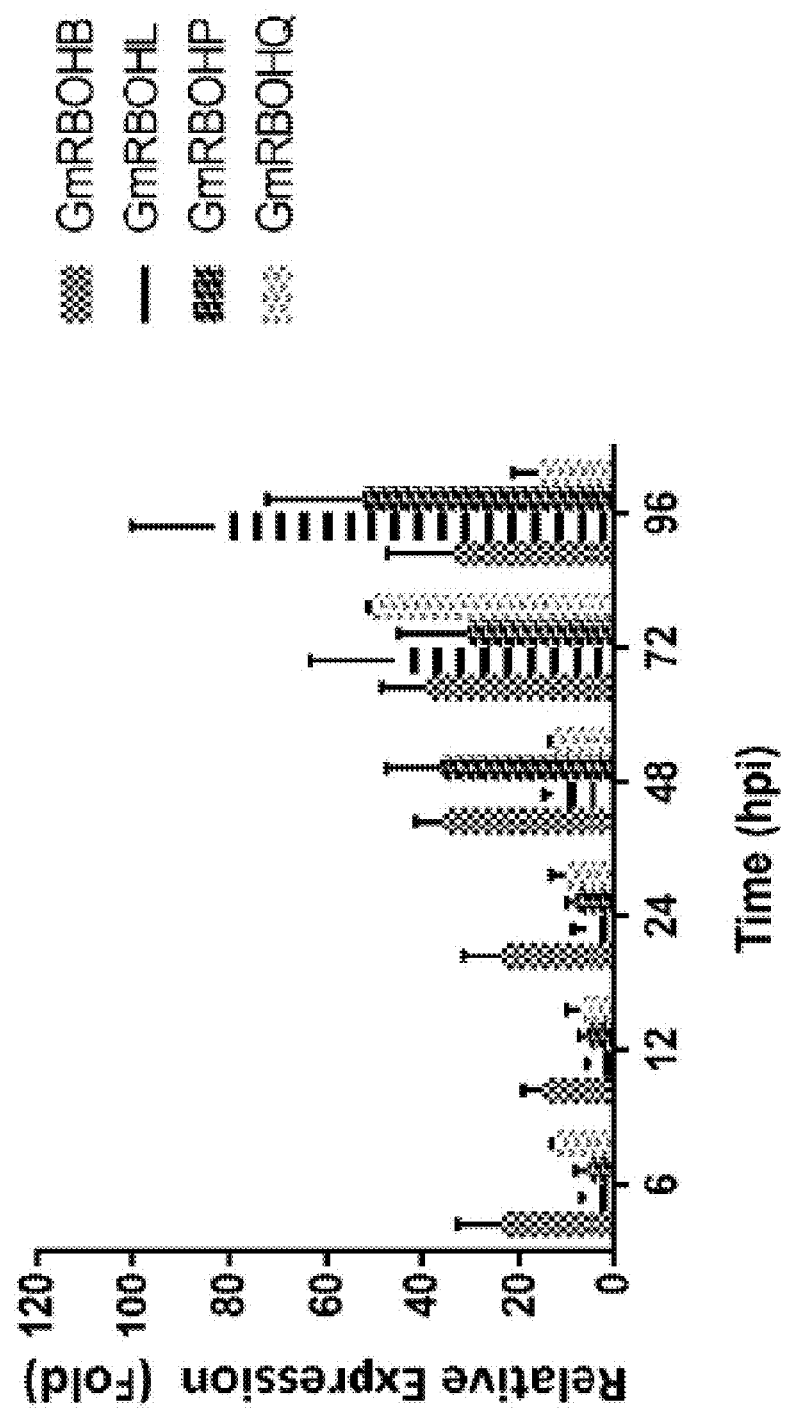
Figure 10:
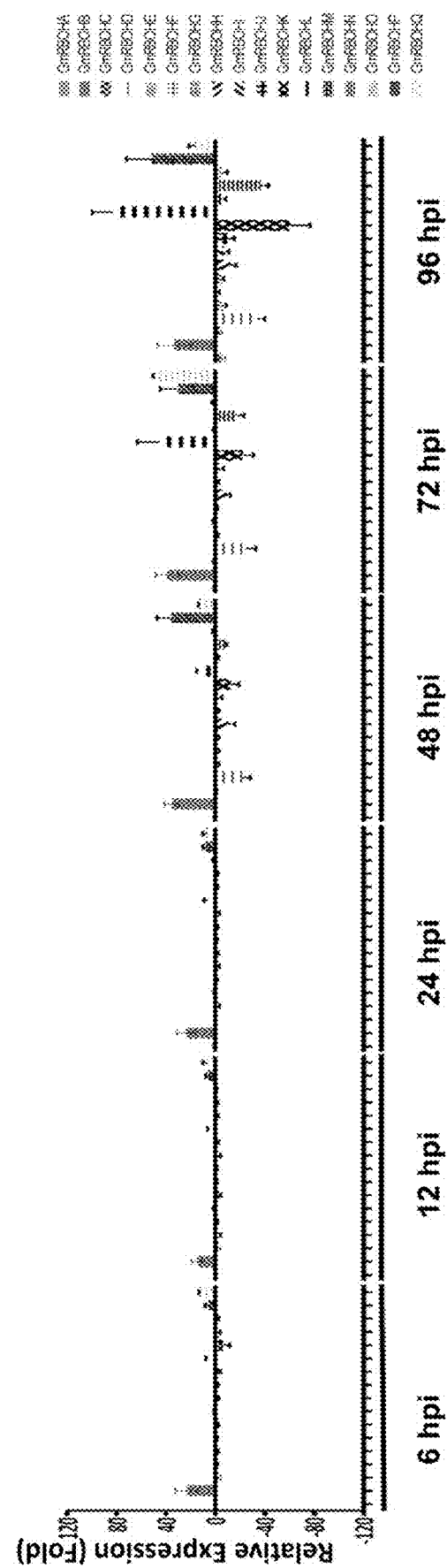
FIG. 10 shows expression analysis of all 17 GmRBOHs revealing that out of the six groups of GmRBOHs, group VI (GmRBOH-VI) was specifically and drastically induced during the time course. The expression of other GmRBOH members was either unaffected or down-regulated during the same time course.

Group VI GmRBOHs were Specifically Induced Following *S. sclerotiorum* Challenge ROS regulation plays a key role in the pathogenic development of *S. sclerotiorum*. One of the major sources of ROS in plants are plasma membrane-bound NADPH oxidases. Accordingly, we examined the expression pattern of GmRBOHs following *S. sclerotiorum* challenge in a time course experiment at 6, 12, 24, 48, 72 and 96 hours post-inoculation (hpi). Non-infected stem tissue served as control. Four-week-old soybean plants, 'Williams 82', were inoculated using the cut petiole inoculation technique (Peltier, Hatfield et al. 2009), where an agar plug containing actively growing mycelia of *S. sclerotiorum* is inserted at the base of a cut petiole. This inoculation method is designed to mimic field conditions, where fungal hyphae progress from germinating ascospores on the flower to the main stem of the soybean plant, to cause typical SSR symptoms. Disease symptoms first appeared at 48 hpi, by 96 hpi, significant cell death could be seen on the inoculated stem (FIG. 3A). Our expression analysis of all 17 GmRBOHs (FIG. 10) revealed that out of the six groups of GmRBOHs (FIG. 1B), group VI (GmRBOH-VI) was specifically and drastically induced during the time course (FIG. 3B). While GmRBOHB transcript abundance increased more than 20 fold as early as six hpi, peak expression of all four members of this group coincided with the later stages of infection (48-96 hpi) and development of disease symptoms (FIG. 3A). GmRBOHL (100 fold increase) and P (50 fold increase) were the most highly expressed at 96 hpi compared to uninfected controls. The expression of other GmRBOH members was either unaffected or down-regulated during the same time course (FIG. 10). Our results suggest that GmRBOH-VI members may be required by *S. sclerotiorum* for successful host colonization and SSR disease development.

Figure 4A:
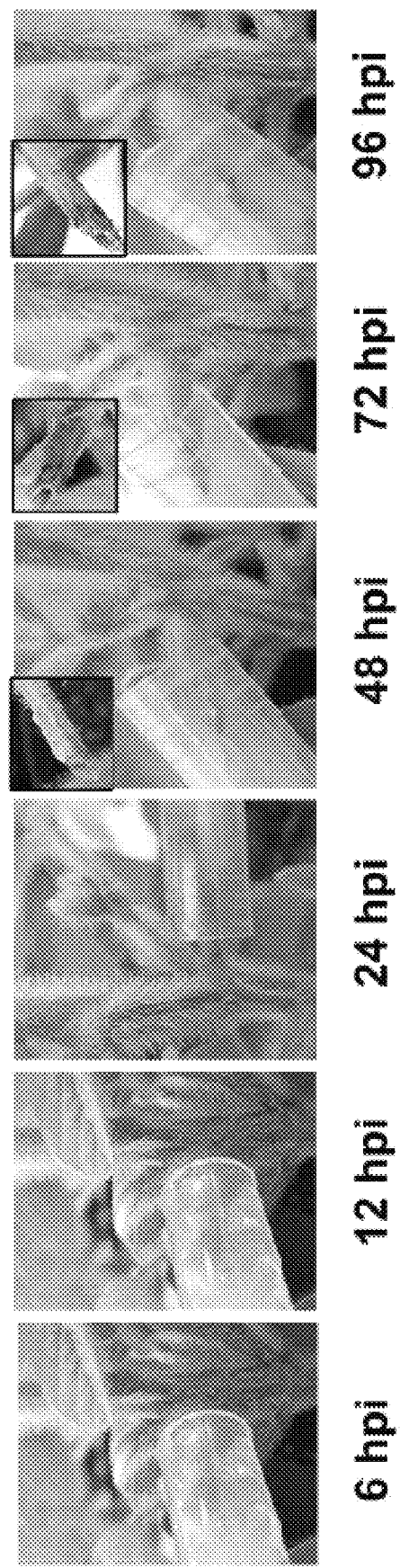
FIGS. 4A-4B shows disease progression and expression profile of GmRBOH-VI following inoculation with an OA deficient (A2) strain of *S. sclerotiorum*.
Figure 4B:
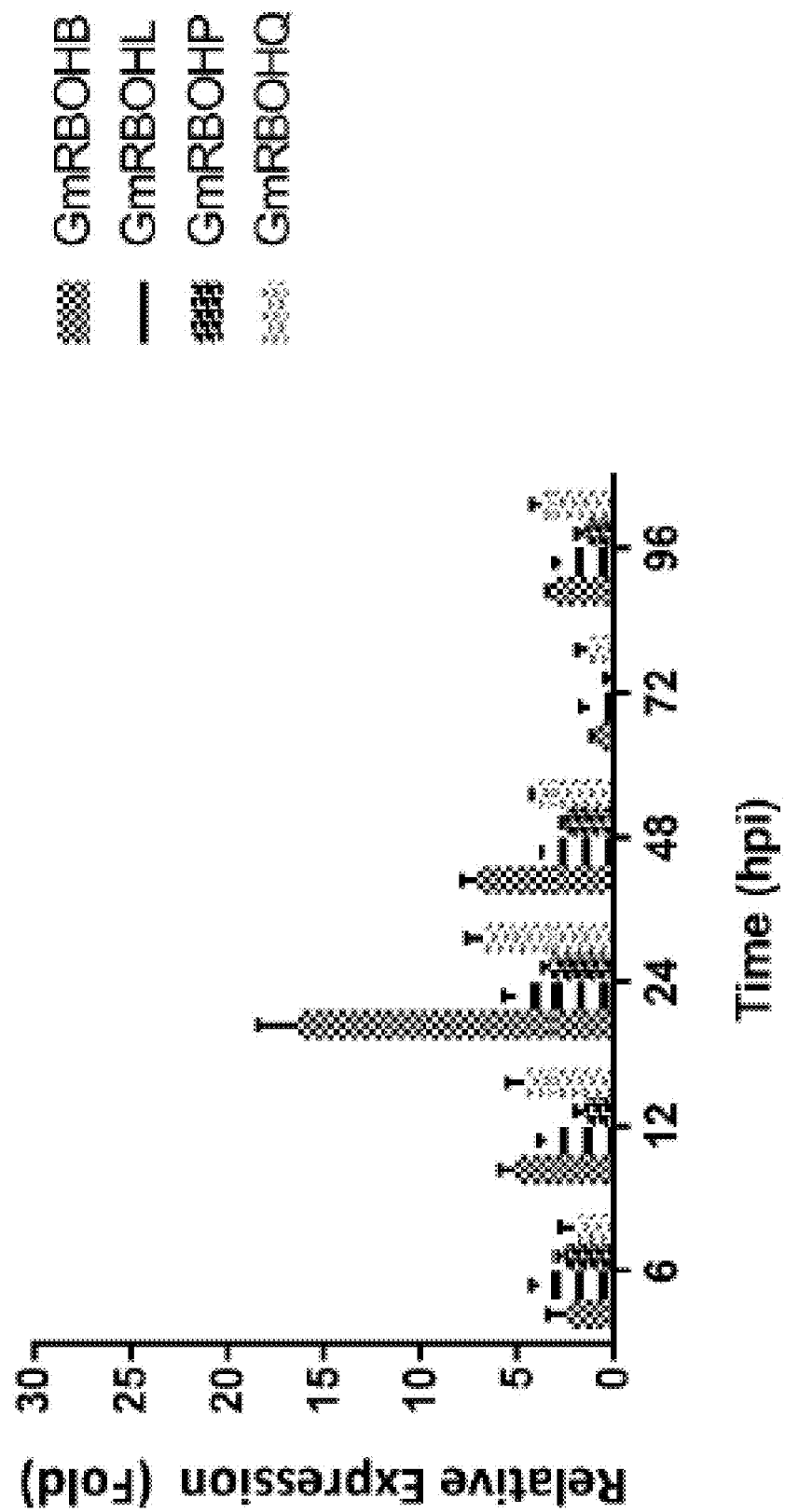

Oxalic acid (OA) is considered a key pathogenicity factor for *S. sclerotiorum*. Via OA secretion, this fungus can provoke an increase in ROS levels within the host, leading to apoptotic-like cell death and disease development (Kim et al., 2008; Williams et al., 2011). OA deficient mutants are unable to up-regulate host ROS levels and are largely non-pathogenic (Williams et al., 2011; Kabbage et al., 2013, Liang et al. 2015). Accordingly, we asked whether the previously studied OA-deficient mutant strain (A2) can alter the expression profile of GmRBOH-VI similar to the wild type strain. We examined the expression pattern of GmRBOHVI following A2 challenge using the same time course described for the wild-type strain (FIG. 4A). Expression analysis revealed this OA-deficient mutant was unable to induce the expression of GmRBOH-VI to wild-type levels, and the contrast between the two strains was particularly evident in the later stages of the infection process (48-96 hpi, FIG. 4B). Thus, our results suggest that in the absence of OA, S. sclerotiorum is unable to induce the expression of host RBOHs, increase ROS levels, and trigger cell death that is required for disease establishment.

Figure 11:
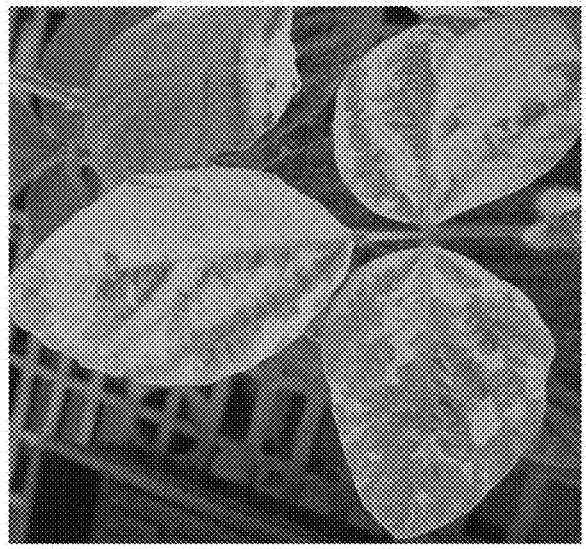
FIG. 11 shows an evaluation of the efficacy of our VIGS system in Traff by silencing the soybean phytoene desaturase (GmPDS), a gene involved in carotenoid biosynthesis, and obtaining consistent photo-bleaching of the host plants.
Figure 11:
Figure 11:

Silencing of GmRBOH-VI Leads to Enhanced Resistance to S. sclerotiorum in an ROSdependent Manner Our expression analysis showed that soybean RBOH-VI expression is significantly induced during the pathogenic development of S. sclerotiorum. We propose that these host genes may be required by the fungus for successful tissue colonization. Virus-induced gene silencing (VIGS) using Bean pod mottle virus (BPMV) (Zhang et al. 2010; Zhang et al, 2013), was employed to knock down the expression of GmRBOH-VI. This BPMV VIGS system was originally developed using the soybean variety Williams 82 due to its susceptibility to this virus. However, BPMV-infected Williams 82 plants showed strong resistance to S. sclerotiorum, making this variety unsuitable for our VIGS studies. We screened a large pool of soybean varieties and identified the variety Traff, which has shown better tolerance to BPMV but maintained a predictable response to S. sclerotiorum (data not shown). To evaluate the efficacy of our VIGS system in Traff, we silenced the soybean phytoene desaturase (GmPDS), a gene involved in carotenoid biosynthesis, and obtained consistent photo-bleaching of the host plants (FIG. 11).

Figure 5B:
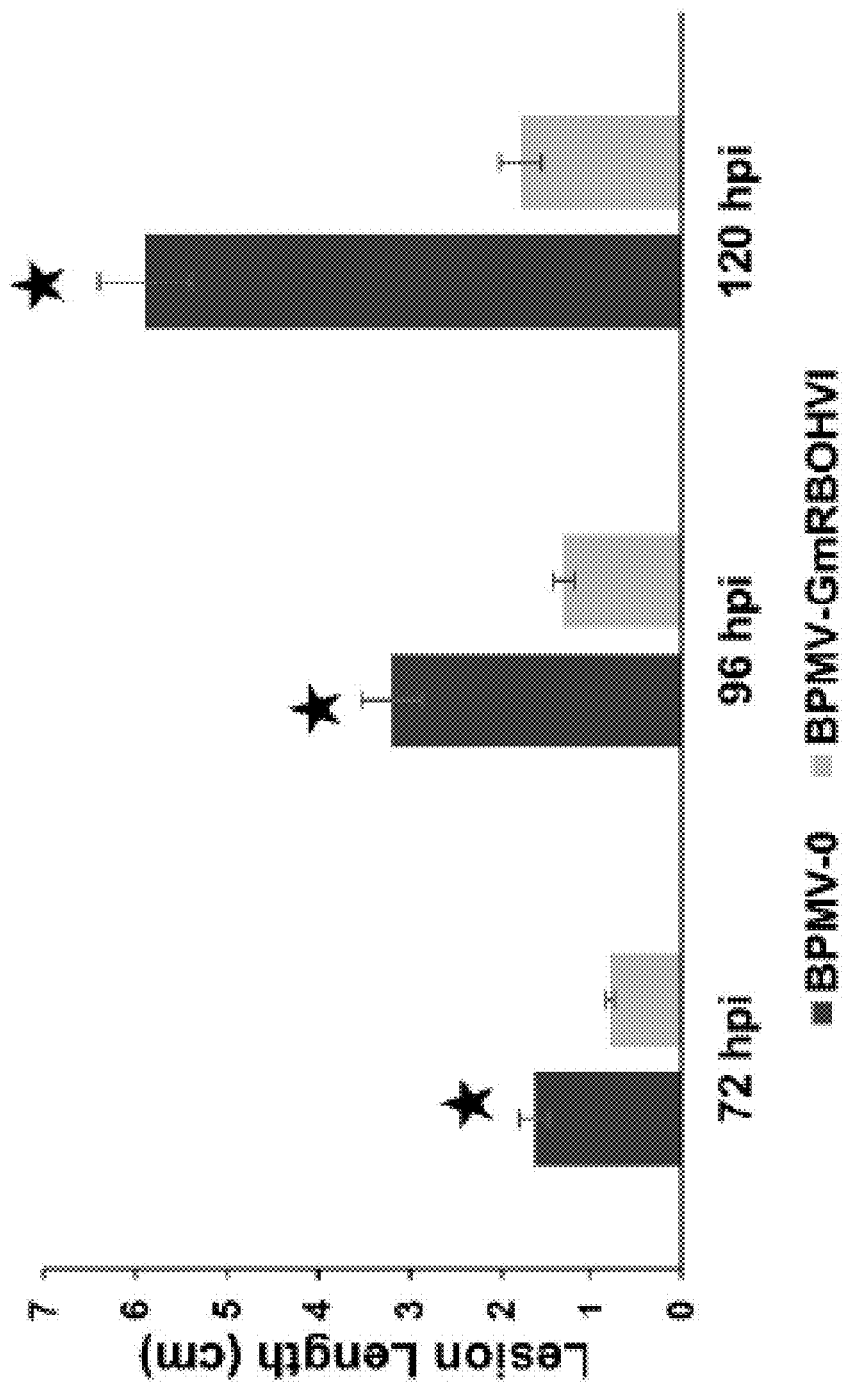
Figure 5C:
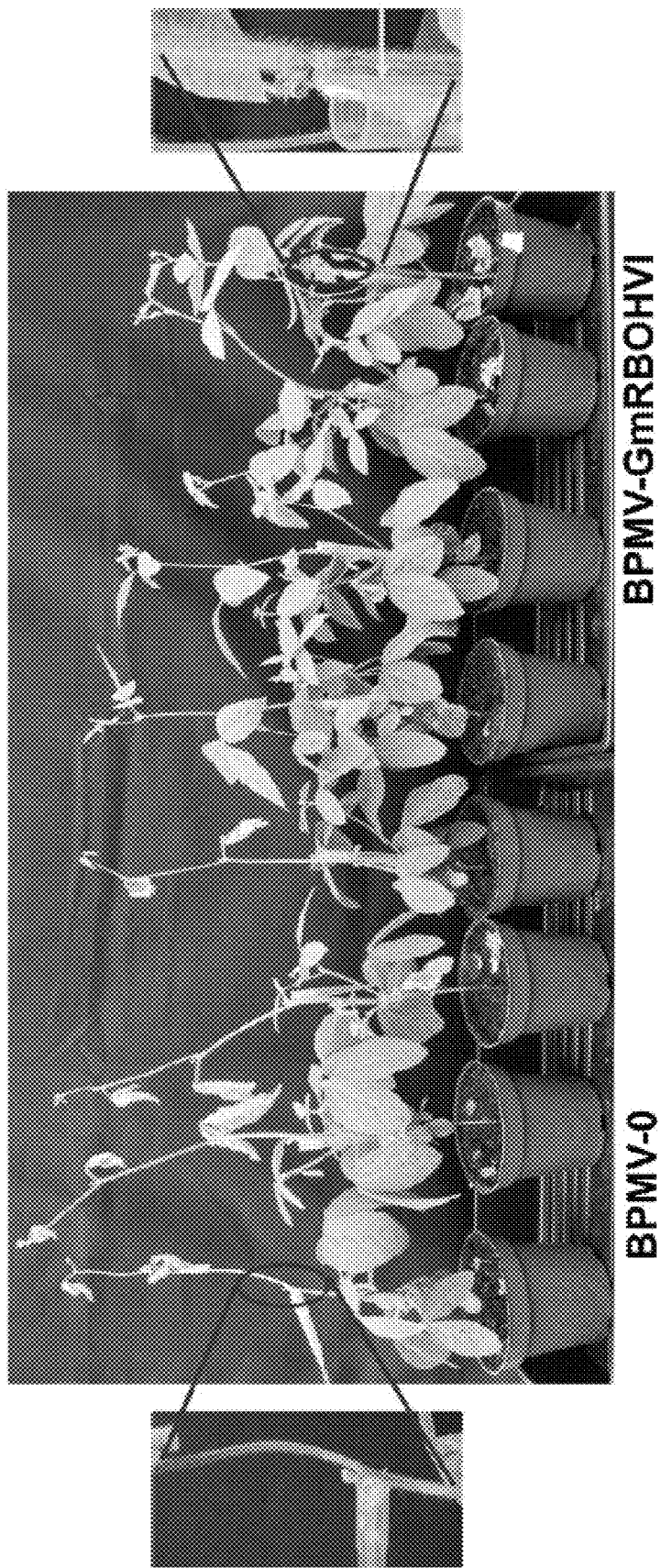

Due to strong sequence similarities among RBOH-VI group members, we were unable to silence these genes individually despite numerous attempts. Thus, a single BPMV silencing construct (pBPMV-GmRBOH-VI) was designed to target all four members. The silencing efficiency of pBPMV-GmRBOH-VI was determined in Traff by RT-qPCR and compared to empty vector control (pBPMV-0). Expression of target genes; GmRBOHB, GmRBOHL, GmRBOHP, and GmRBOHQ was significantly decreased, and we were able to achieve a 45 to 65% reduction in transcript levels compared to expression of these genes in empty vector control (FIG. 5A). GmRBOH-VI silenced soybean plants were then evaluated for their response to S. sclerotiorum challenge, three biological replicates with eight plants each were used. The cut petiole inoculation method was employed as previously described. Five days following S. sclerotiorum inoculation BPMV-0 soybean plants showed typical SSR symptoms and began to wilt. In contrast, GmRBOH-VI silenced plants did not show any wilting symptoms (FIGS. 5A-5C). In GmRBOH-VI silenced plants, lesion development was arrested shortly after reaching the main stem, and a red/dark discoloration was apparent at the edge of the lesion (FIG. 5B). Lesion length was quantified in both empty vector control and GmRBOH-VI silenced plants (FIG. 5C). Overall, these results suggest that silencing of GmRBOH-VI genes leads to enhance resistance in soybean against S. sclerotiorum infection, and suggest that this pathogen requires their activity to achieve pathogenic success.

Figure 6:
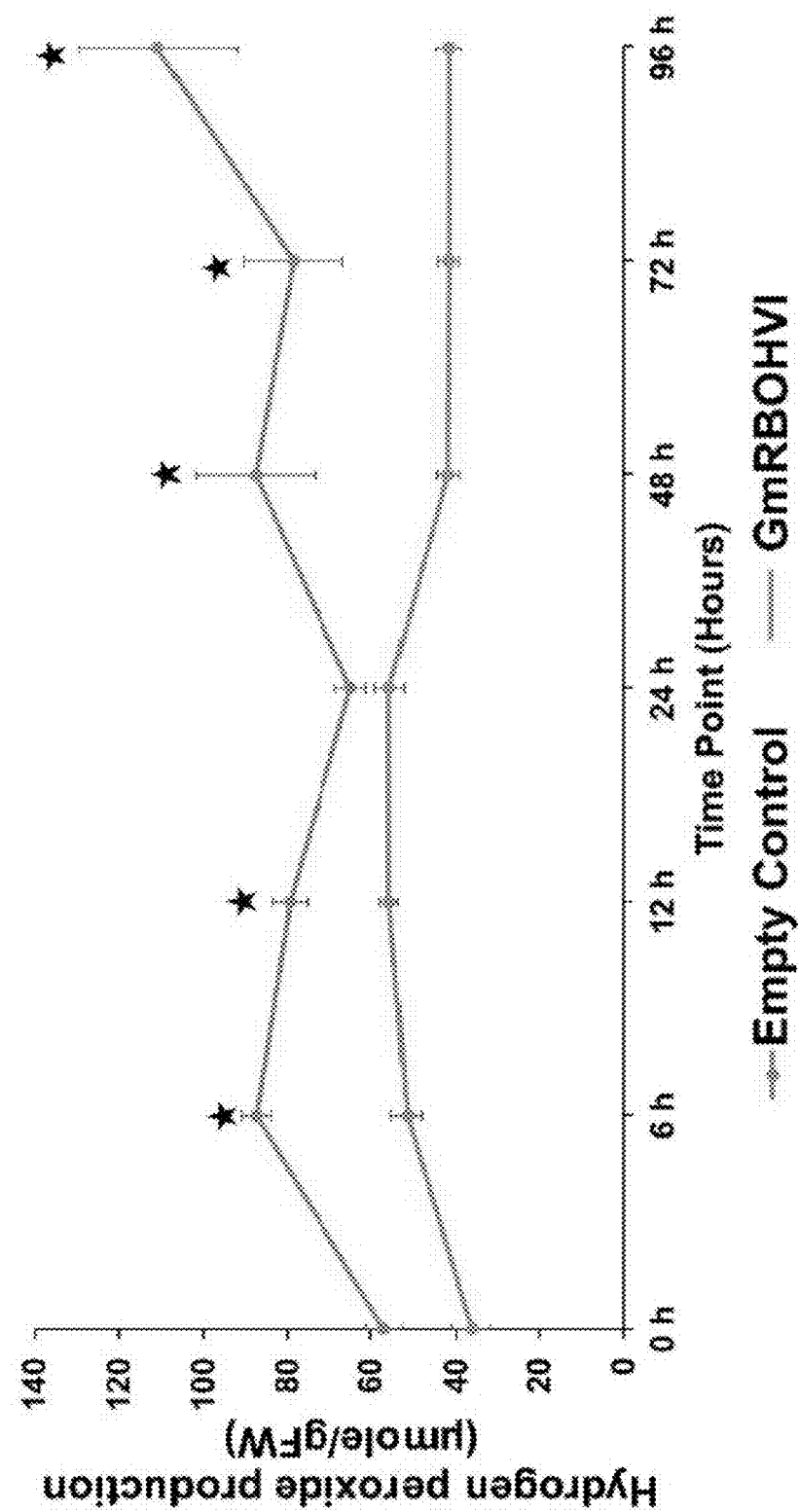
FIG. 6 shows the silencing of GmRBOH-VI coincides with reduced $H_2O_2$ production. $H_2O_2$ was quantified in infected and non-infected soybean stem tissue using the potassium iodide (KI) spectrophotometric method. Mean and SEM are shown (n=6) and expressed on the basis of stem fresh weight. * indicate significant differences at p<0.05.

RBOHs catalyze the conversion of O2 to O2-, which is further converted into other reactive oxygen molecules, including H2O2. We determined $H_2O_2$ levels in GmRBOH-VIsilenced and empty vector control plants challenged with S. sclerotiorum, using the potassium iodide (KI) method as previously described (Alexieva, Sergiev et al. 2001). Three biological replications, and four plants per replication were evaluated in a time course experiment (6, 12, 24, 48, 72 and 96 hpi). Our data indicated that GmRBOH-VI-silenced plants produce significantly less H2O2 compared to empty vector control plants (FIG. 6). In BPMV-0 control plants, H2O2 production increases in two phases. In the first phase, an increase in H2O2 levels is seen as early as six hpi. This is followed by a decrease until 24 hpi, where H2O2 levels once again increase continuously until 96 hpi as disease symptoms develop. At 96 hpi, as much as three times more H2O2 is produced in BPMV-0 compared to GmRBOH-VI-silenced plants (FIG. 6). Overall, our results show that S. sclerotiorum induces ROS levels in soybean as part of its pathogenic development, a process that is reliant on host RBOHs.

GmRBOH-VI Silenced Soybean Plants are Drought Tolerant

Figure 7A:
FIGS. 7A-7D show that knocking down expression of GmRBOH-VI leads to increased drought tolerance. Plants are shown before drought stress (FIG. 7A), seven days (FIG. 7B) and ten days (FIG. 7C) after water deprivation.
Figure 7B:
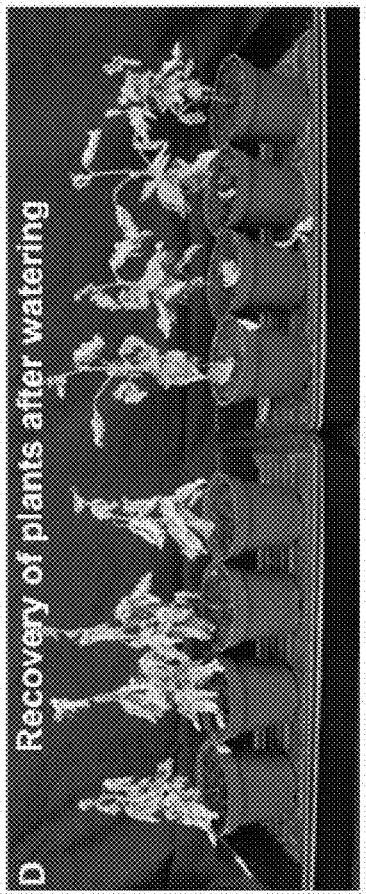
Figure 7C:
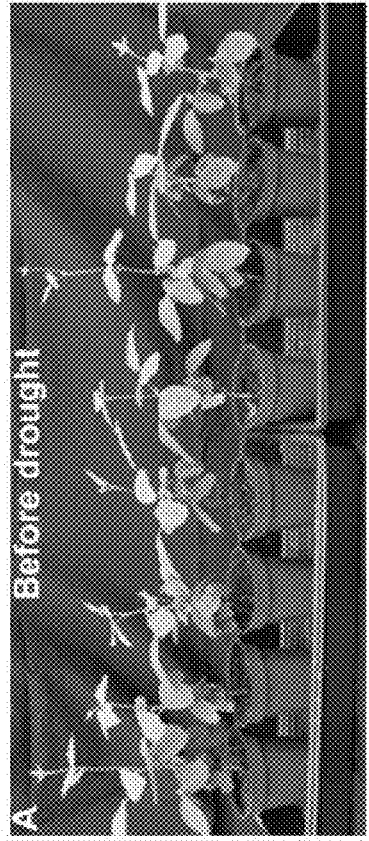
Figure 7D:
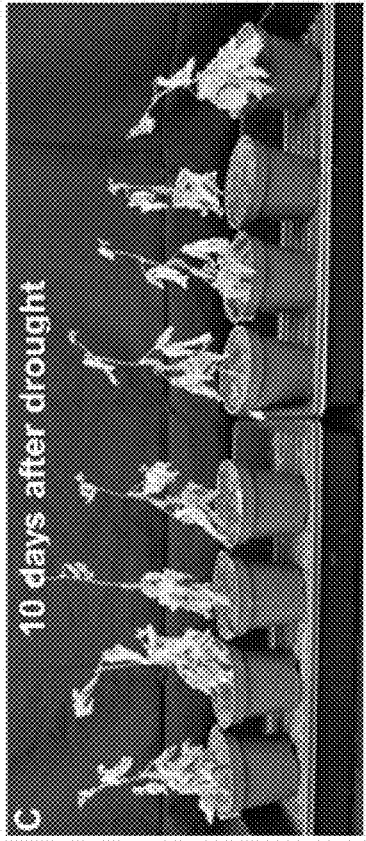

A role of RBOH genes in response to ROS-inducing insults has been reported, including in response to drought and salinity treatments (Lin, Zhang et al. 2009, Cheng, Xu et al. 2013, Wang, Li et al. 2013, Wang, Zhang et al. 2016). Drought is an important yield-limiting stress in soybean production, as such, we analyzed the effect of GmRBOH-VI silencing under water stress conditions. GmRBOH-VI-silenced plants and BPMV-0 inoculated plants were subjected to drought by depriving plants of water for ten days, after which watering was resumed. After a water deprivation period of 7 days, BPMV-0 inoculated plants showed severe wilting symptoms while GmRRBOH-VI-silenced plants maintained turgor (FIG. 7B). At ten days, GmRBOH VIsilenced plants also started to wilt (FIG. 7C). However, after watering was resumed, we observed that GmRBOH-VI-silenced plants recovered, while BPMV-0 inoculated plants did not. These results suggest that knocking down expression of GmRBOH-VI leads to increased drought tolerance, possibly by limiting oxidative damage and ultimately death of the plant imposed by elevated ROS levels during this stress.

Silencing of GmRBOH-VI Affects Soybean Nodulation

Previous studies have indicated the role of RBOHs in plant-legume symbioses. Knocking down the expression of MtRBOHA, negatively affected nodule formation in *Medicago truncatula* (Marino, Andrio et al. 2011). Work of Arthikala et al. 2014, showed that overexpression of PvRBOHB, in *Phaseolus vulgaris*, enhances symbiosome number, bacteroid size, and nitrogen fixation in nodules (Arthikala, Sanchez-Lopez et al. 2014).

Figure 8A:
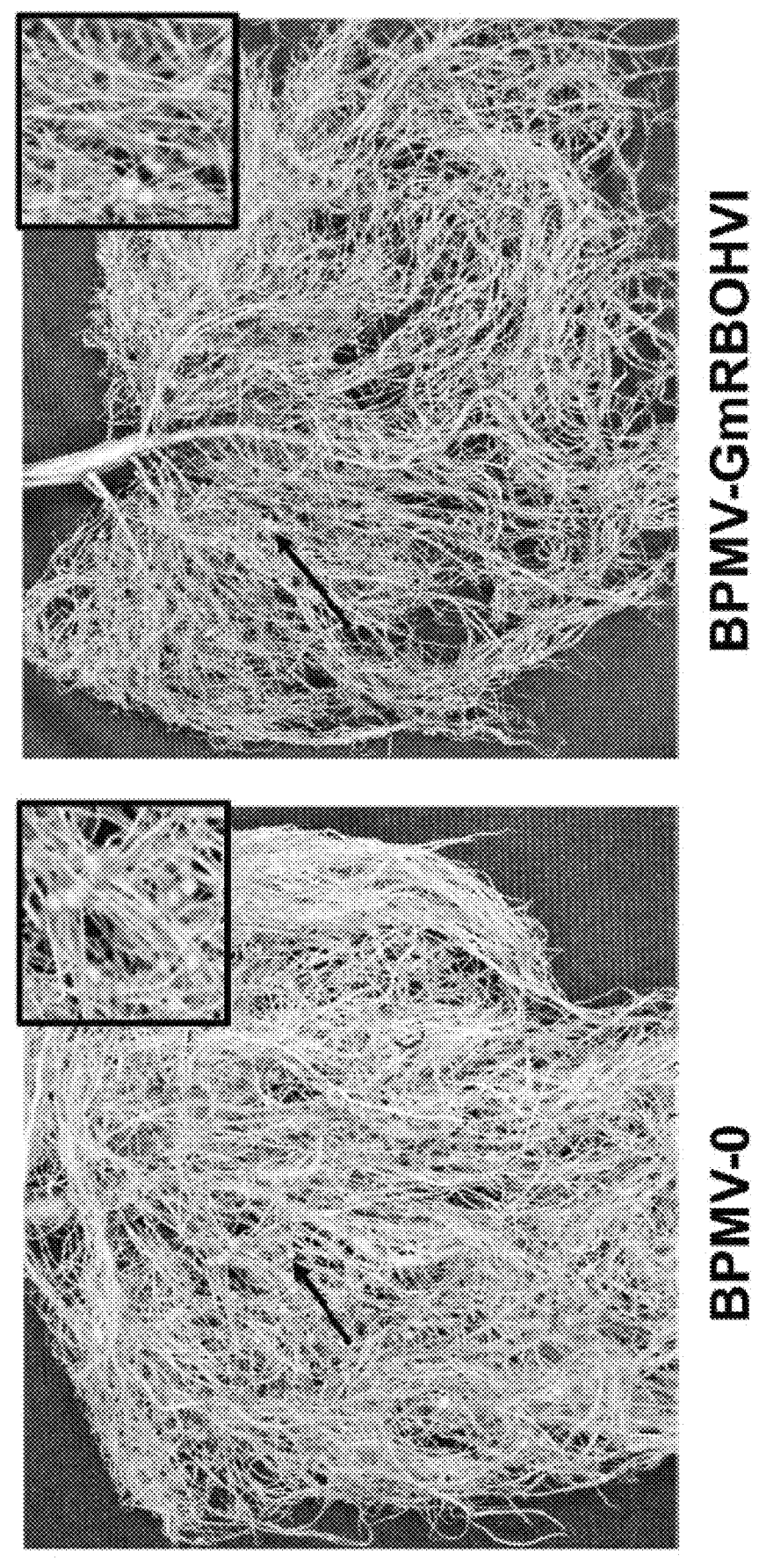

To determine the effect of GmRBOH-VI silencing on nodulation, we conducted nodulation assays in GmRBOH-VI-silenced and BPMV-0 control plants. Ten-day-old soybean plants were inoculated with the pBPMV-GmRBOH-VI and the control empty vector pBPMV-0. Control and GmRBOH-VI-silenced plants were then inoculated with *Bradyrhizobium diazoefficiens* USDA110, and nodules were counted 12 days post inoculation. A significant reduction in nodule numbers (P-value=0.04) was observed in GmRBOH-VI-silenced plants compared to controls. GmRBOH-VI-silenced plants produced on an average 69 nodules/plant, whereas the control produced 123 nodules/plant (FIG. 8B), representing approximately 50% reduction in nodule formation. We did not find any differences in the structure or shape of nodules between the treatments. This result indicates that knocking down expression of GmRBOH-VI leads to significant decrease in soybean nodulation.

Transient Overexpression of GmRBOH-VI in *Nicotiana benthamiana* Leads to Increased Susceptibility to *S. sclerotiorum*

Figure 9A:
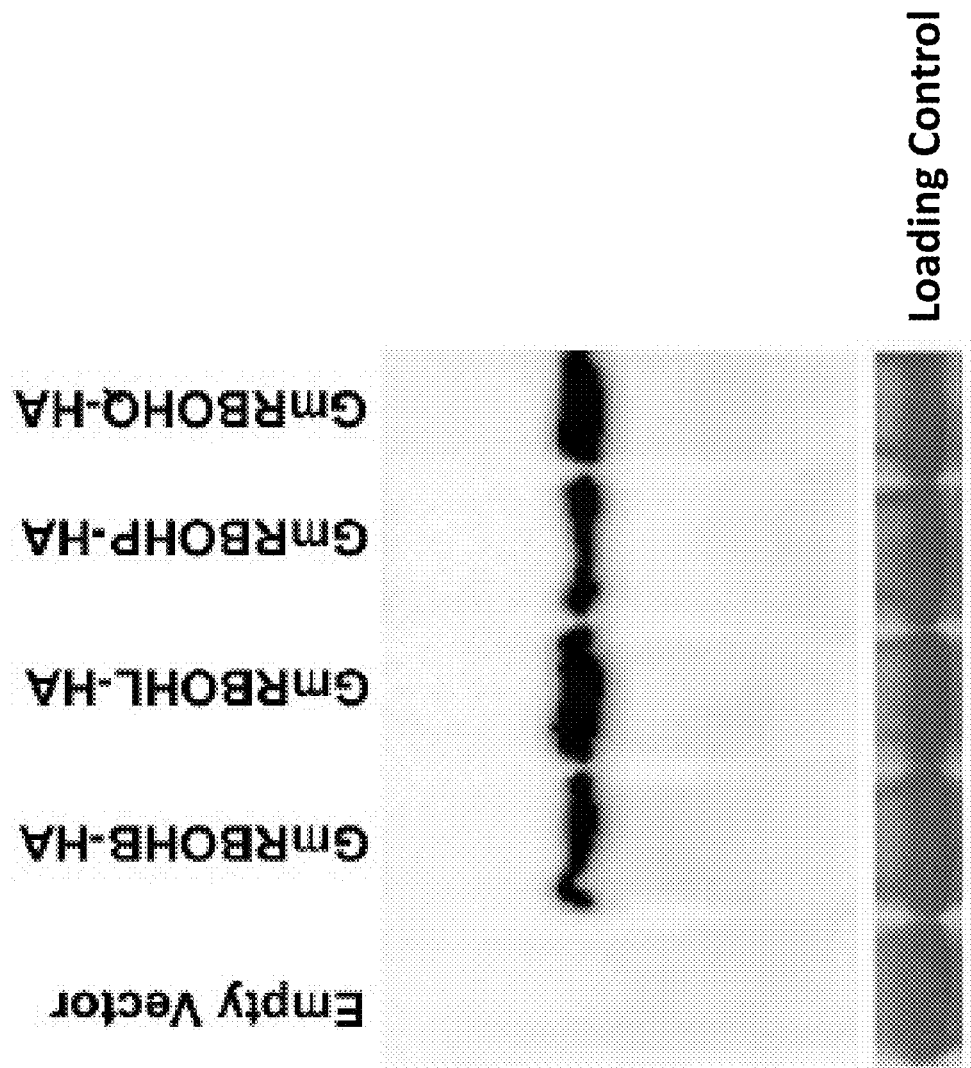
FIGS. 9A-9C show that transient overexpression of GmRBOHVI in *Nicotiana benthamiana* leads to enhanced susceptibility to *S. sclerotiorum*.
Figure 9B:
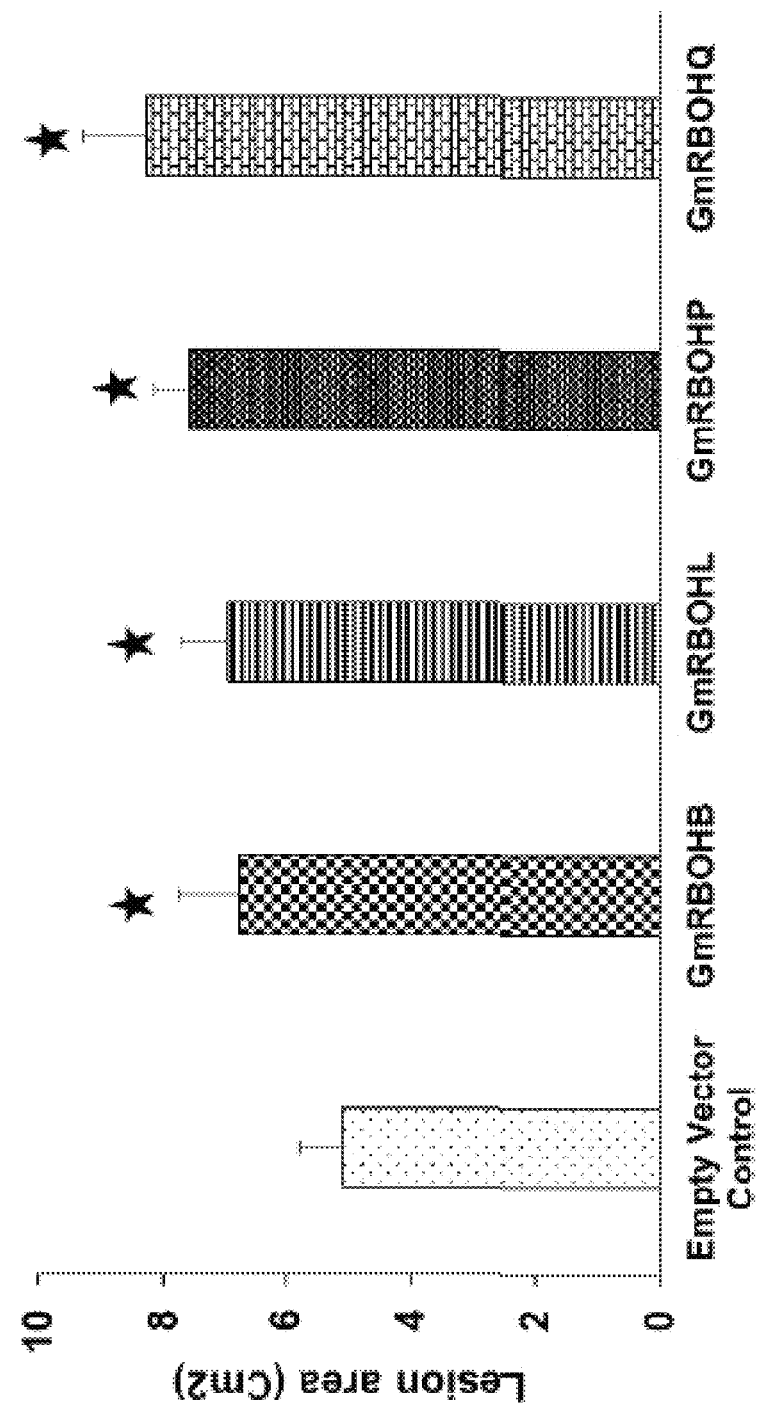
Figure 9C:
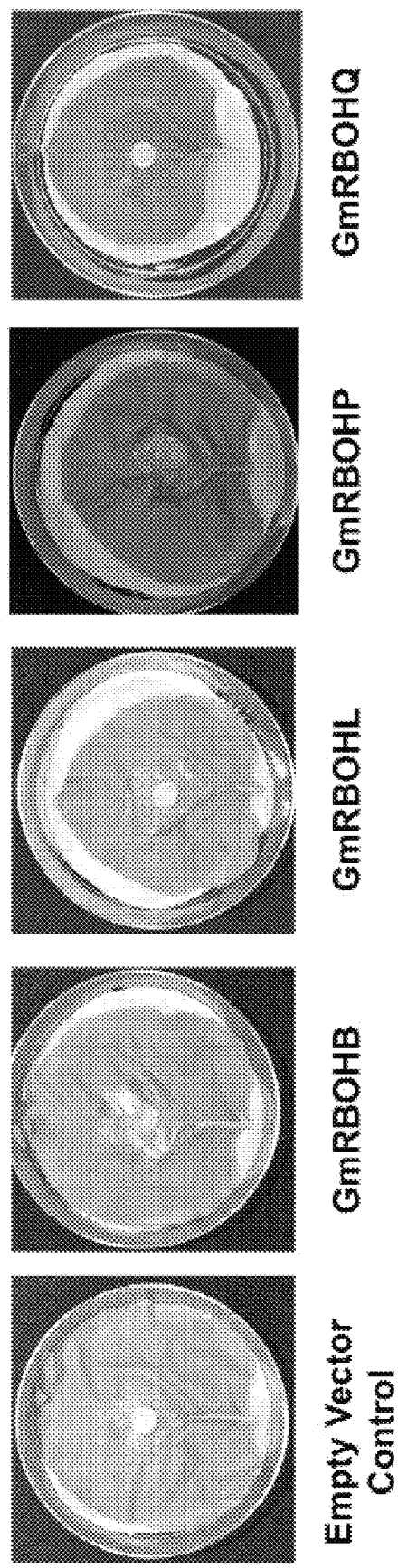

Considering our enhanced resistance phenotype observed in GmRBOH-VI silenced soybean in response to *S. sclerotiorum*, we reasoned that the overexpression of these genes might facilitate fungal growth and colonization. Transient assays are difficult to perform in soybean; so we opted to use *N. benthamiana* leaves to perform transient overexpression. Human influenza hemagglutinin (HA) tagged GmRRBOH-VI were cloned into an *Agrobacterium* compatible vector downstream of a 35S promoter, and bacterial cells were infiltrated into *N. benthamiana* leaves. The presence of RBOH proteins was detected via immunoblots, using anti-HA antibody (FIG. 9A). At 24 hours post agro-infiltration, detached leaves of *N. benthamiana* were challenged with agar plugs containing actively growing mycelia of *S. sclerotiorum*. The overexpression of GmRBOHB, GmRBOHL, GmRBOHP and GmRBOHQ in *N. benthamiana* enhanced disease development to varying levels and resulted in approximately 40%-60% increase in lesion area compared to empty vector control leaves (FIGS. 9B and 9C). These data suggest that overexpression of GmRRBOH-VI leads to increased susceptibility *S. sclerotiorum* infection in *N. benthamiana*, and further confirm their positive role in the pathogenic development of *S. sclerotiorum*.

Discussion

The cosmopolitan fungal pathogen *Sclerotinia sclerotiorum* can modulate host defenses and subvert plant programmed cell death (PCD) pathways to achieve pathogenic success. Indeed, *S. sclerotiorum* induces a cell-death regime in the host plant that displays apoptotic features (e.g. DNA laddering), and the expression of anti-apoptotic genes in plants prevents disease development (Kim et al., 2008; Kabbage et al., 2013). This pathogen makes efficient use of a simple dicarboxylic acid, oxalic acid (OA), to commandeer a range of host processes that include the elicitation of PCD. It is believed that the timely induction of cell death during host colonization provides nutrients that are for the benefit of the pathogen. Emerging evidence suggests that reactive oxygen species (ROS) play a key role in this process (Kim et al., 2008, Williams et al., 2011). ROS are known intermediaries of PCD responses, and function as signaling molecules during pathogen development and pathogen-host interactions (Torres et al., 2006; Erental et al., 2008). We examined the underlying mechanisms of ROS generation in soybean (*Glycine max*) in response to *S. sclerotiorum* by identifying the soybean respiratory burst oxidase homolog (GmRBOH) family, and characterizing its role in this pathogenic system. This study was prompted by previous observations indicating that one of the major sources of ROS in plants under pathogen attack are plasma membrane-bound RBOH proteins, and that host redox regulation is important to *S. sclerotiorum* pathogenicity (Williams et al., 2011). Several lines of evidence are consistent with the following conclusions: 1) A group of GmRBOH (GmRBOH-VI) genes is specifically induced following *S. sclerotiorum* challenge in soybean. 2) GmRBOH-VI induction may be reliant on the presence of the fungal secreted OA in the infection court, as OA-deficient mutants are unable to induce GmRBOH expression and are nonpathogenic. 3) The silencing of GmRBOH-VI leads to enhanced resistance to *S. sclerotiorum* and other ROS inducing insults. 4) GmRBOH-VI silencing and disease resistance coincide with a marked decrease in ROS levels in the host plant. Therefore, *S. sclerotiorum* appears to co-opt the soybean ROS machinery to its benefit, by modulating the expression of host RBOHs. These genes provide a potential target for the generation of SSR resistant soybean lines.

Several studies demonstrated the role of ROS production in plant immunity, and other plant processes, including abiotic stress responses, growth, and development. RBOHs play a key role in ROS generation, and different RBOHs may control different plant processes as previously reported (Torres and Dangl, 2005; Kadota et al., 2015). In plant immunity, ROS are proposed to function as antimicrobial molecules, in plant cell wall reinforcement, and as secondary messengers to activate additional defense responses. The implication of host RBOHs is well documented in defense responses, including HR-PCD and PAMP-triggered defenses following pathogen recognition. In *Arabidopsis*, the two principal isoforms associated with pathogen response are AtRBOHD and F. AtRBOHD, affects many processes, including lignification, cell death control, stomatal closure, systemic signaling in response to both abiotic, and biotic stresses (Torres, Dangl et al. 2002, Kwak, Mori et al. 2003, Miller, Schlauch et al. 2009). AtRBOHD is also regulated by both Ca2+-dependent and independent pathways during immune responses (Dubiella, Seybold et al. 2013, Kadota, Sklenar et al. 2014, Kadota, Shirasu et al. 2015). AtRBOHF and D have been shown to have redundant functions, since many of the observed phenotypes are enhanced in the Atrbohd and f double mutants (Kwak, Mori et al. 2003, Chaouch, Queval et al. 2012, Marino, Dunand et al. 2012). While significant progress has been made in our understanding of RBOH function in response to pathogens, many of these studies, however, have largely focused on biotrophic or hemibiotrophic pathogens.

While NADPH oxidase activity and ROS production typically correlate with successful disease resistance responses against invading biotrophic pathogens, ROS may be advantageous to pathogens with predominantly necrotrophic lifestyles, such as *S. sclerotiorum*, that require dead host tissue. As stated above, PCD is essential for *S. sclerotiorum* pathogenicity, a process that requires ROS generation. Our results show that a group of soybean RBOH genes (GmRBOH-VI) are specifically induced following *S. sclerotiorum* challenge, with peak expression at the later stages of the infection process. Silencing of GmRBOH-VI leads to markedly decreased ROS production and enhanced resistance to this pathogen. Thus, *S. sclerotiorum* may induce ROS production to its advantage by increasing RBOH activity. In accordance, necrotrophs were proposed to stimulate ROS production in host tissue to induce cell death and facilitate infection (Marino et al., 2012). This was further supported by results in *Arabidopsis* showing that ROS levels correlated positively with the growth of *Botrytis cinerea*, a close relative of *S. sclerotiorum*, but negatively with the growth of hemibiotrophic pathogen *Pseudomonas syringae* (Govrin and Levine 2000). Increased resistance to another necrotrophic fungus, *Alternaria brassicicola*, was also observed in rbohD mutants in *Arabidopsis* (Pogany et al., 2009). Surprisingly, the silencing RBOHB (SlRBOHB) in tomato led to increased susceptibility to *B. cinerea*, and its overexpression in *N. benthamiana* enhanced resistance to the same necrotrophic pathogen (Li et al., 2015). Although it is difficult to explain these contradicting results, it is, however, conceivable that similar pathogens may trigger different responses in a particular host. For example, *S. sclerotiorum* and *B. cinerea* are taxonomically closely related pathogens, but important differences in developmental and pathogenic features have been noted (Amselem et al., 2011). One of these differences is OA production, the requirement of which differs for the two pathogens depending on the host (Xu et al. 2015, Stefanato, Abou-Mansour et al. 2008). Thus, such disparities may provoke different host responses. Alternatively, the involvement of different RBOH genes, and the timing of RBOH activity and ROS generation may also be key to the outcome of a given host-microbe interaction. It should also be noted that RBOH activity is regulated by complex signaling events involving Ca2+-based regulation, pattern recognition receptor (PRR) complexes, and Rac GTPase (Kadota et al., 2015). Therefore, despite this common mechanism by which ROS are produced, RBOHs are at the crossroads of a complex network of signals, thus explaining the variable outcomes observed under different situations.

How *S. sclerotiorum* co-opts host ROS/RBOH machinery is an important question. It is reasonable to speculate that the key pathogenicity factor OA, plays a role in this interaction. In this study, we show that GmRBOH-VI induction requires OA in the infection court, and that OAdeficient mutants are unable to up-regulate GmRBOH-VI expression and are non-pathogenic. We note that the lack of GmRBOH-VI transcript induction may also be due to the inability of the fungus to colonize host tissues. However, OA was shown to have opposing functions that include the dampening of ROS in the initial stages of host colonization, but later promotes ROS production (Williams et al., 2011). The study by Williams et al. (2011) showed using a redoxsensitive GFP system that OA induces a reducing environment at the onset of infection to impede host defenses, but once the infection is initiated, an oxidative state persists leading to PCD of host tissue. Our results suggest that the later surge of ROS may be due to the upregulation of RBOH activity in the host by *S. sclerotiorum* and that timing of this activity and ROS production appear to be key to the pathogenic success of *S. sclerotiorum*. It is currently unclear whether the initial reductive state imposed by OA involves dampening of RBOH gene expression. Our results show that the expression of other GmRBOHs was decreased during disease development. However, this down-regulation occurred at the later stages of the infection process.

The involvement of RBOH genes in abiotic stress responses is well documented (Lin, Zhang et al. 2009, Cheng, Xu et al. 2013, Wang, Li et al. 2013, Wang, Zhang et al. 2016). Drought, in particular, is an important yield-limiting stress in soybean production. Soybean plants are most affected by drought during the reproductive growth phase; causing flower abortion, lower pod number, and reduced seed per pod. We have considered the effect of silencing GmRBOH-VI on drought tolerance in soybean. Remarkably, the silencing of these genes delayed wilting and cell death imposed by water stress. Once watering was resumed, silenced plants were able to recover quicker following prolonged exposure to drought conditions compared to control plants. During water deprivation, plant cell homeostasis is affected causing elevated levels of ROS, a process that is likely mediated by RBOHs. High levels of ROS induce oxidative damage and ultimately death of the plant. The silencing of GmRBOH-VI markedly reduced ROS levels and delayed cell death associated with water stress. Under field conditions, this could afford the plant valuable time to cope with extreme drought conditions and improve recovery. However, ROS also act as important signaling molecules that communicate with phytohormone pathways, redox-sensitive molecules, and other ROS-responsive processes to mediate acclimation to various abiotic stresses (Bhattacharjee 2005, Marino, Dunand et al. 2012, Kaur, Ghosh et al. 2014). This is supported by results in rice (Wang et al., 2016) and tomato (Li et al., 2015), where osrbohA knockout and SlRBOHB silenced plants, respectively, were found to be more sensitive to drought stress. We speculate that under our experimental conditions, silencing of GmRBOH-VI maintained ROS at sub-lethal levels without impeding signaling events, thus limiting the accumulation of excessive ROS during prolonged drought stress, which is detrimental to recovery and survivability. It is important to note the expanded RBOH family in soybean, and other members may also be involved in abiotic stress signaling, including drought.

While considering the potential utilization of GmRBOH-VI silenced plants to confer resistance to *S. sclerotiorum* in soybean, we examined the effect of silencing on nodulation in this legume. A role for RBOH proteins was reported in the symbiosis between legumes and nitrogen-fixing rhizobia. In *Medicago truncatula*, MtRBOHA was shown to be important for nodule functioning, silencing of MtRBOHA decreased nitrogen fixation activity in nodules (Marino et al., 2011). In *Phaseolus vulgaris*, the over-expression of PvRBOHB enhanced nodule nitrogen-fixing activity and delayed nodule senescence, however, it impeded arbuscular mycorrhizal fungal (AMF) colonization (Arthikala et al., 2014). Thus, RBOH genes can both inhibit and stimulate symbiotic interactions. In this study, we quantified nodules in control and GmRBOH-VI silenced plants and found that a significant reduction in nodule formation occurred in GmRBOH-VI silenced soybean. This suggests that these genes may contribute to the establishment of symbiotic associations between soybean and rhizobia. However, further studies will be required to establish if the decrease in nodule number has a significant impact on the plant's overall nitrogen-fixing capacity. It will also be interesting to determine if GmRBOH-VI silencing has a positive impact on mycorrhization, as observed in common bean (Arthikala et al., 2014). The generation of stable transgenic plants is underway to address these questions and to assess tolerance to other biotic and abiotic stresses further.

Numerous studies have discussed the importance of RBOH family members as important adapter molecules orchestrating plant responses to developmental cues, environmental insults, and microbes. In the case of *S. sclerotiorum*, it appears that this fungus can manipulate RBOH signaling to its advantage in soybean. We propose that targeting specific GmRBOH genes for silencing may constitute a viable strategy to limit SSR development and confer tolerance to other environmental insults.

Materials and Methods

Plant Material

Two varieties of Soybean (*Glycine max*), Williams 82 and Traff were used in this study. Traff variety was used for VIGS assays while the gene expression study was done on Williams 82. Soybean seedlings and plants were maintained in a growth chamber at 24° C. with 16 h light/8 h dark photoperiod cycle. Fertilization was applied using standard practices.

Identification, Domain Search and Phylogenetic Analysis of Soybean Respiratory Burst Oxidase Homologs (GmRBOHs)

*Arabidopsis* RBOH protein sequences were used to perform sequence similarity searches in JGI Phytozome (Wm82.a2.v1) (Schmutz, Cannon et al. 2010) using a stringent cutoff (E-value=0.0). We identified 17 GmRBOHs and searched their protein sequences for conserved domains using the SMART alignment tool (Letunic, Doerks et al. 2015) and PFAM (Finn, Coggill et al. 2016). The protein sequences of GmRBOH and AtRBOH were used in PhyML 3.0 to construct a maximum likelihood phylogenetic tree (Dereeper, Guignon et al. 2008, Dereeper, Audic et al. 2010). Bootstrap values >50% were used to resolve branching.

Construction of BPMV VIGS and Overexpression Constructs

To make the GmRBOH-VI silencing construct, the forward primer, GmRbohSGVIF (5'AAGGGATCCTG-CGAGCGATTACTTCGTGCT 3'; SEQ ID NO: 48) and reverse primer GmRbohSGVIR (5' TTGGGTACC-CACTCTGGTCACTACTTGCTG 3'; SEQ ID NO: 49) were used to amplify a 307 bp fragment. Restriction sites BamHI and KpnI (underlined) were added to forward and reverse primers, respectively. An extra nucleotide in reverse primer, shown in boldface type, was added to maintain the viral open reading frame. The amplified fragment was ligated into the DNA-based BPMV VIGS vector pBPMV-IA-D35 (Liu et al., 2011). Biolistic delivery of BPMV constructs was performed as previously described (Zhang, Whitham et al. 2013). Silencing was monitored using the construct pBPMV-IA-PDS-3R, which targets the soybean phytoene desaturase (PDS), leading to photo-bleaching of the plants (Zhang, Bradshaw et al. 2010). For transient overexpression, GmRBOHB, GmRBOHL, GmRBOHP and GmRBOHQ coding sequence were amplified using their corresponding primers from soybean cDNAs. Coding regions were then cloned into the Gateway™ entry vector pDONR/Zeo (Life Technologies, USA) to produce pENTR/Zeo: GmRBOHB, pENTR/Zeo: GmRBOHL, pENTR/Zeo: GmRBOHP, and pENTR/Zeo: GmRBOHQ by performing BP clonase reaction following manufacturer's protocol. pENTR/Zeo: GmRBOHB, pENTR/Zeo: GmRBOHL, pENTR/Zeo: GmRBOHP, and pENTR/Zeo: GmRBOHQ were recombined into the binary vector pGWB414 upstream of a Human influenza hemagglutinin (HA) tag (Nakagawa, Suzuki et al. 2007) resulting in pGWB414: GmRBOHB-HA, pGWB414: GmRBOHL-HA, pGWB414: GmRBOHP-HA and pGWB414: GmRBOHQ-HA, respectively. The binary plasmids were transferred into the *Agrobacterium* strain GV3101 for further experiments.

*Sclerotinia sclerotiorum* Infection and Drought Treatment

Disease assays were performed using the wild-type isolate of *S. sclerotiorum* 1980 or OA deficient mutant (A2) derived from this strain (Williams et al., 2011). Strains were grown at room temperature on potato dextrose agar (PDA). Soybean plants were infected with *S. sclerotiorum* using the cut petiole inoculation method (Hoffman, Diers et al. 2002). Actively growing *S. sclerotiorum* agar plugs were inserted into a cut petiole of the soybean plants using 1 ml pipette tip. VIGS plants were challenged with *S. sclerotiorum* 18 days after BPMV construct inoculation. In drought studies, plants were subjected to water-stress over a period of 10 days. Before starting the stress, we ensured that all pots had equal weight, and received equal amounts of soil and water. After ten days of continuous water stress, watering was resumed to assess the recovery of plants.

Immunoblotting

Total proteins were extracted from *N. benthamiana* leaves 48 h after Agro-infiltrating in lysis buffer [3× per fresh weight of tissue, 5% β-Mercaptoethanol, 1x complete protease inhibitor cocktail, 94% of 2× Laemmli buffer (Bio-Rad, USA)]. Extracts were centrifuged at 13000 rpm, for 10 min. Supernatant (30 ul) was separated on an 8% SDS-PAGE gel and transferred to nitrocellulose membrane using a trans-blot semidry cell (Bio-Rad, USA) following manufacturer's protocol. Ponceau staining (0.1% (x/v) Ponceau S in 1% (v/v) acetic acid) was performed to check for efficient protein transfer and equal loading. Skimmed milk powder (5%) was used as a blocking agent. A 1:1000 dilution of rabbit anti-HA antibody (Cell signaling technology, USA) was used as primary antibody. The goat anti-rabbit IgG, HRP-linked Antibody (Cell signaling technology, USA) was used as secondary antibody. The luminescent signal was visualized using Amersham ECL Prime Western Blotting Detection Reagent (GE Healthcare Bio-Sciences, Pittsburgh, Pa., USA) and ChemiDoc™ MP System (Bio-Rad, USA).

RNA Isolation, Reverse Transcription and Gene Expression Analysis

The internodal region at the infection site was used for RNA isolation, which included both symptomatic and non-symptomatic tissue. Stem tissues were harvested and immediately frozen in Liquid N2. RNA was isolated using Trizol reagent (Ambion life technologies, Carlsbad, Calif., USA), and then treated with RNase free DNaseI (NEB Inc. Ipswich, Mass., USA). The RNA was reverse transcribed using the AMV First-Strand cDNA synthesis kit (NEB Inc. Ipswich, Mass., USA) and oligo-dT primer according to manufacturer's instructions. The cDNA was used as template for gene expression analysis using qRT-PCR. qRT-PCR was performed using Sensi FAST SYBR® No-ROX Kit (Bioline USA Inc., USA). Each reaction consisted of 5 μl of 2× SensiFAST SYBR No-ROX Mix, 1 μl of 1:10-fold diluted cDNAs, 0.4 μl each of 10 μM gene specific forward primer and reverse primer in a final volume of 10 μl. The primer pairs used for the qRT-PCR are shown in Supplementary Table 2. qRT-PCR was performed on a CFX96 real-time PCR system (Bio-Rad, Hercules, Calif., USA). The protocol was as follows: 2 min of initial denaturation at 95° C., and then the samples were subjected to the cycling parameters of 95° C. for 5 s, 58° C. for 10 s, and 72° C. for 20 s (for 40 cycles). The relative expression of the gene was calculated using 2-\\Ct method (Livak and Schmittgen 2001) with soybean GmCon15S as an endogenous control. Three biological repeats were performed for each sample.

H2O2 Measurement

H2O2 determination with infected and non-infected soybean stem tissue was performed using a modified potassium iodide (KI) method as described (Alexieva, Sergiev et al. 2001). In brief, plant tissues were harvested, immediately frozen in liquid N2, ground and stored at −80° C. until H2O2 quantification. Frozen powder (1.5 g) was directly homogenized with 10 ml of a solution containing 0.1% w/v, trichloroacetic acid (TCA) at 40 C. The homogenized sample was centrifuged at 15000 rpm for 15 min. at 40 C. The reaction mixture consisted of 0.5 ml of 0.1% trichloroacetic acid (TCA), plant tissue extract supernatant, 0.5 mL of 100 mM K-phosphate buffer and 2 ml of reagent mix (1 M KI w/v in fresh double-distilled water). Care was taken to protect samples and solutions from light. The reaction was developed for 1 h in darkness and absorbance measured at 390 nm. Quantification was calculated using a standard curve prepared with known concentrations of H2O2.

Transient Assay in *N. benthamiana* and Symptom Quantification

For *agrobacterium*-mediated transient overexpression of candidate genes in *N. benthamiana*, bacterial cultures (*Agrobacterium tumefaciens* GV3101) were grown overnight (280 C, 200 rpm), pelleted by centrifugation, and then re-suspended in an infiltration medium (9 mM MES (2-(Nmorpholino) ethanesulfonic acid), 10 mM MgS04, 10 mM Mgcl2, pH 5.6, 300 μM acetosyringone). Cell densities were adjusted to 0.9 (OD600). Leaves of 4-5-week-old *N. benthamiana* plants were infiltrated using a needleless syringe. Twenty-four hours post agroinfiltration, detached leaves of

*N. benthamiana* were challenged with agar plugs containing actively growing mycelia of *S. sclerotiorum*. Leaves were photograhed 24 hours post challenge, and the lesion area was calculated using the image analysis software, ImageJ (Abramoff et al., 2004, Glozer, 2008).

Nodulation Assay

Ten-day-old soybean seedlings were inoculated with the pBPMV-GmRBOH-VI and the control empty vector pBPMV-0 (Kandoth, Heinz et al. 2013). Twenty-one days following VIGS construct inoculation, control and GmR-BOH-VI-silenced plants were inoculated with a 3 ml culture of *Bradyrhizobium diazoefficiens* USDA 110 at an optical density of 0.15. Whole plants were harvested after 12 days, the roots were cleaned, and the number of nodules in each plant was counted manually.

Statistical Analysis

All experiments consisted of three independent biological replicates. For statistical analysis Student's t-test was performed, and P-values of <0.05 were considered significant. For nodulation data analysis, one-way ANOVA was performed and p<0.05 was considered significant.

REFERENCES FOR EXAMPLE 1

Abramoff, M. D., et al. (2004). "Image Processing with ImageJ." Biophotonics International 11.
Alexieva, V., et al. (2001). "The effect of drought and ultraviolet radiation on growth and stress markers in pea and wheat." Plant, Cell & Environment 24(12): 1337-1344.
Alscher, R. G., et al. (1997). "Reactive oxygen species and antioxidants: Relationships in green cells." Physiologia Plantarum 100(2): 224-233.
Amselem, J., et al. (2011). "Genomic Analysis of the Necrotrophic Fungal Pathogens *Sclerotinia sclerotiorum* and *Botrytis cinerea*." PLoS Genet 7(8): e1002230.
Apel, K. and H. Hirt (2004). "REACTIVE OXYGEN SPECIES: Metabolism, Oxidative Stress, and Signal Transduction." Annual Review of Plant Biology 55(1): 373-399.
Arthikala, M.-K., et al. (2014). "RbohB, a *Phaseolus vulgaris* NADPH oxidase gene, enhances symbiosome number, bacteroid size, and nitrogen fixation in nodules and impairs mycorrhizal colonization." New Phytologist 202(3): 886-900.
Baxter, A., et al. (2013). "ROS as key players in plant stress signalling." Journal of Experimental Botany.
Bhattacharjee, S. (2005). "Reactive oxygen species and oxidative burst: Roles in stress, senescence and signal transduction in plants." Current Science 89(7): 1113-1121.
Bolton, M. D., et al. (2006). "*Sclerotinia sclerotiorum* (Lib.) de Bary: biology and molecular traits of a cosmopolitan pathogen." Molecular Plant Pathology 7(1): 1-16.
Chaouch, S., et al. (2012). "AtRbohF is a crucial modulator of defence-associated metabolism and a key actor in the interplay between intracellular oxidative stress and pathogenesis responses in *Arabidopsis*." The Plant Journal 69(4): 613-627.
Cheng, C., et al. (2013). "Genome-Wide Analysis of Respiratory Burst Oxidase Homologs in Grape (*Vitis vinifera* L.)." International Journal of Molecular Sciences 14(12): 24169-24186.
Dereeper, A., et al. (2010). "BLAST-EXPLORER helps you building datasets for phylogenetic analysis." BMC Evolutionary Biology 10(1): 1-6.
Dereeper, A., et al. (2008). "Phylogeny. fr: robust phylogenetic analysis for the non-specialist." Nucleic Acids Research 36(suppl 2): W465-W469.
Dubiella, U., et al. (2013). "Calcium-dependent protein kinase/NADPH oxidase activation circuit is required for rapid defense signal propagation." Proceedings of the National Academy of Sciences 110(21): 8744-8749.
Finn, R. D., et al. (2016). "The Pfam protein families database: towards a more sustainable future." Nucleic Acids Research 44(D1): D279-D285.
Foreman, J., et al. (2003). "Reactive oxygen species produced by NADPH oxidase regulate plant cell growth." Nature 422(6930): 442-446.
Gilbert, B. M. and T. J. Wolpert (2013). "Characterization of the LOV1-Mediated, Victorin-Induced, Cell-Death Response with Virus-Induced Gene Silencing." Molecular Plant-Microbe Interactions 26(8): 903-917.
Glozer, K. (2008). Protocol for Leaf Image Analysis-Surface Area. University of California, Davis.
Glyan'ko, A. K. and A. A. Ischenko (2010). "Structural and functional characteristics of plant NADPH oxidase: A review." Applied Biochemistry and Microbiology 46(5): 463-471.
Govrin, E. M. and A. Levine (2000). "The hypersensitive response facilitates plant infection by the necrotrophic pathogen *Botrytis cinerea*." Current Biology 10(13): 751-757.
Hoffman, D. D., et al. (2002). "Selected Soybean Plant Introductions with Partial Resistance to *Sclerotinia sclerotiorum*." Plant Disease 86(9): 971-980.
Kabbage, M., et al. (2013). "Cell Death Control: The Interplay of Apoptosis and Autophagy in the Pathogenicity of <italic> Sclerotinia sclerotiorum</italic>." PLoS Pathog 9(4): e1003287.
Kabbage, M., et al. (2015). "Pathogenic attributes of *Sclerotinia sclerotiorum*: Switching from a biotrophic to necrotrophic lifestyle." Plant Science 233: 53-60.
Kadota, Y., et al. (2015). "Regulation of the NADPH Oxidase RBOHD During Plant Immunity." Plant and Cell Physiology 56(8): 1472-1480.
Kadota, Y., et al. (2014). "Direct Regulation of the NADPH Oxidase RBOHD by the PRR-Associated Kinase BIK1 during Plant Immunity." Molecular Cell 54(1): 43-55.
Kandoth, P. K., et al. (2013). "A virus-induced gene silencing method to study soybean cyst nematode parasitism in *Glycine max*." BMC Research Notes 6(1): 255.
Kaur, C., et al. (2014). "Glyoxalases and stress tolerance in plants." Biochemical Society Transactions 42(2): 485.
Kaya, H., et al. (2014). "Ca2+-Activated Reactive Oxygen Species Production by *Arabidopsis* RbohH and RbohJ Is Essential for Proper Pollen Tube Tip Growth." The Plant Cell 26(3): 1069-1080.
Kimura, S., et al. (2012). "Protein phosphorylation is a prerequisite for the Ca2+-dependent activation of *Arabidopsis* NADPH oxidases and may function as a trigger for the positive feedback regulation of Ca2+ and reactive oxygen species." Biochimica et Biophysica Acta (BBA)—Molecular Cell Research 1823(2): 398-405.
Kobayashi, M., et al. (2007). "Calcium-Dependent Protein Kinases Regulate the Production of Reactive Oxygen Species by Potato NADPH Oxidase." The Plant Cell 19(3): 1065-1080.
Kwak, J. M., et al. (2003). "NADPH oxidase AtrbohD and AtrbohF genes function in ROS-dependent ABA signaling in *Arabidopsis*." The EMBO Journal 22(11): 2623-2633.

Lambeth, J. D. (2004). "NOX enzymes and the biology of reactive oxygen." Nat Rev Immunol 4(3): 181-189.

Lassig, R., et al. (2014). "Pollen tube NAD(P)H oxidases act as a speed control to dampen growth rate oscillations during polarized cell growth." The Plant Journal 78(1): 94-106.

Letunic, I., et al. (2015). "SMART: recent updates, new developments and status in 2015." Nucleic Acids Research 43(D1): D257-D260.

Li, X., et al. (2015). "Tomato SlRbohB, a member of the NADPH oxidase family, is required for disease resistance against Botrytis cinerea and tolerance to drought stress." Frontiers in Plant Science 6.

Liang, X., et al. (2015). "Oxaloacetate acetylhydrolase gene mutants of Sclerotinia sclerotiorum do not accumulate oxalic acid, but do produce limited lesions on host plants." Molecular Plant Pathology 16(6): 559-571.

Libault, M., et al. (2008). "Identification of Four Soybean Reference Genes for Gene Expression Normalization." The Plant Genome 1(1): 44-54.

Lin, F., et al. (2009). "Alternative Splicing and Differential Expression of Two Transcripts of Nicotine Adenine Dinucleotide Phosphate Oxidase B Gene from *Zea mays*." Journal of Integrative Plant Biology 51(3): 287-298.

Livak, K. J. and T. D. Schmittgen (2001). "Analysis of Relative Gene Expression Data Using Real-Time Quantitative PCR and the 2-ΔΔCT Method." Methods 25(4): 402-408.

Marino, D., et al. (2011). "A *Medicago truncatula* NADPH oxidase is involved in symbiotic nodule functioning." The New Phytologist 189(2): 580-592.

Marino, D., et al. (2012). "A burst of plant NADPH oxidases." Trends in Plant Science 17(1): 9-15.

Miller, G., et al. (2009). "The Plant NADPH Oxidase RBOHD Mediates Rapid Systemic Signaling in Response to Diverse Stimuli." Science Signaling 2(84): ra45-ra45.

Mittler, R., et al. (2011). "ROS signaling: the new wave?" Trends in Plant Science 16(6): 300-309.

Muller, K., et al. (2009). "The NADPH-oxidase AtrbohB plays a role in *Arabidopsis* seed after-ripening." New Phytologist 184(4): 885-897.

Nakagawa, T., et al. (2007). "Improved Gateway Binary Vectors: High-Performance Vectors for Creation of Fusion Constructs in Transgenic Analysis of Plants." Bioscience, Biotechnology, and Biochemistry 71(8): 2095-2100.

Nozaki, M., et al. (2013). "AtRbohF Contributes to Non-Host Resistance to *Magnaporthe oryzae* in *Arabidopsis*." Bioscience, Biotechnology, and Biochemistry 77(6): 1323-1325.

Oda, T., et al. (2010). "Structure of the N-terminal Regulatory Domain of a Plant NADPH Oxidase and Its Functional Implications." The Journal of Biological Chemistry 285(2): 1435-1445.

Peltier, A. J., et al. (2012). "Biology, Yield loss and Control of *Sclerotinia* Stem Rot of Soybean." Journal of Integrated Pest Management 3(2): B 1.

Peltier, A. J., et al. (2009). "Soybean Stem Lignin Concentration Relates to Resistance to *Sclerotinia sclerotiorum*." Plant Disease 93(2): 149-154.

Sagi, M. and R. Fluhr (2001). "Superoxide production by plant homologues of the gp91(phox) NADPH oxidase. Modulation of activity by calcium and by tobacco mosaic virus infection." Plant Physiol 126(3): 1281-1290.

Sagi, M. and R. Fluhr (2006). "Production of Reactive Oxygen Species by Plant NADPH Oxidases." Plant Physiology 141(2): 336-340.

Schmutz, J., et al. (2010). "Genome sequence of the palaeopolyploid soybean." Nature 463(7278): 178-183.

Sharma, P., et al. (2012). "Reactive Oxygen Species, Oxidative Damage, and Antioxidative Defense Mechanism in Plants under Stressful Conditions." Journal of Botany 2012: 26.

Simon-Plas, F., et al. (2002). "The plasma membrane oxidase NtrbohD is responsible for AOS production in elicited tobacco cells." The Plant Journal 31(2): 137-147.

Stefanato, L. F., et al. (2008). Oxaloacetate Acetyl Hydrolase is responsible for oxalic acid production in *Botrytis cinerea* and required for lesionexpansion on some, but not on most host plants. 3rd *Botrytis* Genome Workshop, Tenerife, Spain, Tenerife, Canary Islands, Spain.

Torres, M. A. and J. L. Dangl (2005). "Functions of the respiratory burst oxidase in biotic interactions, abiotic stress and development." Current Opinion in Plant Biology 8(4): 397-403.

Torres, M. A., et al. (2002). "*Arabidopsis* gp91phox homologues AtrbohD and AtrbohF are required for accumulation of reactive oxygen intermediates in the plant defense response." Proceedings of the National Academy of Sciences 99(1): 517-522.

Tripathy, B. C. and R. Oelmuller (2012). "Reactive oxygen species generation and signaling in plants." Plant Signaling & Behavior 7(12): 1621-1633.

Wang, G.-F., et al. (2013). "Characterization of Rice NADPH Oxidase Genes and Their Expression under Various Environmental Conditions." International Journal of Molecular Sciences 14(5): 9440-9458.

Wang, X., et al. (2016). "The plasma membrane NADPH oxidase OsRbohA plays a crucial role in developmental regulation and drought-stress response in rice." Physiologia Plantarum 156(4): 421-443.

Williams, B., et al. (2011). "Tipping the Balance: <italic>*Sclerotinia sclerotiorum* Secreted Oxalic Acid Suppresses Host Defenses by Manipulating the Host Redox Environment." PLoS Pathog 7(6): e1002107.

Wong, H. L., et al. (2007). "Regulation of Rice NADPH Oxidase by Binding of Rac GTPase to Its N-Terminal Extension." The Plant Cell 19(12): 4022-4034.

Xue, L., et al., (2015). "pH dependency of sclerotial development and pathogenicity revealed by using genetically defined oxalate-minus mutants of *Sclerotinia sclerotiorum*." Environmental Microbiology 17: 2896-2909.

Zhang, C., et al. (2010). "The Development of an Efficient Multipurpose Bean Pod Mottle Virus Viral Vector Set for Foreign Gene Expression and RNA Silencing." Plant Physiology 153(1): 52-65.

Zhang, C., et al. (2013). Virus-Induced Gene Silencing in Soybean and Common Bean. Virus-Induced Gene Silencing: Methods and Protocols. A. Becker. Totowa, N.J., Humana Press: 149-156.

Example 2—Plant Cells and Plants Having Hypomorphic or Null Mutations in Respiratory Burst Oxidase Homolog (RBOH) Genes In Example 1, the inventors have demonstrated that knocking down expression of GmRBOH-VI in plant cells leads to enhanced resistance to *S. sclereotiorum* and confers drought tolerance. To further the development of the technology, the inventors also plan to generate transgenic plants where these genes are knocked down or knocked out, and evaluate the performance of the transgenic plants not only against the previously described stresses, but also against a wide range of abiotic and biotic insults. Accordingly, the specific objectives for this project are:
1. Generate Stable RNAi and CRISPR/Cas9 soybean lines targeting GmRBOH-VI.
2. Evaluate the performance of the transgenic lines against a wide range of abiotic and biotic stresses in the greenhouse.
3. Conduct field test in the 2018 growing season against specific diseases and stresses in dedicated field nurseries.

The knocking down of these genes will be conducted using *agrobacterium* mediated RNAi binary vectors to generate transgenic plants though tissue culture. The inventors expect to observe similar results as described in Example 1. The stably transformed RNAi lines will be evaluated in in greenhouse and field settings. In the virus induced gene silencing studies of Example 1, the inventors were unable to silence each gene specifically. This is due to very high sequence identities among the four target genes where it was impossible to identify unique 300-400 bp regions in each gene. Therefore, the inventors propose to use CRISPR/Cas9 molecular tools where short homologous regions are sufficient for specific knock outs of the target genes See, e.g., T. B. Jacobs, P. R. LaFayette, R. J. Schmitz, W. A. Parrott, Targeted genome modifications in soybean with CRISPR/Cas9, *BMC Biotechnol.* 15 (2015) 16. The inventors will generate constructs such that they can target all the four genes together, alone and in different combinations and permutations (FIG. 12). These lines will be further advanced and evaluated against a range of stresses, including drought and *S. sclerotiorum* challenge.

We claim:

1. A transgenic plant cell transformed with a recombinant nucleic acid molecule comprising a first synthetic RNAi expression cassette that targets at least one endogenous respiratory burst oxidase gene in said transgenic plant cell to reduce or eliminate expression of at least one endogenous respiratory burst oxidase protein encoded by said at least one endogenous respiratory burst oxidase gene, wherein said synthetic RNAi expression cassette comprises a heterologous promoter operably linked to a DNA sequence encoding an inhibitory RNAi molecule which corresponds to a nucleotide sequence encoding said at least one endogenous respiratory burst oxidase protein, wherein said at least one endogenous respiratory burst oxidase protein has at least 97% amino acid sequence identity to the amino acid sequence as set forth in SEQ ID NO: 2, and wherein overexpression of said inhibitory RNAi molecule in said transgenic plant cell increases resistance to a necrotroph and increases drought tolerance as compared to a control plant cell of the same species lacking said recombinant nucleic acid molecule, and wherein the plant cell is selected from the group consisting of a soybean plant cell, a common bean plant cell and a leguminous plant cell.

2. The transgenic plant cell of claim 1, wherein expression of at least two endogenous respiratory burst oxidase proteins are reduced or eliminated.

3. The plant cell of claim 1, wherein expression of at least four endogenous respiratory burst oxidase proteins are reduced or eliminated.

4. The transgenic plant cell of claim 1, wherein said at least one endogenous respiratory burst oxidase protein has at least 98% amino acid sequence identity to the amino acid sequence as set forth in SEQ ID NO: 2.

5. The transgenic plant cell of claim 1, wherein said at least one endogenous respiratory burst oxidase protein has at least 99% amino acid sequence identity to the amino acid sequence as set forth in SEQ ID NO: 2.

6. The transgenic plant cell of claim 1, wherein said at least one endogenous respiratory burst oxidase protein has the amino acid sequence as set forth in SEQ ID NO: 2.

7. The plant cell of claim 1, wherein expression of said at least one endogenous respiratory burst oxidase protein is reduced by at least 30% as compared to said control plant cell.

8. A transgenic plant obtained from the transgenic plant cell of claim 1.

9. A transgenic plant seed obtained from the transgenic plant of claim 8, wherein said transgenic plant seed comprises said recombinant nucleic acid molecule.

10. The transgenic plant cell of claim 1, wherein the necrotroph is *Sclerotinia sclerotiorum*.

11. The transgenic plant cell of claim 1, wherein the transgenic plant cell is further transformed with a second synthetic RNAi expression cassette to reduce or eliminate expression of an additional endogenous respiratory burst oxidase gene encoding endogenous respiratory burst oxidase protein having at least 95% amino acid sequence identity to a respiratory burst oxidase protein selected from the group consisting of SEQ ID NO: 1, SEQ ID NO: 3 and SEQ ID NO: 4.

12. A transgenic plant obtained from the transgenic plant cell of claim 11.

13. A transgenic plant seed obtained from the transgenic plant of claim 12, wherein said transgenic plant seed comprises said recombinant nucleic acid molecule.

14. A method of obtaining a transgenic plant comprising:
   (i) transforming plant cells with a recombinant nucleic acid molecule comprising a first synthetic RNAi expression cassette that targets at least one endogenous respiratory burst oxidase gene in said transgenic plant cells to reduce or eliminate expression of at least one endogenous respiratory burst oxidase protein encoded by said at least one endogenous respiratory burst oxidase gene, wherein said synthetic RNAi expression cassette comprises a heterologous promoter operably linked to a DNA sequence encoding an inhibitory RNAi molecule which corresponds to a nucleotide sequence encoding said at least one endogenous respiratory burst oxidase protein, wherein said at least one endogenous respiratory burst oxidase protein has at least 97% amino acid sequence identity to the amino acid sequence as set forth in SEQ ID NO: 2, and wherein said plant cells are selected from the group consisting of soybean plant cells, common bean plant cells and leguminous plant cells;
   (ii) obtaining transgenic plants from said transformed plant cells of step (i); and
   (iii) selecting a transgenic plant from the transgenic plants of step (ii) that overexpresses said inhibitory RNA molecule in said selected transgenic plant and exhibits increased resistance to a necrotroph and increased drought tolerance as compared to a control plant of the same plant species lacking said recombinant nucleic acid molecule and grown under identical growth conditions.

15. The method of claim 14, further comprising obtaining transgenic plant seeds from the selected transgenic plant of step (iii).

16. The method of claim 14, wherein the transgenic plant cells are further transformed with a second synthetic RNAi expression cassette to reduce or eliminate expression of an additional endogenous respiratory burst oxidase gene encoding endogenous respiratory burst oxidase protein having at least 95% amino acid sequence identity to a respiratory burst oxidase protein selected from the group consisting of SEQ ID NO: 1, SEQ ID NO: 3 and SEQ ID NO: 4.

17. The method of claim 16, further comprising obtaining transgenic plant seeds from the selected transgenic plant of step (iii).

* * * * *

SEQUENCE LISTING

```
<160> NUMBER OF SEQ ID NOS: 49

<210> SEQ ID NO 1
<211> LENGTH: 876
<212> TYPE: PRT
<213> ORGANISM: Glycine max
<220> FEATURE:
<221> NAME/KEY: misc_feature
<223> OTHER INFORMATION: GmRBOHB Protein Sequence

<400> SEQUENCE: 1

Met Glu Ile Gln Leu Glu Gln Gln Gln Glu Thr Trp Ser Glu Thr Ser
1               5                   10                  15

Ser Thr Gly Ser Arg Ser Thr Arg Val Gly Phe Ser Gly Pro Met Ser
                20                  25                  30

Gly Pro Leu Val Thr Ser Asn Lys Lys Ser Ser Lys Lys Ser Ala Arg
            35                  40                  45

Phe Lys Asp Gln Glu Asp Glu Asp Phe Val Glu Ile Thr Leu Asp Val
        50                  55                  60

Arg Asp Asp Thr Val Ser Val Gln Asn Ile Arg Gly Gly Asp Pro Glu
65                  70                  75                  80

Thr Ala Leu Leu Ala Ser Arg Leu Glu Lys Arg Pro Ser Ser Leu Ser
                85                  90                  95

Val Arg Leu Arg Gln Val Ser Gln Glu Leu Lys Arg Met Thr Ser Ser
                100                 105                 110

Lys Lys Phe Asp Arg Val Asp Arg Ala Lys Ser Gly Ala Ala Arg Ala
            115                 120                 125

Leu Lys Gly Leu Lys Phe Met Thr Lys Asn Val Gly Thr Glu Gly Trp
        130                 135                 140

Ser Gln Val Asp Lys Arg Phe Asp Glu Leu Ala Val Asp Gly Lys Leu
145                 150                 155                 160

Pro Lys Thr Arg Phe Ser Gln Cys Ile Gly Met Asn Glu Ser Lys Glu
                165                 170                 175

Phe Ala Gly Glu Leu Phe Asp Ala Leu Ser Arg Arg Arg Gly Ile Thr
                180                 185                 190

Ser Ala Ser Ile Ser Lys Asp Gln Leu Arg Glu Phe Trp Glu Gln Ile
            195                 200                 205

Thr Asp Gln Ser Phe Asp Ser Arg Leu Gln Thr Phe Phe Asp Met Val
        210                 215                 220

Asp Lys Asn Ala Asp Gly Arg Ile Thr Gln Glu Val Gln Glu Ile Ile
225                 230                 235                 240
```

```
Ala Leu Ser Ala Ser Ala Asn Lys Leu Ser Lys Ile Gln Asp Arg Ala
            245                 250                 255

Glu Glu Tyr Ala Ala Leu Ile Ile Glu Glu Leu Asp Pro Asp Asn Val
        260                 265                 270

Gly Tyr Ile Glu Leu Tyr Asn Leu Glu Met Leu Leu Leu Gln Ala Pro
            275                 280                 285

Ala Gln Ser Thr His Ile Thr Thr Asp Arg Ile Met Ser Gln Met Leu
        290                 295                 300

Ser Gln Lys Leu Val Pro Thr Lys Asp His Asn Pro Ile Lys Arg Gly
305                 310                 315                 320

Phe Arg Ser Leu Ala Tyr Phe Val Glu Asp Asn Trp Lys Arg Ile Trp
                325                 330                 335

Val Ile Leu Leu Trp Leu Ser Ile Cys Ala Ala Leu Phe Thr Trp Lys
            340                 345                 350

Phe Ile Gln Tyr Lys His Arg Ala Val Phe Asp Val Met Gly Tyr Cys
            355                 360                 365

Val Thr Ser Ala Lys Gly Ala Ala Glu Thr Leu Lys Phe Asn Met Ala
        370                 375                 380

Leu Ile Leu Leu Pro Val Cys Arg Asn Thr Ile Thr Trp Leu Arg Ser
385                 390                 395                 400

Lys Thr Lys Leu Gly Met Ala Val Pro Phe Asp Asp Asn Ile Phe His
                405                 410                 415

Lys Val Ile Ala Phe Gly Ile Ala Ile Gly Val Gly Ile His Ala Ile
                420                 425                 430

Ala His Leu Thr Cys Asp Phe Pro Arg Leu Leu His Ala Thr Asp Glu
            435                 440                 445

Glu Tyr Glu Pro Met Lys Pro Phe Phe Gly Glu Asp Arg Pro Asn Asn
        450                 455                 460

Tyr Trp Trp Phe Val Lys Gly Thr Glu Trp Thr Gly Ile Ala Ile Val
465                 470                 475                 480

Val Leu Met Ala Ile Ala Tyr Thr Leu Ala Gln Pro Trp Phe Arg Arg
                485                 490                 495

Asn Arg Leu Lys Leu Pro Lys Pro Leu Lys Arg Leu Thr Gly Phe Asn
            500                 505                 510

Ala Phe Trp Tyr Ser His His Leu Phe Val Ile Val Tyr Gly Leu Phe
            515                 520                 525

Ile Val His Gly Tyr Leu Tyr Leu Ser Lys Lys Trp Tyr Lys Lys Thr
            530                 535                 540

Thr Trp Met Tyr Leu Ala Ile Pro Met Ile Leu Tyr Ala Cys Glu Arg
545                 550                 555                 560

Leu Leu Arg Ala Phe Arg Ser Gly Tyr Lys Ser Val Lys Ile Leu Lys
                565                 570                 575

Val Ala Val Tyr Pro Gly Asn Val Leu Ala Leu His Met Ser Lys Gln
            580                 585                 590

Gly Phe Lys Tyr Ser Ser Gly Gln Tyr Ile Phe Val Asn Cys Pro Asp
            595                 600                 605

Val Ser Pro Phe Gln Trp His Pro Phe Ser Ile Thr Ser Ala Pro Gly
        610                 615                 620

Asp Asp Tyr Val Ser Val His Ile Arg Thr Leu Gly Asp Trp Thr Ser
625                 630                 635                 640

Gln Leu Lys Ala Val Phe Ala Lys Ala Gln Pro Ala Ser Gly Asp Gln
                645                 650                 655

Ser Gly Leu Leu Arg Ala Asp Met Leu Gln Gly Asn Asn Ile Pro Arg
```

-continued

```
                        660                 665                 670
Met Pro Lys Leu Val Ile Asp Gly Pro Tyr Gly Ala Pro Ala Gln Asp
                675                 680                 685

Tyr Lys Asn Tyr Glu Val Ile Leu Val Gly Leu Gly Ile Gly Ala
        690                 695                 700

Thr Pro Leu Ile Ser Leu Lys Asp Val Leu Asn Asn Met Lys Gln Gln
705                 710                 715                 720

Lys Asp Ile Glu Glu Gly Met Val Glu Ser Gly Val Lys Asn Lys Arg
                725                 730                 735

Lys Pro Phe Ala Thr Asn Arg Ala Tyr Phe Tyr Trp Val Thr Arg Glu
                740                 745                 750

Gln Gly Ser Phe Glu Trp Phe Lys Gly Val Met Asp Val Ala Glu
        755                 760                 765

Tyr Asp Lys Asp Gly Ile Ile Glu Leu His Asn Tyr Cys Thr Ser Val
        770                 775                 780

Tyr Glu Glu Gly Asp Ala Arg Ser Ala Leu Ile Thr Met Leu Gln Ser
785                 790                 795                 800

Leu His His Ala Lys Ser Gly Val Asp Ile Val Ser Gly Thr Arg Val
                805                 810                 815

Lys Thr His Phe Ala Arg Pro Asn Arg Ser Val Phe Lys His Thr Ala
                820                 825                 830

Leu Lys His Pro Gly Lys Arg Val Gly Val Phe Tyr Cys Gly Ala His
                835                 840                 845

Thr Leu Val Gly Glu Leu Lys Arg Leu Ser Leu Asp Phe Ser Arg Lys
        850                 855                 860

Thr Asn Thr Lys Phe Asp Phe His Lys Glu Asn Phe
865                 870                 875

<210> SEQ ID NO 2
<211> LENGTH: 869
<212> TYPE: PRT
<213> ORGANISM: Glycine max
<220> FEATURE:
<221> NAME/KEY: misc_feature
<223> OTHER INFORMATION: GmRBOHL Protein Sequence
<220> FEATURE:
<221> NAME/KEY: misc_feature
<222> LOCATION: (42)..(42)
<223> OTHER INFORMATION: Xaa can be any naturally occurring amino acid

<400> SEQUENCE: 2

Met Val Gly Asn Gly Glu His Gly Lys Pro Glu Gln Glu Ser Gly Phe
1               5                   10                  15

Ser Gly Pro Leu Ser Gly Pro Leu Ser Gly Pro Leu Ser Gly Pro Leu
                20                  25                  30

Val Ser Asn Lys Arg Asn Ser Xaa Asn Lys Ser Ala Arg Phe
                35                  40                  45

Lys Asp Asp Glu Glu Met Val Glu Ile Thr Leu Asp Val Arg Asp Asp
                50                  55                  60

Ala Val Ser Val Gln Asn Ile Arg Gly Gly Asp Ser Glu Thr Ala Phe
65              70                  75                  80

Leu Ala Ser Arg Leu Glu Met Arg Pro Ser Ser Phe Ser Asp Arg Leu
                85                  90                  95

Arg Gln Val Ser Arg Glu Leu Lys Arg Met Thr Ser Asn Lys Ala Phe
                100                 105                 110

Asp Arg Val Asp Arg Ser Lys Ser Gly Ala Ala Arg Ala Leu Gly Gly
                115                 120                 125
```

-continued

```
Leu Lys Phe Met Thr Lys Ala Gly Thr Glu Gly Trp Ser Gln Val Glu
    130             135             140
Lys Arg Phe Asp Glu Leu Ala Ile Asp Ala Lys Leu Pro Lys Thr Arg
145             150             155             160
Phe Ser Gln Cys Ile Gly Met Asn Glu Ser Lys Glu Phe Ala Gly Leu
                165             170             175
Phe Asp Ala Leu Ala Arg Arg Gly Ile Thr Ser Ala Ser Ile Thr
            180             185             190
Lys Asp Gln Leu Arg Glu Phe Trp Glu Gln Ile Thr Asp Gln Ser Phe
    195             200             205
Asp Ser Arg Leu Gln Thr Phe Phe Asp Met Val Asp Lys Asp Ala Asp
210             215             220
Gly Arg Ile Asn Glu Glu Glu Val Lys Glu Ile Ile Leu Ser Ala Ser
225             230             235             240
Ala Asn Lys Leu Ser Lys Leu Lys Asp Arg Ala Glu Glu Tyr Ala Ala
                245             250             255
Leu Ile Met Glu Glu Leu Asp Pro Asp Asn Leu Gly Tyr Ile Glu Leu
            260             265             270
Tyr Asn Leu Glu Met Leu Leu Leu Gln Ala Pro Ala Gln Ser Thr His
    275             280             285
Ile Thr Thr Asp Ser Arg Val Leu Gln Met Leu Ser Gln Lys Leu Val
290             295             300
Pro Thr Lys Glu Tyr Asn Pro Ile Lys Arg Gly Phe Arg Ala Leu Ala
305             310             315             320
Tyr Phe Val Gln Asp Asn Trp Lys Arg Leu Trp Val Ile Ala Leu Trp
                325             330             335
Leu Ser Ile Cys Ala Gly Leu Phe Thr Trp Lys Phe Ile Gln Tyr Lys
            340             345             350
His Arg Ala Val Phe Asp Val Met Gly Tyr Cys Val Thr Val Ala Lys
    355             360             365
Gly Gly Ala Glu Thr Thr Lys Phe Asn Met Ala Leu Ile Leu Leu Pro
370             375             380
Val Cys Arg Asn Thr Ile Thr Trp Leu Arg Ser Arg Thr Lys Leu Gly
385             390             395             400
Ala Ile Ile Pro Phe Asp Asp Asn Ile Asn Phe His Lys Val Ala Phe
                405             410             415
Gly Ile Ala Ile Gly Val Gly Leu His Ala Ile Ser His Leu Thr Cys
            420             425             430
Asp Phe Pro Arg Leu Leu His Ala Thr Asp Glu Glu Tyr Glu Pro Met
    435             440             445
Lys Gln Phe Phe Gly Asp Glu Arg Pro Asn Asn Tyr Trp Trp Phe Val
450             455             460
Lys Gly Thr Glu Gly Trp Thr Val Val Met Val Val Leu Met Ala Ile
465             470             475             480
Ala Phe Ile Leu Ala Gln Pro Trp Phe Arg Arg Asn Arg Leu Lys Leu
                485             490             495
Pro Lys Thr Leu Lys Lys Leu Thr Gly Phe Asn Ala Phe Trp Tyr Ser
            500             505             510
His His Leu Phe Val Ile Val Tyr Val Leu Phe Ile Ile His Gly Tyr
    515             520             525
Phe Leu Tyr Ser Lys Lys Trp Tyr Lys Lys Thr Thr Trp Met Tyr Leu
530             535             540
```

```
Ala Val Pro Met Ile Leu Tyr Gly Cys Glu Arg Leu Leu Arg Ala Phe
545                 550                 555                 560

Arg Ser Gly Tyr Lys Ser Val Arg Ile Leu Lys Val Ala Val Tyr Pro
                565                 570                 575

Gly Asn Val Leu Ala Leu His Val Ser Lys Pro Gln Phe Lys Tyr Ser
            580                 585                 590

Ser Gly Gln Tyr Ile Tyr Val Asn Cys Ser Asp Val Ser Pro Phe Glu
        595                 600                 605

Trp His Pro Phe Ser Ile Thr Ser Ala Pro Gly Asp Asp Tyr Leu Ser
    610                 615                 620

Val His Ile Arg Thr Leu Gly Asp Trp Thr Ser Gln Leu Lys Gly Val
625                 630                 635                 640

Phe Ala Lys Ala Cys Gln Pro Ser Glu Gly Gln Ser Gly Leu Leu Arg
                645                 650                 655

Ala Asp Met Leu Gln Gly Asn Asn Lys Pro Arg Met Pro Arg Leu Leu
            660                 665                 670

Ile Asp Gly Pro Tyr Gly Ala Pro Ala Gln Asp Tyr Lys Asn Tyr Asp
        675                 680                 685

Val Ile Leu Leu Val Gly Leu Gly Ile Gly Ala Thr Pro Leu Ile Ser
    690                 695                 700

Ile Leu Lys Asp Val Leu Asn Asn Ile Lys Gln His Lys Asp Val Glu
705                 710                 715                 720

Glu Gly Glu Val Glu Lys Asp Lys Arg Lys Pro Phe Ala Thr Lys Arg
                725                 730                 735

Ala Tyr Phe Tyr Trp Val Thr Arg Glu Glu Gly Ser Phe Glu Trp Phe
            740                 745                 750

Lys Gly Val Met Asn Glu Val Glu Glu Asn Asp Lys Glu Gly Val Ile
        755                 760                 765

Glu Leu His Asn Tyr Cys Thr Ser Val Tyr Glu Glu Gly Asp Ala Arg
    770                 775                 780

Ser Ala Leu Ile Thr Met Leu Gln Ser Leu His His Ala Lys Asn Gly
785                 790                 795                 800

Val Asp Ile Val Ser Gly Thr Arg Val Lys Thr His Phe Ala Arg Pro
                805                 810                 815

Asn Trp Arg Asn Val Phe His Ala Ala Ile Lys His Pro Asp Gln Arg
            820                 825                 830

Val Gly Val Phe Tyr Cys Gly Ala His Gly Leu Val Gly Glu Leu Lys
        835                 840                 845

Lys Leu Ser Leu Asp Phe Ser Arg Lys Thr Ser Thr Lys Phe Asp Phe
    850                 855                 860

His Lys Glu Asn Phe
865

<210> SEQ ID NO 3
<211> LENGTH: 874
<212> TYPE: PRT
<213> ORGANISM: Glycine max
<220> FEATURE:
<221> NAME/KEY: misc_feature
<223> OTHER INFORMATION: GmRBOHP Protein Sequence

<400> SEQUENCE: 3

Met Glu Ile Gln Leu Glu Gln Gln Glu Ser Trp Ser Glu Thr Ser
1               5                   10                  15

Ser Thr Gly Ser Arg Ser Thr Arg Val Gly Phe Ser Gly Pro Met Ser
                20                  25                  30
```

```
Gly Pro Leu Val Thr Pro Asn Asn Lys Lys Ser Ser Lys Lys Ser Thr
            35                  40                  45

Arg Phe Lys Asp Gln Glu Glu Asp Phe Val Glu Ile Thr Leu Asp
 50                  55                  60

Val Arg Asp Asp Thr Val Ser Val Gln Asn Ile Arg Gly Gly Asp Pro
 65                  70                  75                  80

Glu Thr Ala Leu Leu Ala Ser Arg Leu Glu Lys Arg Pro Ser Ser Leu
                    85                  90                  95

Ser Val Arg Leu Arg Gln Val Ser Gln Glu Leu Lys Arg Met Thr Ser
                   100                 105                 110

Ser Lys Lys Phe Asp Arg Val Arg Thr Lys Ser Gly Ala Ala Arg Ala
                   115                 120                 125

Leu Lys Gly Leu Lys Phe Met Thr Lys Asn Val Gly Thr Glu Gly Trp
                   130                 135                 140

Ser Gln Val Glu Lys Arg Phe His Glu Leu Ala Val Glu Gly Lys Leu
145                 150                 155                 160

Pro Lys Thr Arg Phe Ser Gln Cys Ile Gly Met Asn Glu Ser Lys Glu
                   165                 170                 175

Phe Gly Glu Leu Phe Asp Ala Leu Ser Arg Arg Arg Gly Ile Thr Ser
                   180                 185                 190

Ala Ser Ile Thr Lys Asp Gln Leu Arg Glu Phe Trp Glu Gln Ile Thr
                   195                 200                 205

Asp Gln Ser Phe Asp Ser Arg Leu Gln Thr Phe Phe Asp Met Val Asp
                   210                 215                 220

Lys Asp Ala Asp Gly Arg Ile Thr Gln Glu Val Gln Glu Ile Ala
225                 230                 235                 240

Leu Ser Ala Ser Ala Asn Lys Leu Ser Lys Ile Gln Asp Arg Ala Glu
                   245                 250                 255

Glu Tyr Ala Ala Leu Ile Ile Glu Glu Leu Asp Pro Asp Asn Leu Gly
                   260                 265                 270

Tyr Ile Glu Ile Tyr Asn Leu Glu Met Leu Leu Leu Gln Ala Pro Ala
                   275                 280                 285

Gln Ser Thr Asn Ile Thr Thr Asp Ser Arg Ile Met Gln Met Leu Ser
                   290                 295                 300

Gln Lys Leu Val Pro Thr Lys Asp Tyr Asn Pro Ile Lys Arg Gly Phe
305                 310                 315                 320

Arg Ser Leu Ala Tyr Phe Val Glu Asp Asn Trp Lys Arg Ile Trp Val
                   325                 330                 335

Ile Leu Leu Trp Leu Ser Ile Cys Ala Ala Leu Phe Thr Trp Lys Phe
                   340                 345                 350

Ile Gln Tyr Lys His Arg Val Phe Asp Val Met Gly Tyr Cys Val Thr
                   355                 360                 365

Ser Ala Lys Gly Ala Ala Glu Thr Leu Lys Phe Asn Met Ala Leu Ile
370                 375                 380

Leu Leu Pro Val Cys Arg Asn Thr Ile Thr Trp Leu Arg Ser Lys Thr
385                 390                 395                 400

Lys Leu Gly Met Ala Val Pro Phe Asp Asp Asn Ile Asn Phe His Lys
                   405                 410                 415

Val Ala Phe Gly Ile Ala Ile Gly Val Gly Ile His Ala Ile Ala His
                   420                 425                 430

Leu Thr Cys Asp Phe Pro Arg Leu Leu His Ala Thr Asp Glu Glu Tyr
                   435                 440                 445
```

```
Glu Pro Met Lys Pro Phe Phe Gly Glu Asp Arg Pro Asn Asn Tyr Trp
    450                 455                 460
Trp Phe Val Lys Gly Thr Glu Gly Trp Thr Gly Ala Ile Val Val Leu
465                 470                 475                 480
Met Ala Ile Ala Tyr Thr Leu Ala Gln Pro Trp Phe Arg Arg Asn Arg
                485                 490                 495
Leu Asn Leu Pro Lys Pro Leu Lys Arg Leu Thr Gly Phe Asn Ala Phe
                500                 505                 510
Trp Tyr Ser His His Leu Phe Val Ile Val Tyr Gly Leu Phe Ile Val
        515                 520                 525
His Gly Tyr Tyr Leu Tyr Ser Lys Glu Trp Tyr Lys Lys Thr Thr Trp
    530                 535                 540
Met Tyr Leu Ala Ile Pro Met Ile Leu Tyr Ala Cys Glu Arg Leu Leu
545                 550                 555                 560
Arg Ala Phe Arg Ser Gly Tyr Lys Ser Val Lys Ile Leu Lys Val Ala
                565                 570                 575
Val Tyr Pro Gly Asn Val Leu Ala Leu His Met Ser Lys Pro Gln Gly
                580                 585                 590
Lys Tyr Ser Ser Gly Gln Tyr Ile Phe Val Asn Cys Pro Asp Val Ser
        595                 600                 605
Pro Phe Gln Trp His Pro Phe Ser Ile Thr Ser Ala Pro Gly Asp Asp
    610                 615                 620
Tyr Val Ser Val His Ile Arg Thr Leu Gly Asp Trp Thr Ser Gln Leu
625                 630                 635                 640
Lys Ala Val Phe Ala Lys Ala Cys Gln Pro Ser Ser Asp Gln Ser Gly
                645                 650                 655
Leu Leu Arg Ala Asp Met Leu Gln Gly Asn Asn Ile Pro Arg Met Pro
                660                 665                 670
Lys Leu Val Ile Asp Gly Pro Tyr Gly Ala Pro Ala Gln Asp Tyr Lys
        675                 680                 685
Asn Tyr Glu Val Ile Leu Leu Val Gly Leu Gly Ile Gly Ala Thr Pro
    690                 695                 700
Leu Ile Ser Ile Leu Lys Asp Val Leu Asn Asn Met Lys Gln Gln Lys
705                 710                 715                 720
Asp Ile Glu Glu Ala Met Val Glu Ser Gly Val Lys Asn Asn Lys Arg
                725                 730                 735
Lys Pro Phe Ala Thr Asn Arg Ala Tyr Phe Tyr Trp Val Thr Arg Glu
                740                 745                 750
Gln Gly Ser Phe Glu Trp Phe Lys Gly Val Met Asp Asp Val Ala Tyr
        755                 760                 765
Asp Lys Asp Gly Ile Ile Glu Leu His Asn Tyr Cys Thr Ser Val Tyr
    770                 775                 780
Glu Glu Gly Asp Ala Arg Ser Ala Leu Ile Thr Met Leu Gln Ser Leu
785                 790                 795                 800
His His Ala Lys Ser Gly Val Asp Ile Val Ser Gly Thr Arg Val Lys
                805                 810                 815
Thr His Phe Ala Arg Pro Asn Trp Arg Ser Lys His Thr Ala Leu Lys
                820                 825                 830
His Pro Gly Lys Arg Val Gly Val Phe Tyr Cys Gly Ala His Thr Leu
        835                 840                 845
Val Gly Glu Leu Lys Arg Leu Ser Leu Asp Phe Ser Arg Lys Thr Asn
850                 855                 860

Thr Lys Phe Asp Phe His Lys Glu Asn Phe
```

```
865                 870
```

<210> SEQ ID NO 4
<211> LENGTH: 883
<212> TYPE: PRT
<213> ORGANISM: Glycine max
<220> FEATURE:
<221> NAME/KEY: misc_feature
<223> OTHER INFORMATION: GmRBOHQ Protein Sequence

<400> SEQUENCE: 4

```
Met Glu Ile His Glu Asn Gln His Glu Ser Trp Ser Glu Thr Glu Ser
1               5                   10                  15

Thr Gly Ser Arg Ser Lys Gln Val Gly Phe Ser Gly Pro Leu Ser Gly
            20                  25                  30

Pro Leu Ser Gly Pro Leu Ser Gly Pro Leu Val Ser Ser Asn Lys Arg
        35                  40                  45

Asn Ser Ser Lys Asn Lys Ser Ala Arg Phe Lys Asp Asp Glu Glu Met
    50                  55                  60

Val Glu Ile Thr Leu Asp Val Arg Asp Asp Ala Val Ser Val Gln Asn
65                  70                  75                  80

Ile Arg Gly Gly Asp Ser Glu Thr Ala Phe Leu Ala Ser Arg Leu Glu
                85                  90                  95

Met Arg Pro Ser Ser Phe Ser Asp Arg Leu Arg Gln Val Ser Arg Glu
            100                 105                 110

Leu Lys Arg Met Thr Ser Asn Lys Ala Phe Asp Arg Val Asp Arg Ser
        115                 120                 125

Lys Ser Gly Ala Ala Arg Ala Leu Arg Gly Leu Lys Phe Met Thr Lys
    130                 135                 140

Ala Gly Thr Glu Gly Trp Ser Gln Val Glu Lys Arg Phe Asp Glu Leu
145                 150                 155                 160

Ala Ile Asp Ala Lys Leu Pro Lys Thr Arg Phe Ser Gln Cys Ile Gly
                165                 170                 175

Met Thr Glu Ser Lys Glu Phe Ala Gly Glu Leu Phe Asp Ala Leu Ala
            180                 185                 190

Arg Arg Arg Gly Ile Thr Ser Ala Ser Ile Thr Lys Asp Gln Leu Arg
        195                 200                 205

Glu Phe Trp Glu Gln Ile Thr Asp Gln Ser Phe Asp Ser Arg Leu Gln
    210                 215                 220

Thr Phe Phe Asp Met Val Asp Lys Asp Ala Asp Gly Arg Ile Asn Glu
225                 230                 235                 240

Glu Glu Val Lys Glu Ile Ile Thr Leu Ser Ala Ser Ala Asn Lys Leu
                245                 250                 255

Ser Lys Leu Lys Asp Arg Ala Glu Glu Tyr Ala Ala Leu Ile Met Glu
            260                 265                 270

Glu Leu Asp Pro Asp Asn Leu Gly Tyr Ile Glu Leu Tyr Asn Leu Glu
        275                 280                 285

Met Leu Leu Leu Gln Ala Pro Ala Gln Thr Asn Ile Thr Thr Asp Ser
    290                 295                 300

Arg Ile Leu Ser Gln Met Leu Ser Gln Lys Leu Val Pro Thr Lys Glu
305                 310                 315                 320

Tyr Asn Pro Ile Lys Arg Gly Phe Arg Ala Leu Ala Tyr Phe Val Gln
                325                 330                 335

Asp Asn Trp Lys Arg Leu Trp Val Ile Ala Leu Trp Leu Ser Ile Cys
            340                 345                 350
```

```
Ala Gly Leu Phe Thr Trp Lys Phe Ile Gln Tyr Lys His Arg Ala Val
            355                 360                 365

Phe His Val Met Gly Tyr Cys Val Thr Val Ala Lys Gly Gly Ala Glu
    370                 375                 380

Thr Thr Lys Phe Asn Met Ala Leu Ile Leu Leu Pro Val Cys Arg Asn
385                 390                 395                 400

Thr Ile Thr Trp Leu Arg Ser Arg Thr Lys Leu Gly Ala Ile Ile Phe
                405                 410                 415

Asp Asp Asn Ile Asn Phe His Lys Val Val Ala Phe Gly Ile Ala Ile
            420                 425                 430

Gly Val Gly Leu His Ala Ile Ser His Leu Thr Cys Asp Phe Pro Arg
        435                 440                 445

Leu Leu His Ala Thr Asp Val Glu Tyr Lys Pro Met Lys Gln Phe Phe
    450                 455                 460

Gly Asp Glu Arg Pro Asn Asn Tyr Trp Trp Val Lys Gly Thr Glu Gly
465                 470                 475                 480

Trp Thr Gly Val Val Met Val Val Leu Met Ala Ile Ala Phe Ile Leu
                485                 490                 495

Ala Gln Pro Trp Phe Arg Arg Asn Arg Leu Lys Leu Pro Lys Pro Leu
            500                 505                 510

Lys Lys Leu Thr Gly Phe Asn Ala Phe Trp Tyr Ser His His Leu Phe
        515                 520                 525

Val Ile Val Val Leu Phe Ile Ile His Gly Tyr Phe Leu Tyr Leu Ser
    530                 535                 540

Lys Lys Trp Tyr Lys Lys Thr Thr Trp Met Tyr Leu Ala Val Pro Met
545                 550                 555                 560

Ile Leu Tyr Gly Cys Glu Arg Leu Leu Arg Ala Phe Arg Ser Gly Tyr
                565                 570                 575

Lys Ser Val Arg Ile Leu Lys Val Ala Val Tyr Pro Gly Asn Val Leu
            580                 585                 590

Ala Leu His Val Ser Lys Pro His Gly Phe Lys Tyr Ser Ser Gly Gln
        595                 600                 605

Tyr Ile Tyr Val Asn Cys Ser Asp Val Ser Pro Phe Glu Trp His Pro
    610                 615                 620

Phe Ser Ile Thr Ser Ala Pro Gly Asp Asp Tyr Leu Ser Val His Ile
625                 630                 635                 640

Arg Thr Leu Gly Asp Trp Thr Ser Gln Leu Lys Gly Val Phe Ala Lys
                645                 650                 655

Ala Cys Gln Pro Ala Ser Asp Gly Gln Ser Gly Leu Leu Arg Ala Asp
            660                 665                 670

Met Leu Gln Gly Asn Asn Lys Pro Arg Met Pro Arg Leu Leu Ile Asp
        675                 680                 685

Gly Pro Tyr Gly Ala Pro Ala Gln Asp Tyr Lys Asn Tyr Glu Val Ile
    690                 695                 700

Leu Leu Val Gly Gly Ile Gly Ala Thr Pro Leu Ile Ser Ile Leu Lys
705                 710                 715                 720

Asp Val Leu Asn Asn Ile Lys Gln His Lys Asp Val Glu Glu Gly Ala
                725                 730                 735

Val Glu Lys Asp Asn Lys Arg Lys Pro Phe Ala Thr Lys Arg Ala Tyr
            740                 745                 750

Phe Tyr Trp Val Thr Arg Glu Glu Gly Ser Phe Glu Trp Phe Lys Gly
        755                 760                 765

Val Met Asn Glu Val Glu Glu Asn Asp Lys Glu Gly Val Ile Glu Leu
```

His Asn Tyr Cys Thr Ser Val Tyr Glu Glu Gly Asp Ala Arg Ser Ala
785                 790                 795                 800

Leu Ile Thr Met Leu Gln Ser Leu His His Ala Lys Asn Gly Val Asp
            805                 810                 815

Ile Val Ser Gly Thr Arg Val Lys His Phe Ala Arg Pro Asn Trp Arg
        820                 825                 830

Asn Val Phe Lys His Ala Ala Ile Lys His Pro Asp Gln Arg Val Gly
    835                 840                 845

Val Phe Tyr Cys Gly Ala His Gly Leu Val Gly Glu Leu Lys Arg Leu
850                 855                 860

Ser Leu Asp Phe Ser Arg Lys Thr Ser Thr Lys Phe Asp Phe His Lys
865                 870                 875                 880

Glu Asn Phe

<210> SEQ ID NO 5
<211> LENGTH: 843
<212> TYPE: PRT
<213> ORGANISM: Arabidopsis thaliana
<220> FEATURE:
<221> NAME/KEY: misc_feature
<223> OTHER INFORMATION: AtRBOHB Protein Sequence

<400> SEQUENCE: 5

Met Arg Glu Glu Met Glu Ser Ser Glu Gly Glu Thr Asn Lys
1               5                   10                  15

Ile Ser Arg Cys Lys Ala Thr Gly Ser Asp Asn Pro Asp Glu Asp Tyr
            20                  25                  30

Val Glu Ile Thr Leu Glu Val Arg Asp Glu Thr Ile Asn Thr Met Lys
        35                  40                  45

Ala Lys Ala Thr Leu Arg Ser Val Leu Ser Gly Arg Leu Lys Thr Met
    50                  55                  60

Val Lys Ser Leu Ser Phe Ala Ser Arg Arg Leu Asp Arg Ser Lys Ser
65                  70                  75                  80

Phe Gly Ala Met Phe Ala Leu Arg Gly Leu Arg Phe Ile Ala Lys Asn
                85                  90                  95

Asp Ala Val Gly Arg Gly Trp Asp Glu Val Ala Met Arg Phe Asp Lys
            100                 105                 110

Leu Ala Val Glu Gly Lys Leu Pro Lys Ser Lys Phe Gly His Cys Ile
        115                 120                 125

Gly Met Val Glu Ser Ser Glu Phe Val Asn Glu Leu Phe Glu Ala Leu
    130                 135                 140

Val Arg Arg Arg Gly Thr Thr Ser Ser Ser Ile Thr Lys Thr Glu Leu
145                 150                 155                 160

Phe Glu Phe Trp Glu Gln Ile Thr Gly Asn Ser Phe Asp Asp Arg Leu
                165                 170                 175

Gln Ile Phe Phe Asp Met Val Asp Lys Asn Leu Asp Gly Arg Ile Thr
            180                 185                 190

Gly Asp Glu Val Lys Glu Ile Ile Ala Leu Ser Ala Ser Ala Asn Lys
        195                 200                 205

Leu Ser Lys Ile Lys Glu Asn Val Asp Glu Tyr Ala Ala Leu Ile Met
    210                 215                 220

Glu Glu Leu Asp Arg Asp Asn Leu Gly Tyr Ile Glu Leu His Asn Leu
225                 230                 235                 240

Glu Thr Leu Leu Leu Gln Val Pro Ser Gln Ser Asn Asn Ser Pro Ser

-continued

```
                245                 250                 255
Ser Ala Asn Lys Arg Ala Leu Asn Lys Met Leu Ser Gln Lys Leu Ile
            260                 265                 270

Pro Thr Lys Asp Arg Asn Pro Val Lys Arg Phe Ala Met Asn Ile Ser
            275                 280                 285

Tyr Phe Leu Glu Asn Trp Lys Arg Ile Trp Val Leu Thr Leu Trp
    290                 295                 300

Ile Ser Ile Cys Ile Thr Leu Phe Thr Trp Lys Phe Leu Gln Tyr Lys
305                 310                 315                 320

Arg Lys Thr Val Phe Glu Val Met Gly Tyr Cys Val Thr Val Ala Lys
                325                 330                 335

Gly Ser Ala Glu Thr Leu Lys Phe Asn Met Ala Leu Ile Leu Leu Pro
            340                 345                 350

Val Cys Arg Asn Thr Ile Thr Trp Leu Arg Thr Lys Ser Lys Leu Ile
            355                 360                 365

Gly Ser Val Val Pro Phe Asp Asp Asn Ile Asn Phe His Lys Val Val
            370                 375                 380

Ala Phe Gly Ile Ala Val Gly Ile Gly Leu His Ala Ile Ser His Leu
385                 390                 395                 400

Ala Cys Asp Phe Pro Arg Leu Leu His Ala Lys Asn Val Glu Phe Glu
                405                 410                 415

Pro Met Lys Lys Phe Phe Gly Asp Glu Arg Pro Glu Asn Tyr Gly Trp
            420                 425                 430

Phe Met Lys Gly Thr Asp Gly Trp Thr Gly Val Thr Met Val Val Leu
            435                 440                 445

Met Leu Val Ala Tyr Val Leu Ala Gln Ser Trp Phe Arg Arg Asn Arg
    450                 455                 460

Ala Asn Leu Pro Lys Ser Leu Lys Arg Leu Thr Gly Phe Asn Ala Phe
465                 470                 475                 480

Trp Tyr Ser His His Leu Phe Val Ile Val Tyr Val Leu Leu Ile Val
                485                 490                 495

His Gly Tyr Phe Val Tyr Leu Ser Lys Glu Trp Tyr His Lys Thr Thr
            500                 505                 510

Trp Met Tyr Leu Ala Val Pro Val Leu Leu Tyr Ala Phe Glu Arg Leu
            515                 520                 525

Ile Arg Ala Phe Arg Pro Gly Ala Lys Ala Val Lys Val Leu Lys Val
    530                 535                 540

Ala Val Tyr Pro Gly Asn Val Leu Ser Leu Tyr Met Ser Lys Pro Lys
545                 550                 555                 560

Gly Phe Lys Tyr Thr Ser Gly Gln Tyr Ile Tyr Ile Asn Cys Ser Asp
                565                 570                 575

Val Ser Pro Leu Gln Trp His Pro Phe Ser Ile Thr Ser Ala Ser Gly
            580                 585                 590

Asp Asp Tyr Leu Ser Val His Ile Arg Thr Leu Gly Asp Trp Thr Ser
            595                 600                 605

Gln Leu Lys Ser Leu Tyr Ser Lys Val Cys Gln Leu Pro Ser Thr Ser
    610                 615                 620

Gln Ser Gly Leu Phe Ile Ala Asp Ile Gly Gln Ala Asn Asn Ile Thr
625                 630                 635                 640

Arg Phe Pro Arg Leu Leu Ile Asp Gly Pro Tyr Gly Ala Pro Ala Gln
                645                 650                 655

Asp Tyr Arg Asn Tyr Asp Val Leu Leu Leu Val Gly Leu Gly Ile Gly
            660                 665                 670
```

```
Ala Thr Pro Leu Ile Ser Ile Ile Arg Asp Val Leu Asn Asn Ile Lys
            675                 680                 685

Asn Gln Asn Ser Ile Glu Arg Gly Thr Asn Gln His Ile Lys Asn Tyr
    690                 695                 700

Val Ala Thr Lys Arg Ala Tyr Phe Tyr Trp Val Thr Arg Glu Gln Gly
705                 710                 715                 720

Ser Leu Glu Trp Phe Ser Glu Val Met Asn Glu Val Ala Glu Tyr Asp
                725                 730                 735

Ser Glu Gly Met Ile Glu Leu His Asn Tyr Cys Thr Ser Val Tyr Glu
            740                 745                 750

Glu Gly Asp Ala Arg Ser Ala Leu Ile Thr Met Leu Gln Ser Leu His
        755                 760                 765

His Ala Lys Ser Gly Ile Asp Ile Val Ser Gly Thr Arg Val Arg Thr
    770                 775                 780

His Phe Ala Arg Pro Asn Trp Arg Ser Val Phe Lys His Val Ala Val
785                 790                 795                 800

Asn His Val Asn Gln Arg Val Gly Val Phe Tyr Cys Gly Asn Thr Cys
                805                 810                 815

Ile Ile Gly Glu Leu Lys Arg Leu Ala Gln Asp Phe Ser Arg Lys Thr
            820                 825                 830

Thr Thr Lys Phe Glu Phe His Lys Glu Asn Phe
        835                 840

<210> SEQ ID NO 6
<211> LENGTH: 20
<212> TYPE: DNA
<213> ORGANISM: Artificial Sequence
<220> FEATURE:
<223> OTHER INFORMATION: Synthetic: GmRBOHAF primer

<400> SEQUENCE: 6
cctcccttag ctgggaagag                                                   20

<210> SEQ ID NO 7
<211> LENGTH: 21
<212> TYPE: DNA
<213> ORGANISM: Artificial Sequence
<220> FEATURE:
<223> OTHER INFORMATION: Synthetic: GmRBOHAR primer

<400> SEQUENCE: 7
atcccgagac cgacaagtag c                                                 21

<210> SEQ ID NO 8
<211> LENGTH: 20
<212> TYPE: DNA
<213> ORGANISM: Artificial Sequence
<220> FEATURE:
<223> OTHER INFORMATION: Synthetic: GmRBOHBF primer

<400> SEQUENCE: 8
ggccgtgcaa ttgttcattc                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic: GmRBOHBR primer

<400> SEQUENCE: 9
```

```
tccgaccatg tttcctgttg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic: GmRBOHCF primer

<400> SEQUENCE: 10
tacctgcatc gctctctctt                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic: GmRBOHCR primer

<400> SEQUENCE: 11
cctgaatttc cctcctccta                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic: GmRBOHDF primer

<400> SEQUENCE: 12
cagaaagccg gatacgaaca                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic: GmRBOHDR primer

<400> SEQUENCE: 13
taagagtagg gcttccacag                                              20

<210> SEQ ID NO 14
<211> LENGTH: 22
<212> TYPE: DNA
<213> ORGANISM: Artificial Sequence
<220> FEATURE:
<223> OTHER INFORMATION: Synthetic: GmRBOHEF primer

<400> SEQUENCE: 14
gtggactcct aagagctgaa tg                                           22

<210> SEQ ID NO 15
<211> LENGTH: 22
<212> TYPE: DNA
<213> ORGANISM: Artificial Sequence
<220> FEATURE:
<223> OTHER INFORMATION: Synthetic: GmRBOHER primer

<400> SEQUENCE: 15
tagcaacacc acctcatact cc                                           22

<210> SEQ ID NO 16
<211> LENGTH: 20
<212> TYPE: DNA
```

```
<213> ORGANISM: Artificial Sequence
<220> FEATURE:
<223> OTHER INFORMATION: Synthetic: GmRBOHFF primer

<400> SEQUENCE: 16
tctcaagcgc accgatttcg                                                    20

<210> SEQ ID NO 17
<211> LENGTH: 23
<212> TYPE: DNA
<213> ORGANISM: Artificial Sequence
<220> FEATURE:
<223> OTHER INFORMATION: Synthetic: GmRBOHFR primer

<400> SEQUENCE: 17
ctcagctctc aaccttcgtt tac                                                23

<210> SEQ ID NO 18
<211> LENGTH: 19
<212> TYPE: DNA
<213> ORGANISM: Artificial Sequence
<220> FEATURE:
<223> OTHER INFORMATION: Synthetic: GmRBOHGF primer

<400> SEQUENCE: 18
acctgacaac ggcaagagt                                                     19

<210> SEQ ID NO 19
<211> LENGTH: 22
<212> TYPE: DNA
<213> ORGANISM: Artificial Sequence
<220> FEATURE:
<223> OTHER INFORMATION: Synthetic: GmRBOHGR primer

<400> SEQUENCE: 19
cgtaaggacc atcaattaga ac                                                 22

<210> SEQ ID NO 20
<211> LENGTH: 23
<212> TYPE: DNA
<213> ORGANISM: Artificial Sequence
<220> FEATURE:
<223> OTHER INFORMATION: Synthetic: GmRBOHHF primer

<400> SEQUENCE: 20
accaaggaat ggaacaagaa gac                                                23

<210> SEQ ID NO 21
<211> LENGTH: 23
<212> TYPE: DNA
<213> ORGANISM: Artificial Sequence
<220> FEATURE:
<223> OTHER INFORMATION: Synthetic: GmRBOHHR primer

<400> SEQUENCE: 21
ctcggtgatc tttactcctg aaa                                                23

<210> SEQ ID NO 22
<211> LENGTH: 23
<212> TYPE: DNA
<213> ORGANISM: Artificial Sequence
<220> FEATURE:
<223> OTHER INFORMATION: Synthetic: GmRBOHIF primer

<400> SEQUENCE: 22
agtggacttc taagagctga atg                                                23
```

<210> SEQ ID NO 23
<211> LENGTH: 22
<212> TYPE: DNA
<213> ORGANISM: Artificial Sequence
<220> FEATURE:
<223> OTHER INFORMATION: Synthetic: GmRBOHIR primer

<400> SEQUENCE: 23
catactccct gtagtcttgt gc                                            22

<210> SEQ ID NO 24
<211> LENGTH: 23
<212> TYPE: DNA
<213> ORGANISM: Artificial Sequence
<220> FEATURE:
<223> OTHER INFORMATION: Synthetic: GmRBOHJF primer

<400> SEQUENCE: 24
gcaggaacag gctgaagaat atg                                           23

<210> SEQ ID NO 25
<211> LENGTH: 23
<212> TYPE: DNA
<213> ORGANISM: Artificial Sequence
<220> FEATURE:
<223> OTHER INFORMATION: Synthetic: GmRBOHJR primer

<400> SEQUENCE: 25
ggctgtagtt aaggtacgtg tcc                                           23

<210> SEQ ID NO 26
<211> LENGTH: 20
<212> TYPE: DNA
<213> ORGANISM: Artificial Sequence
<220> FEATURE:
<223> OTHER INFORMATION: Synthetic: GmRBOHKF primer

<400> SEQUENCE: 26
caccaagatt gccgctaaac                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic: GmRBOHKR primer

<400> SEQUENCE: 27
cagctccagt gatagcttct                                               20

<210> SEQ ID NO 28
<211> LENGTH: 24
<212> TYPE: DNA
<213> ORGANISM: Artificial Sequence
<220> FEATURE:
<223> OTHER INFORMATION: Synthetic: GmRBOHLF primer

<400> SEQUENCE: 28
gaaggatcag ttgcgtgaat tttg                                          24

<210> SEQ ID NO 29
<211> LENGTH: 24
<212> TYPE: DNA
<213> ORGANISM: Artificial Sequence
<220> FEATURE:

-continued

<223> OTHER INFORMATION: Synthetic: GmRBOHLR primer

<400> SEQUENCE: 29
cttcttcatt aattcgtcca tcgg                                      24

<210> SEQ ID NO 30
<211> LENGTH: 21
<212> TYPE: DNA
<213> ORGANISM: Artificial Sequence
<220> FEATURE:
<223> OTHER INFORMATION: Synthetic: GmRBOHMF primer

<400> SEQUENCE: 30
tacgttgcac ctttcgatga t                                         21

<210> SEQ ID NO 31
<211> LENGTH: 21
<212> TYPE: DNA
<213> ORGANISM: Artificial Sequence
<220> FEATURE:
<223> OTHER INFORMATION: Synthetic: GmRBOHMR primer

<400> SEQUENCE: 31
cgccatccaa atacgtctta t                                         21

<210> SEQ ID NO 32
<211> LENGTH: 22
<212> TYPE: DNA
<213> ORGANISM: Artificial Sequence
<220> FEATURE:
<223> OTHER INFORMATION: Synthetic: GmRBOHNF primer

<400> SEQUENCE: 32
tcaccaagat tgcctctaaa ca                                        22

<210> SEQ ID NO 33
<211> LENGTH: 21
<212> TYPE: DNA
<213> ORGANISM: Artificial Sequence
<220> FEATURE:
<223> OTHER INFORMATION: Synthetic: GmRBOHNR primer

<400> SEQUENCE: 33
gtggctcagc tcaagtgata g                                         21

<210> SEQ ID NO 34
<211> LENGTH: 20
<212> TYPE: DNA
<213> ORGANISM: Artificial Sequence
<220> FEATURE:
<223> OTHER INFORMATION: Synthetic: GmRBOHOF primer

<400> SEQUENCE: 34
aaagcagtcg gttgtggaga                                           20

<210> SEQ ID NO 35
<211> LENGTH: 22
<212> TYPE: DNA
<213> ORGANISM: Artificial Sequence
<220> FEATURE:
<223> OTHER INFORMATION: Synthetic: GmRBOHOR primer

<400> SEQUENCE: 35
atgtgtgtgt attggagtcc tg                                        22

```
<210> SEQ ID NO 36
<211> LENGTH: 23
<212> TYPE: DNA
<213> ORGANISM: Artificial Sequence
<220> FEATURE:
<223> OTHER INFORMATION: Synthetic: GmRBOHPF primer

<400> SEQUENCE: 36
ggcataacat cagcttccat aac                                              23

<210> SEQ ID NO 37
<211> LENGTH: 20
<212> TYPE: DNA
<213> ORGANISM: Artificial Sequence
<220> FEATURE:
<223> OTHER INFORMATION: Synthetic: GmRBOHPR primer

<400> SEQUENCE: 37
ttcttccgtc ggcatctttg                                                  20

<210> SEQ ID NO 38
<211> LENGTH: 22
<212> TYPE: DNA
<213> ORGANISM: Artificial Sequence
<220> FEATURE:
<223> OTHER INFORMATION: Synthetic: GmRBOHQF primer

<400> SEQUENCE: 38
aggatcagct gcgtgaattt tg                                               22

<210> SEQ ID NO 39
<211> LENGTH: 21
<212> TYPE: DNA
<213> ORGANISM: Artificial Sequence
<220> FEATURE:
<223> OTHER INFORMATION: Synthetic: GmRBOHQR primer

<400> SEQUENCE: 39
tcgtccatca gcatctttgt c                                                21

<210> SEQ ID NO 40
<211> LENGTH: 52
<212> TYPE: DNA
<213> ORGANISM: Artificial Sequence
<220> FEATURE:
<223> OTHER INFORMATION: Synthetic: GmRBOHBattB1F primer

<400> SEQUENCE: 40
ggggacaagt ttgtacaaaa aagcaggctt catggagatt caattggagc ag              52

<210> SEQ ID NO 41
<211> LENGTH: 58
<212> TYPE: DNA
<213> ORGANISM: Artificial Sequence
<220> FEATURE:
<223> OTHER INFORMATION: Synthetic: GmRBOHBattB2R primer

<400> SEQUENCE: 41
ggggaccact ttgtacaaga aagctgggtc aaaattctct ttatgaaaat caaacttg        58

<210> SEQ ID NO 42
<211> LENGTH: 51
<212> TYPE: DNA
<213> ORGANISM: Artificial Sequence
<220> FEATURE:
<223> OTHER INFORMATION: Synthetic: GmRBOHLattB1F primer
```

```
<400> SEQUENCE: 42
ggggacaagt tgtacaaaa aagcaggctt catggtggag atcacgctgg a              51

<210> SEQ ID NO 43
<211> LENGTH: 61
<212> TYPE: DNA
<213> ORGANISM: Artificial Sequence
<220> FEATURE:
<223> OTHER INFORMATION: Synthetic: GmRBOHLattB2R primer

<400> SEQUENCE: 43
ggggaccact ttgtacaaga aagctgggtc aaaattttct ttgtgaaaat caaacttggt    60
g                                                                   61

<210> SEQ ID NO 44
<211> LENGTH: 50
<212> TYPE: DNA
<213> ORGANISM: Artificial Sequence
<220> FEATURE:
<223> OTHER INFORMATION: Synthetic: GmRBOHPattB1F primer

<400> SEQUENCE: 44
ggggacaagt ttgtacaaaa aagcaggctt catggagatt cagttagagc               50

<210> SEQ ID NO 45
<211> LENGTH: 59
<212> TYPE: DNA
<213> ORGANISM: Artificial Sequence
<220> FEATURE:
<223> OTHER INFORMATION: Synthetic: GmRBOHPattB2R primer

<400> SEQUENCE: 45
ggggaccact ttgtacaaga aagctgggtc aaaattctct ttatgaaaat caaacttgg     59

<210> SEQ ID NO 46
<211> LENGTH: 53
<212> TYPE: DNA
<213> ORGANISM: Artificial Sequence
<220> FEATURE:
<223> OTHER INFORMATION: Synthetic: GmRBOHQattB1F primer

<400> SEQUENCE: 46
ggggacaagt ttgtacaaaa aagcaggctt catggagatt cacgaaaacc aac           53

<210> SEQ ID NO 47
<211> LENGTH: 58
<212> TYPE: DNA
<213> ORGANISM: Artificial Sequence
<220> FEATURE:
<223> OTHER INFORMATION: Synthetic: GmRBOHQattB2R primer

<400> SEQUENCE: 47
ggggaccact ttgtacaaga aagctgggtc aaaattttct ttgtgaaaat caaacttg      58

<210> SEQ ID NO 48
<211> LENGTH: 30
<212> TYPE: DNA
<213> ORGANISM: Artificial Sequence
<220> FEATURE:
<223> OTHER INFORMATION: Synthetic: GmRbohSGVIF

<400> SEQUENCE: 48
aagggatcct gcgagcgatt acttcgtgct                                     30
```

```
<210> SEQ ID NO 49
<211> LENGTH: 30
<212> TYPE: DNA
<213> ORGANISM: Artificial Sequence
<220> FEATURE:
<223> OTHER INFORMATION: Sythetic: GmRbohSGVIR

<400> SEQUENCE: 49
ttgggtaccc actctggtca ctacttgctg                                30
```